United States Patent

Kawamura et al.

[11] Patent Number: 5,834,401
[45] Date of Patent: Nov. 10, 1998

[54] NITROGEN-CONTAINING CYCLIC COMPOUNDS AND HERBICIDES CONTAINING THE SAME AS ACTIVE INGREDIENT

[75] Inventors: Yasuo Kawamura; Eiichi Oya, both of Funabashi; Kaoru Itoh, deceased, late of Yamamoto-gun, by Mariko Itoh, legal representative; Hiroshi Kita, Funabashi; Hisashi Nakata, Funabashi; Kanji Sawada, Funabashi; Yoshitake Tamada, Funabashi; Tsutomu Nawamaki, Minamisaitama-gun; Kimihiro Ishikawa, Minamisaitama-gun; Kenichi Shiojima, Minamisaitama-gun; Chiaki Kawaguchi, Minamisaitama-gun; Kunimitsu Nakahira, Minamisaitama-gun, all of Japan

[73] Assignee: Nissan Chemical Industries, Ltd., Tokyo, Japan

[21] Appl. No.: 693,070

[22] PCT Filed: Feb. 17, 1995

[86] PCT No.: PCT/JP95/00230

§ 371 Date: Dec. 12, 1996

§ 102(e) Date: Dec. 12, 1996

[87] PCT Pub. No.: WO95/22523

PCT Pub. Date: Aug. 24, 1995

[30] Foreign Application Priority Data

| Feb. 18, 1994 | [JP] | Japan | 6-21080 |
| Mar. 30, 1994 | [JP] | Japan | 6-60921 |
| Apr. 13, 1994 | [JP] | Japan | 6-74725 |
| Jul. 5, 1994 | [JP] | Japan | 6-157035 |
| Aug. 5, 1994 | [JP] | Japan | 6-184284 |
| Sep. 26, 1994 | [JP] | Japan | 6-229267 |
| Jan. 19, 1995 | [JP] | Japan | 7-24788 |

[51] Int. Cl.⁶ .................. A01N 43/40; C07D 211/40
[52] U.S. Cl. ............ 504/254; 504/244; 504/255; 546/212; 546/216; 546/221; 546/283.4; 546/300
[58] Field of Search ......................... 546/243, 300, 546/212, 216, 221, 283.4; 504/244, 254, 255

[56] References Cited

U.S. PATENT DOCUMENTS

| 5,234,895 | 8/1993 | Felix ......................... 504/254 |
| 5,238,908 | 8/1993 | Lange et al. ............. 504/244 |

FOREIGN PATENT DOCUMENTS

| 0 218 048 A2 | 4/1987 | European Pat. Off. . |
| 0 372 586 | 6/1990 | European Pat. Off. . |
| WO95/18113 | 7/1995 | WIPO . |

OTHER PUBLICATIONS

European Search Report, mailed Jul. 14, 1997.

*Primary Examiner*—Mukund J. Shah
*Assistant Examiner*—Pavanaram K Sripada
*Attorney, Agent, or Firm*—David G. Conlin; Peter F. Corless; Dike, Bronstein, Roberts & Cushman, LLP

[57] ABSTRACT

The present invention provides a nitrogen-containing cyclic compound represented by the formula (1):

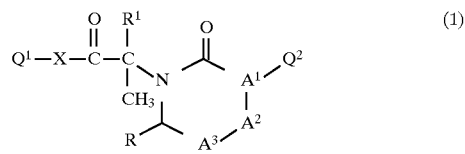

(wherein $R^1$ represents an alkyl group; R represents a hydrogen atom or an alkyl group; X represents an oxygen or sulfur atom or $NR^3$; $Q^1$ represents a hydrogen atom, or an alkyl, cycloalkyl, alkenyl or alkynyl group, or a phenyl, naphthyl or heterocyclic group etc.; $Q^2$ represents an alkyl, cycloalkyl or alkenyl group, or a phenyl or thienyl group etc.; $A^1$ represents a carbon or nitrogen atom; $A^2$ represents $CR^2$ or $NR^2$, or an oxygen or sulfur atom, or SO or $SO_2$; $A^3$ represents a single bond, or an oxygen or sulfur atom, or $CR^5$ or $NR^5$) and a herbicide comprising the same, which herbicide exhibits very high herbicidal activity at very low application rate and has selectivity against crops.

8 Claims, No Drawings

NITROGEN-CONTAINING CYCLIC COMPOUNDS AND HERBICIDES CONTAINING THE SAME AS ACTIVE INGREDIENT

This application is a 371 of PCT/JP95/00230 filed Feb. 17, 1995.

FIELD OF THE INVENTION

The present invention relates to novel nitrogen-containing cyclic compounds and selective herbicides containing the nitrogen-containing cyclic compounds as active ingredients.

BACKGROUND OF THE INVENTION

It is well known that a particular nitrogen-containing cyclic compound having a cyclic amide or urea structure in its ring has herbicidal activity. It is, for example, described in JP-A-49-132073, JP-A-54-70283, JP-A-57-139069, JP-A-58-140078, JP-A-3-176475, JP-A-3-204855, JP-A-4-89485, JP-A-5-201811, JP-A-5-221972, JP-A-5-221973, JP-A-6-25160 and JP-A-6-234763; EP-A-372586, EP-A-557691 and EP-A-600507; U.S Pat. No. 3272842, U.S. Pat. No. 3334098 and U.S. Pat. No. 5076832; DE-4213026; and WO 93/15064 and WO 94/13665.

However, each of the compounds disclosed therein is not necessarily satisfactory as a herbicide, and is thus desired to be improved in herbicidal activity and crop selectivity.

SUMMARY OF THE INVENTION

The present invention provides nitrogen-containing cyclic compounds represented by the formula (1) (hereinafter referred to as compounds of the present invention), herbicides containing the said compounds and a process for controlling weeds by using them:

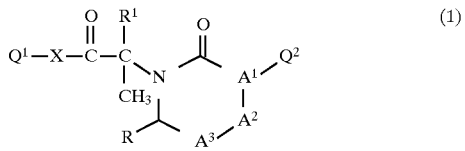

wherein
- $R^1$ represents a $C_1$–$C_4$ alkyl group;
- R represents a hydrogen atom or a $C_1$–$C_4$ alkyl group;
- X represents an oxygen or sulfur atom or $NR^3$ (wherein $R^3$ represents a hydrogen atom or a methyl group);
- $Q^1$ represents a hydrogen atom, or a $C_1$–$C_6$ alkyl, $C_3$–$C_7$ cycloalkyl, $C_3$–$C_6$ alkenyl or $C_3$–$C_6$ alkynyl group, or an optionally substituted phenyl, naphthyl or heterocyclic group;
- $Q^2$ represents a $C_1$–$C_6$ alkyl, $C_3$–$C_7$ cycloalkyl or $C_3$–$C_6$ alkenyl group, or an optionally substituted phenyl or thienyl group;
- $A^1$ represents a carbon or nitrogen atom;
- $A^2$ represents $CR^2$ (wherein $R^2$ represents a hydrogen atom, or a $C_1$–$C_4$ alkyl, $C_3$–$C_6$ alkenyl or $C_3$–$C_6$ alkynyl group) or $NR^2$ (wherein $R^2$ is the same meaning as defined above), or an oxygen or sulfur atom, or SO or $SO_2$;
- $A^3$ represents a single bond, or an oxygen or sulfur atom, or $CR^5$ (wherein $R^5$ represents a hydrogen atom or a $C_1$–$C_4$ alkyl group) or $NR^5$ (wherein $R^5$ is the same meaning as defined above);
- the ring comprising $A^3$ may have one double bond within the ring when $A^3$ represents a single bond or an oxygen or sulfur atom, and may have one or two double bonds within the ring when $A^3$ represents $CR^5$ or $NR^5$ (wherein $R^5$ is the same meaning as defined above), provided that the compounds are excluded in which both of $A^2$ and $A^3$ represent oxygen atoms, and in which $A^3$ represents a single bond, $A^1$ represents a carbon atom, $A^2$ represents $CR^2$ (wherein $R^2$ is the same meaning as defined above), $A^1$ and $A^2$ are bonded through a double bond, $Q^2$ represents a $C_1$–$C_6$ alkyl, $C_3$–$C_7$ cycloalkyl, $C_3$–$C_6$ alkenyl group or an optionally substituted phenyl group, and $Q^1$ represents a hydrogen atom or a $C_1$–$C_6$ alkyl, $C_3$–$C_7$ cycloalkyl, $C_3$–$C_6$ alkenyl, $C_3$–$C_6$ alkynyl group or an optionally substituted phenyl group.

Preferred compounds of the formula (1) include those represented by the formula (1-a):

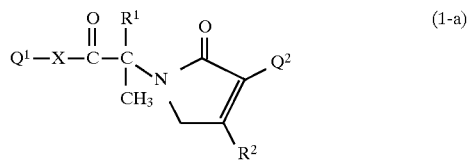

(wherein $R^1$, X and $Q^1$ are the same meanings as defined above; $R^2$ represents a $C_1$–$C_4$ alkyl group; and $Q^2$ represents an optionally substituted phenyl or thienyl group), those represented by the formula (1-b):

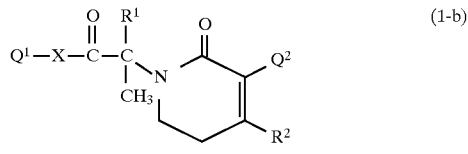

(wherein $R^1$, X and $Q^1$ are the same meanings as defined above; $R^2$ represents a $C_1$–$C_4$ alkyl group; and $Q^2$ represents an optionally substituted phenyl or thienyl group), those represented by the formula (1-c):

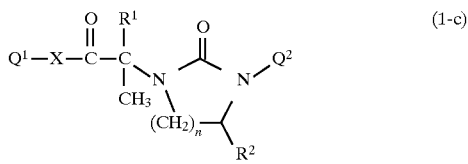

(wherein $R^1$, X and $Q^1$ are the same meanings as defined above; $R^2$ represents a hydrogen atom or a $C_1$–$C_4$ alkyl group; $Q^2$ represents an optionally substituted phenyl or thienyl group; and n represents 1 or 2), those represented by the formula (1-d):

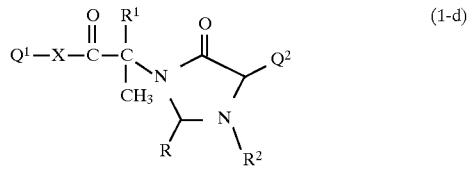

(wherein $R^1$, $R^2$, R, X, $Q^1$ and $Q^2$ are the same meanings as defined above), those represented by the formula (1-e):

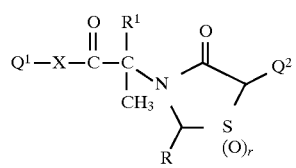
(1-e)

(wherein $R^1$, X, R and $Q^1$ are the same meanings as defined above; $Q^2$ represents an optionally substituted phenyl or thienyl group; and r represents 0, 1 or 2), and those represented by the formula (1-f):

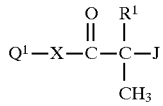
(1-f)

(wherein $R^1$, X and $Q^1$ are the same meanings as defined above; J represents

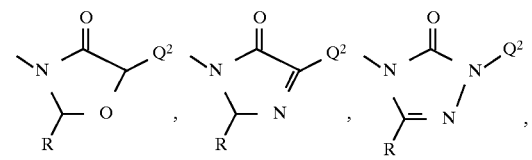

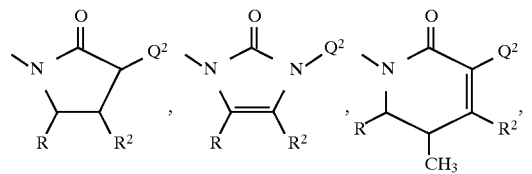

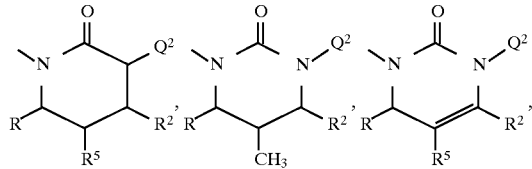

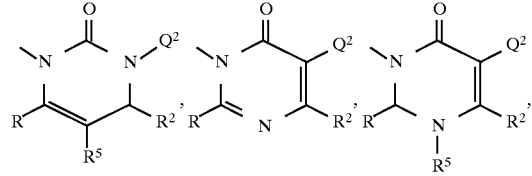

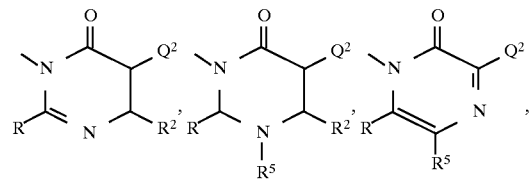

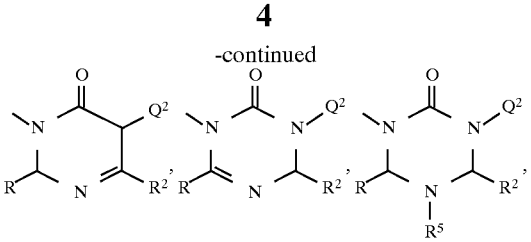

-continued or wherein $R^2$, $R^5$, R and $Q^2$ the same meanings as defined above).

Preferred substituents will be shown in the followings.

$Q^1$ is preferably a hydrogen atom, or a $C_1$–$C_6$ alkyl, $C_3$–$C_7$ $C_3$–$C_6$ alkynyl group, or

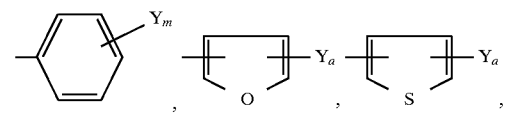

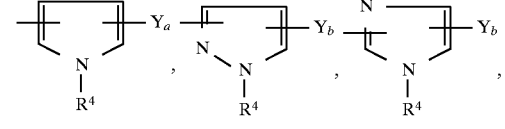

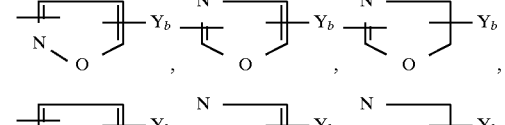

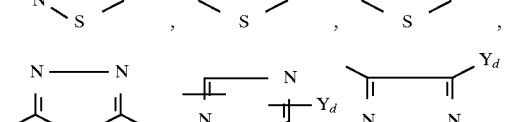

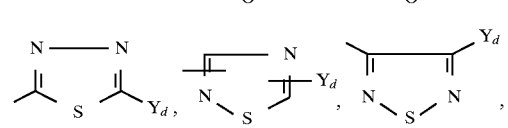

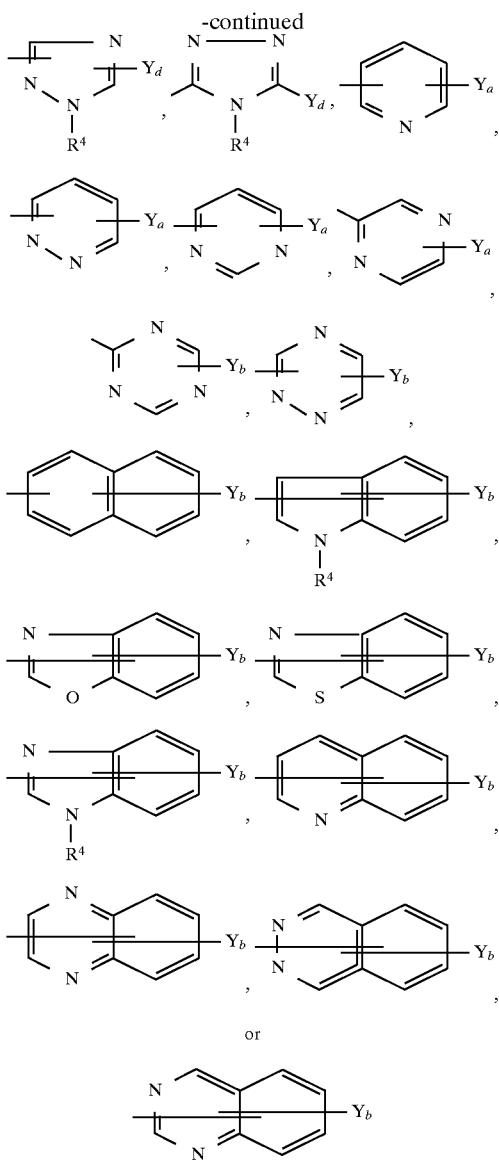

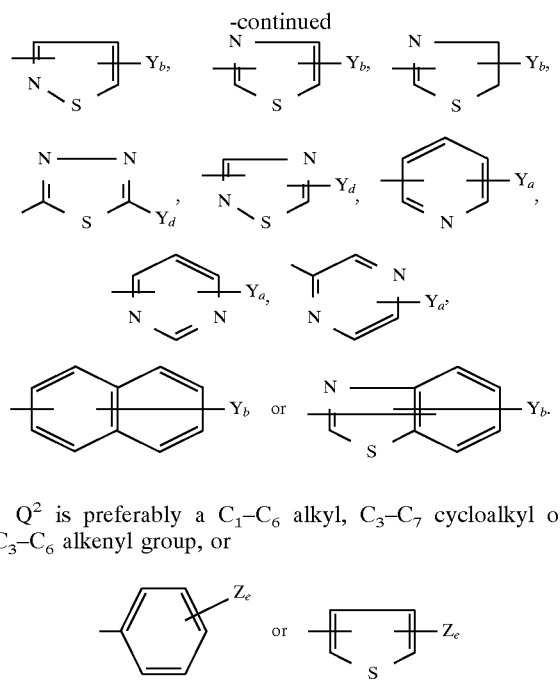

(wherein Y represents a halogen atom, or a $C_1$–$C_4$ alkyl, $C_1$–$C_4$ alkoxy, $C_1$–$C_4$ haloalkyl, $C_1$–$C_4$ haloalkoxy, $C_1$–$C_4$ alkylthio, $C_1$–$C_4$ alkylsulfinyl, $C_1$–$C_4$ alkylsulfonyl, ($C_1$–$C_4$ alkoxy)carbonyl or carboxyl group, or a nitro or cyano group; m represents an integer of 0 to 5; Y may be the same or different when m represents an integer of 2 to 5; a represents an integer of 0 to 3; Y may be the same or different when a represents 2 or 3; b represents 0, 1 or 2; Y may be the same or different when b represents 2; d represents 0 or 1; and $R^4$ represents a hydrogen atom or a $C_1$–$C_4$ alkyl group).

More preferably $Q^1$ is a hydrogen atom, a $C_1$–$C_6$ alkyl group, or any one of the following groups;

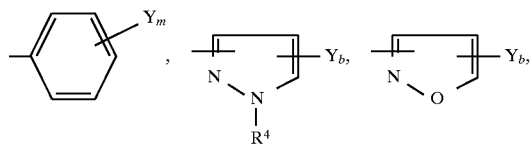

$Q^2$ is preferably a $C_1$–$C_6$ alkyl, $C_3$–$C_7$ cycloalkyl or $C_3$–$C_6$ alkenyl group, or

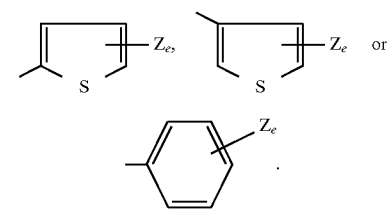

(wherein Z represents a halogen atom, or a $C_1$–$C_4$ alkyl, $C_1$–$C_4$ alkoxy, $C_1$–$C_4$ haloalkyl or $C_1$–$C_4$ haloalkoxy group; e represents an integer of 0 to 3; Z may be the same or different when e represents 2 or 3).

More preferably $Q^2$ is any one of the following groups;

The ring comprising $A^1$, $A^2$ and $A^3$ is preferably any one of the following rings;

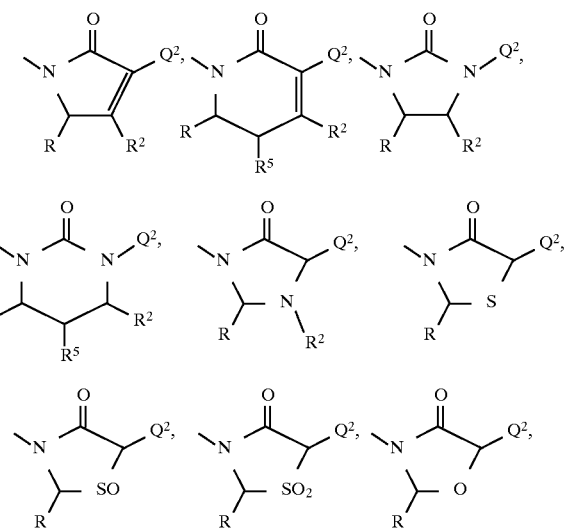

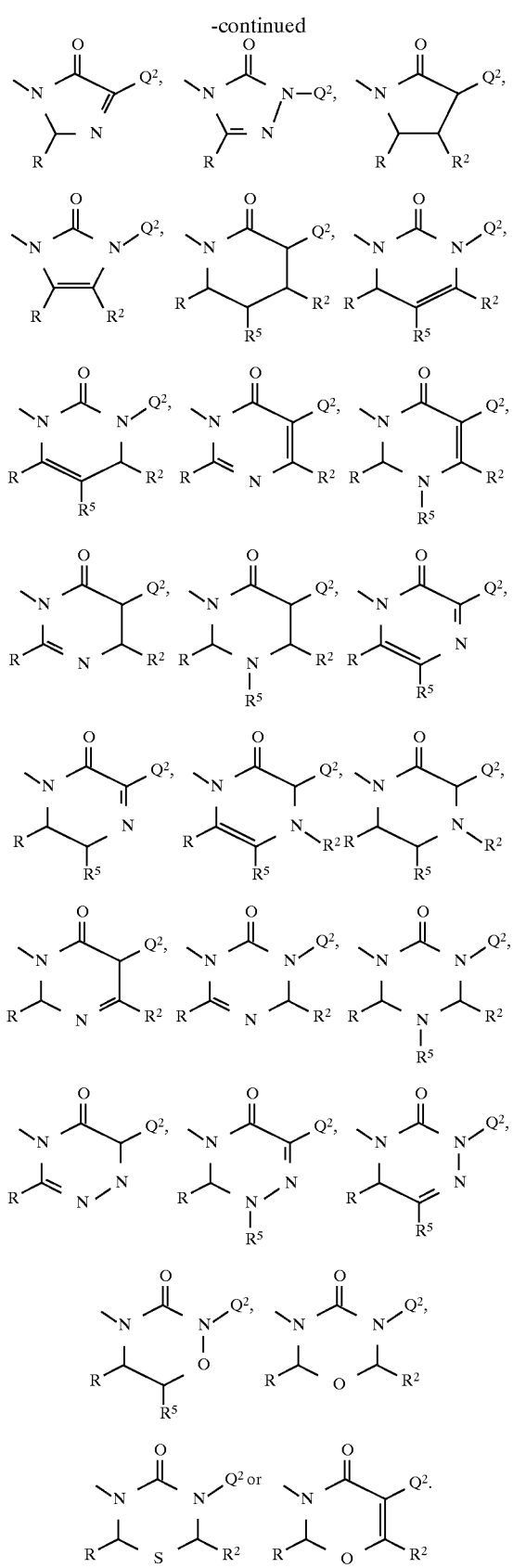

R² is preferably a hydrogen atom or a methyl or ethyl group.

R⁵ is preferably a hydrogen atom or a methyl group.
R is preferably a hydrogen atom.
R¹ is preferably a methyl group.
The substituents may be specified as follows.

Examples of Q¹ include a hydrogen atom, and methyl, ethyl, n-propyl, iso-propyl, n-butyl, iso-butyl, sec-butyl, tert-butyl, n-pentyl, iso-pentyl, 2,2-dimethylpropyl, 1-ethylpropyl, sec-pentyl, n-hexyl, allyl, 2-butenyl, 2-methyl-2-propenyl, 1-methyl-2-propenyl, 1-methyl-2-butenyl, 2-methyl-2-butenyl, 3-methyl-2-butenyl, 2-pentenyl, 2-hexenyl, propargyl, 2-butynyl, 1-methyl-2-propynyl, cyclopropyl, cyclobutyl, cyclopentyl, cyclohexyl, cycloheptyl and 4-methylcyclohexyl groups as well as the following groups;

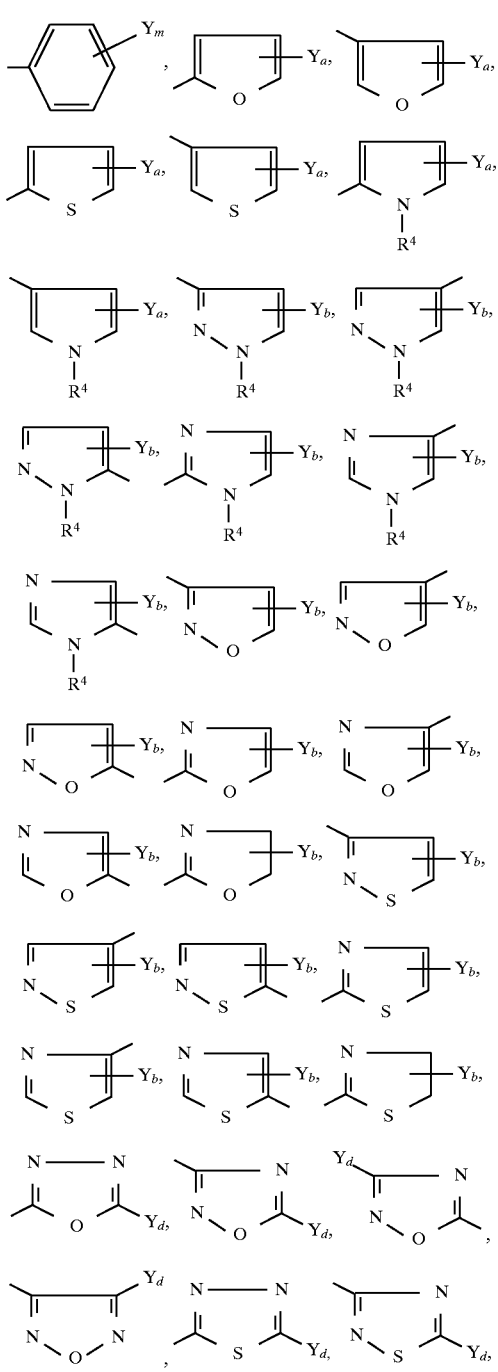

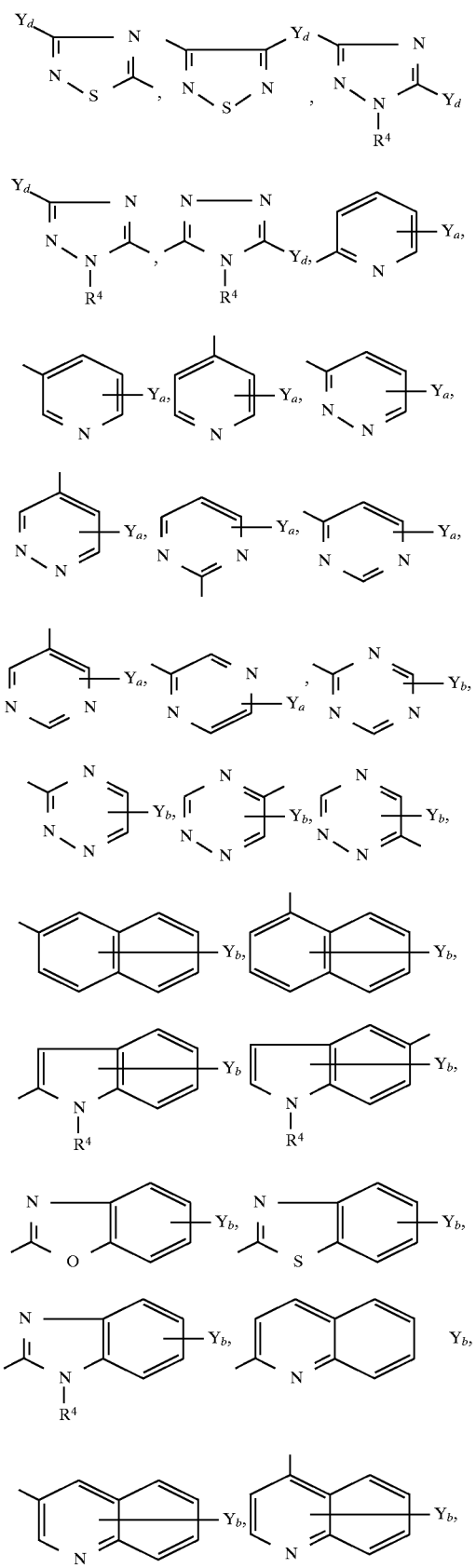

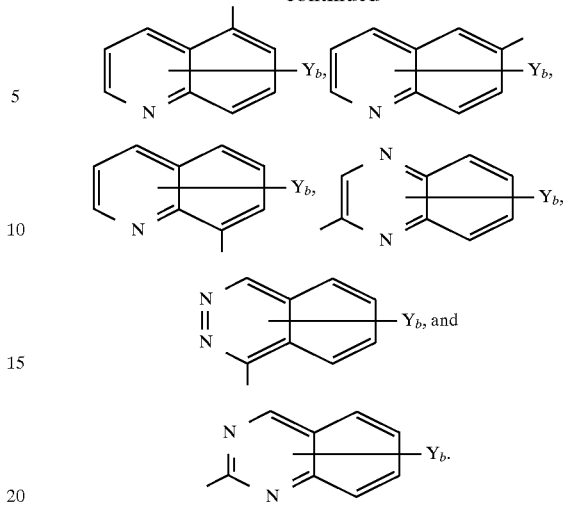

Examples of the substituent Y include fluorine, chlorine, bromine and iodine atoms, and methyl, ethyl, n-propyl, iso-propyl, n-butyl, iso-butyl, sec-butyl, tert-butyl, methoxy, ethoxy, n-propoxy, iso-propoxy, n-butoxy, iso-butoxy, sec-butoxy, tert-butoxy, difluoromethyl, trifluoromethyl, chloromethyl, bromomethyl, pentafluoroethyl, 2-chloroethyl, difluoromethoxy, trifluoromethoxy, 2,2,2-trifluoroethoxy, 2-chloroethoxy, 3-chloropropoxy, methylthio, ethylthio, n-propylthio, iso-propylthio, n-butylthio, iso-butylthio, sec-butylthio, tert-butylthio, methylsulfinyl, ethylsulfinyl, n-propylsulfinyl, iso-propylsulfinyl, n-butylsulfinyl, iso-butylsulfinyl, sec-butylsulfinyl, tert-butylsulfinyl, methylsulfonyl, ethylsulfonyl, n-propylsulfonyl, iso-propylsulfonyl, n-butylsulfonyl, iso-butylsulfonyl, sec-butylsulfonyl, tert-butylsulfonyl, nitro, methoxycarbonyl, ethoxycarbonyl, n-propoxycarbonyl, iso-propoxycarbonyl, n-butoxycarbonyl, iso-butoxycarbonyl, sec-butoxycarbonyl, tert-butoxycarbonyl, carboxyl and cyano groups.

Examples of $R^4$ include a hydrogen atom, and methyl, ethyl, n-propyl, iso-propyl, n-butyl, iso-butyl, sec-butyl and tert-butyl groups.

Examples of $Q^2$ include methyl, ethyl, n-propyl, iso-propyl, n-butyl, iso-butyl, sec-butyl, tert-butyl, n-pentyl, iso-pentyl, neo-pentyl, n-hexyl, 2-ethylbutyl, cyclopropyl, cyclobutyl, cyclopentyl, cyclohexyl, cycloheptyl, allyl, 2-butenyl, 2-methyl-2-propenyl, 1-methyl-2-propenyl and 1-methyl-2-butenyl groups as well as the following groups;

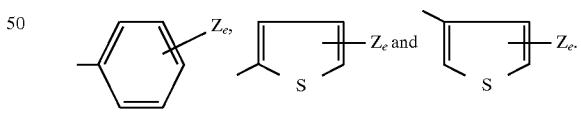

Examples of the substituent Z include fluorine, chlorine, bromine and iodine atoms, and methyl, ethyl, n-propyl, iso-propyl, n-butyl, iso-butyl, sec-butyl, tert-butyl, methoxy, ethoxy, n-propoxy, iso-propoxy, n-butoxy, iso-butoxy, sec-butoxy, tert-butoxy, difluoromethyl, trifluoromethyl, chloromethyl, bromomethyl, pentafluoroethyl, 2-chloroethyl, difluoromethoxy, trifluoromethoxy, 2,2,2-trifluoroethoxy, 2-chloroethoxy and 3-chloropropoxy groups, and preferably Z is a fluorine, chlorine, bromine or iodine atom.

Examples of $R^1$ include methyl, ethyl, n-propyl, iso-propyl, n-butyl, iso-butyl, sec-butyl and tert-butyl groups, and preferably $R^1$ is a methyl group.

Examples of R include a hydrogen atom, and methyl, ethyl, n-propyl, iso-propyl, n-butyl, iso-butyl, sec-butyl and tert-butyl groups, and preferably R is a hydrogen atom.

Examples of X include oxygen and sulfur atoms, and NH and $NCH_3$, and preferably X is an oxygen atom or NH.

Examples of $R^2$ include a hydrogen atom, and methyl, ethyl, n-propyl, iso-propyl, n-butyl, iso-butyl, sec-butyl, tert-butyl, allyl, 2-butenyl, 2-methyl-2-propenyl, 1-methyl-2-propenyl, 1-methyl-2-butenyl, 2-methyl-2-butenyl, 3-methyl-2-butenyl, 2-pentenyl, 2-hexenyl, propargyl, 2-butynyl and 1-methyl-2-propynyl groups, and preferably $R^2$ is a hydrogen atom or a methyl or ethyl group.

Examples of $R^5$ include a hydrogen atom, and methyl, ethyl, n-propyl, iso-propyl, n-butyl, iso-butyl, sec-butyl and tert-butyl groups, and preferably $R^5$ is a hydrogen atom or a methyl group.

The compounds of the present invention can be applied as a herbicide for upland field, paddy field and non-arable land through either soil treatment or foliage treatment. Also, they show high herbicidal activities at a low dosage against, for instance, broad-leaved weeds such as *Solanum nigrum, Datura stramonium, Abutilon theophrasti, Sida spinosa, Ipomoea purpurea, Amaranthus lividus, Amaranthus retroflexus, Xanthium pensylvanicum, Ambrosia artemisiaefolia, Helianthus annuus, Galinsoga ciliata, Cirsium arvense, Senecio vulgaris, Erigeron annuus, Rorippa indica, Sinapis arvensis, Capsella Bursa-pastoris, Polygonum Blumei, Polygonum convolvulus, Portulaca oleracea, Chenopodium album, Chenopoclium ficifolium, Kochias coparia, Stellaria media, Veronica persica, Commelina communis, Lamium amplexicaule, Lamium purpureum, Euphorbia supina, Euphorbia maculata, Galium aparine, Rubia akane, Viola arvensis, Sesbania exaltata, Cassia obtusifolia, Bidens pilosa*; Graminaceous weeds such as *Sorghum bicolor, Panicum dichotomiflorum, Sorghum halepense, Echinochloa crus-galli, Digitaria adscendens, Avena fatua, Eleusine indica, Setaria viridis, Alopecurus aegualis*; Cyperaceous weeds such as *Cyperus rotundus*; various paddy weeds such as *Alisma canaliculatum, Sagittaria trifolia, Sagittaria pygmaea, Cyrerus difformis, Cyperus serotinus, Scirpus juncoides, Eleocharis kuroguwai, Lindernia pyxidaria, Monochoria vaginalis, Potamogeton distinctus, Rotala indica, Echinochloa crus-galli*. The compounds of the present invention include compounds which do no harm to the important crops such as wheat, corn, barley, soybean, rice, cotton, sugar beet and sorghum.

Further, the compounds of the present invention are also useful as a defoliant.

The compounds of the present invention can be, for example, synthesized through the processes illustrated in Schemes 1-1 to 4-1, wherein $Q^1$, $Q^2$, $R^1$, $R^2$, R, X, r and n are the same meanings as defined above; $Hal^1$ and $Hal^2$ represent independently halogen atoms; A represents a $C_1$–$C_6$ alkyl group or a phenyl group; and f represents 1 or 2.

Scheme 1-1

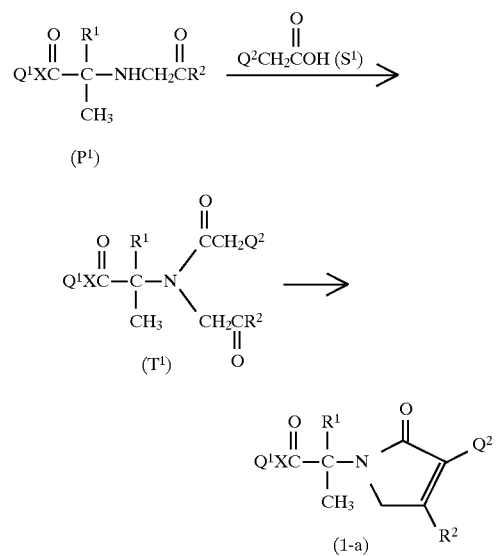

Scheme 1-2

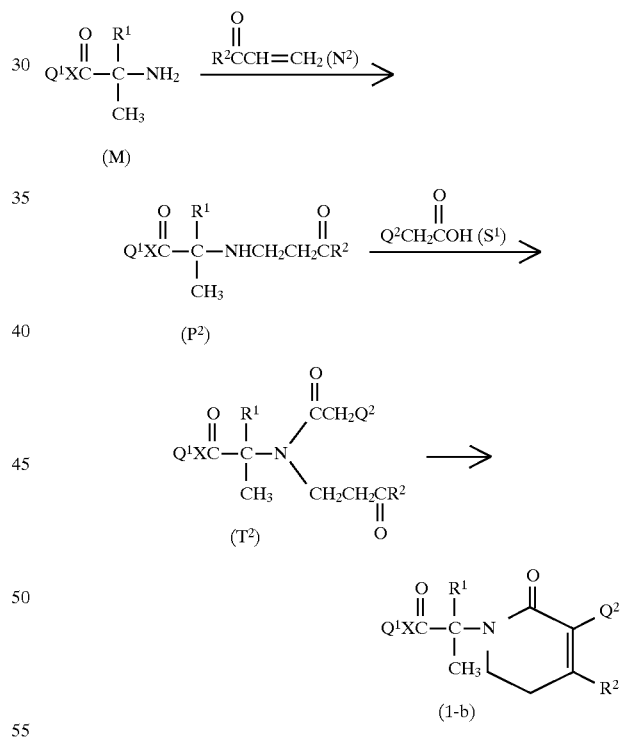

Scheme 1-3

13

-continued
Scheme 1-3

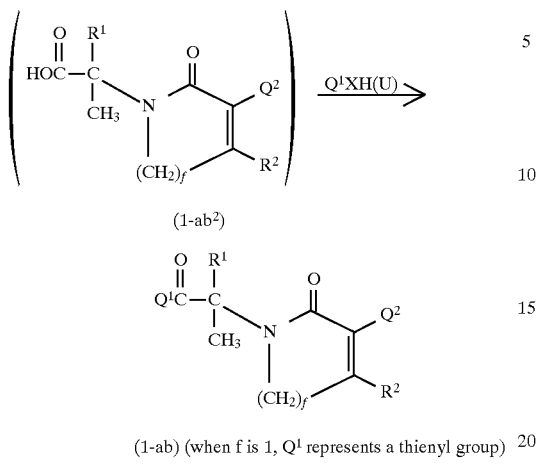

(1-ab) (when f is 1, $Q^1$ represents a thienyl group)

A) Scheme 1-1 illustrates a process for preparing a compound of the present invention (1-a), which comprises reacting 2-aminoisobutyric acid derivative (M) with σ-halogenoketone derivative ($N^1$) to prepare an intermediate ($p^1$), reacting the intermediate ($p^1$) with reactive acetic acid derivative ($S^1$) to form an amide compound ($T^1$) and cyclizing the amide compound ($T^1$) to give the compound (1-a)

B) Scheme 1-2 illustrates a process for preparing a compound of the present invention (1-b), which comprises reacting 2-aminoisobutyric acid derivative (M) with vinylketone derivative ($N^2$) to prepare an intermediate ($p^2$), reacting the intermediate ($P^2$) with reactive acetic acid derivative ($S^1$) to form an amide compound ($T^2$) and cyclizing the amide compound ($T^2$) to give the compound (1-b).

C) Scheme 1-3 illustrates a process for preparing a compound of the present invention (1-ab), which comprises hydrolyzing the ester derivative (1-ab$^1$) prepared according to Scheme 1-1 or 1-2 to form an acid (1-ab$^2$) and converting the acid (1-ab$^2$) into a reactive compound which is then reacted with $Q^1XH(U)$ to give the compound (1-ab), and one which comprises direct transesterification of the ester (1-ab$^1$) with $Q^1XH(u)$ or amidation of the ester via amine degradation to give the compound (1-ab).

Scheme 2-1

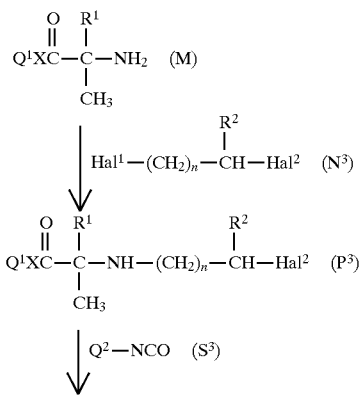

14

-continued
Scheme 2-1

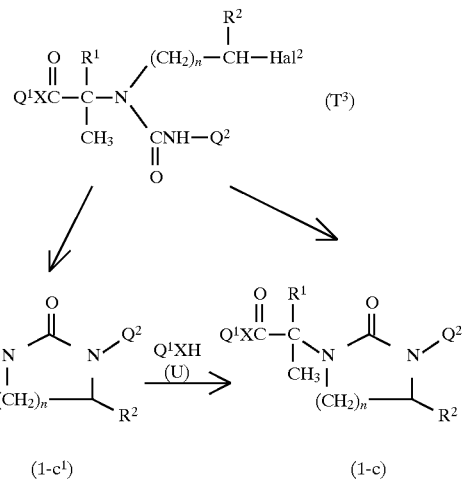

D) Scheme 2-1 illustrates a process for preparing a compound of the present invention (1-c), which comprises reacting 2-aminoisobutyric acid derivative (M) with alkyl dihalide ($N^3$) to prepare an intermediate ($P^3$), reacting the intermediate ($P^3$) with isocyanic ester derivative ($S^3$) to form an urea compound ($T^3$), cyclizing and simultaneously hydrolyzing the urea compound ($T^3$) to prepare an acid (1-c$^1$) and then converting the acid (1-c$^1$) into a reactive compound which is then reacted with $Q^1XH(U)$ to give the compound (1-c), and one which comprises cyclizing the urea compound ($T^3$) without hydrolyzation to give the compound (1-c).

Scheme 3-1

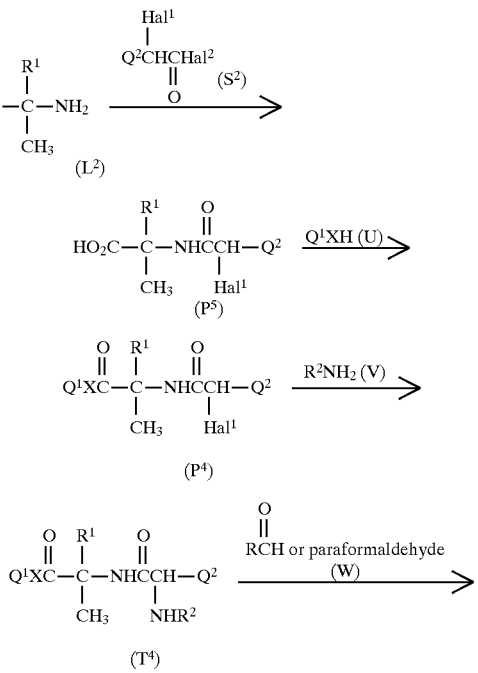

Scheme 3-1 -continued

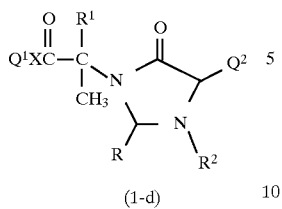

Scheme 3-3 -continued

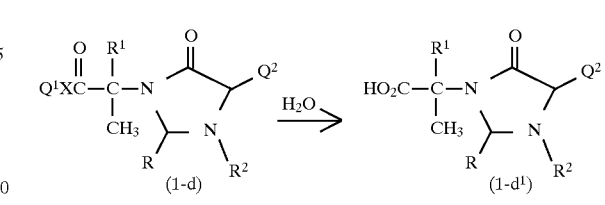

E) Scheme 3-1 illustrates a process for preparing a compound of the present invention (1-d), which comprises reacting σ-amino acid ($L^2$) with σ-halogeno-acid halide ($S^2$) to prepare an amide compound ($P^5$), reacting the amide compound ($P^5$) with $Q^1XH$(U) to form an intermediate ($P^4$), reacting the intermediate ($P^4$) with amine (V) to obtain an σ-aminoamide compound ($T^4$) and then cyclizing the σ-aminoamide compound ($T^4$) with aldehyde (W) to give the compound (1-d).

F) Scheme 3-2 illustrates a process for preparing a compound of the present invention (1-d), which comprises reacting the intermediate amide compound ($P^5$) prepared according to Scheme 3-1 with amine (V) to prepare an σ-aminoamide compound ($T^5$), reacting the σ-aminoamide compound ($T^5$) with aldehyde (W) to form an imidazolidinone (1-$d^1$) and then reacting the imidazolidinone (1-$d^1$) with $Q^1XH$(U) to give the compound (1-d).

G) Scheme 3-3 illustrates a process for preparing a compound of the present invention (1-d), which comprises reacting σ-amino acid ($L^2$) with $Q^1XH$(U) to prepare an 2-aminoisobutyric acid derivative (M), reacting the 2-aminoisobutyric acid derivative (M) with σ-halogeno-acid halide ($S^2$) to form an intermediate ($P^4$) and then performing a similar procedure to that in Scheme 3-1 to give the compound (1-d), and a process for preparing a compound of the present invention (1-$d^1$) which is an imidazolidinone derivative, comprising hydrolyzing the compound (1-d).

Scheme 3-2

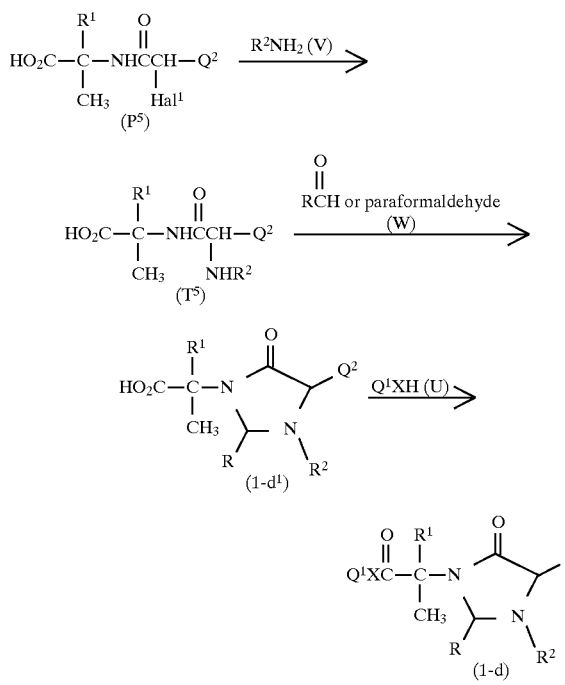

Scheme 3-3

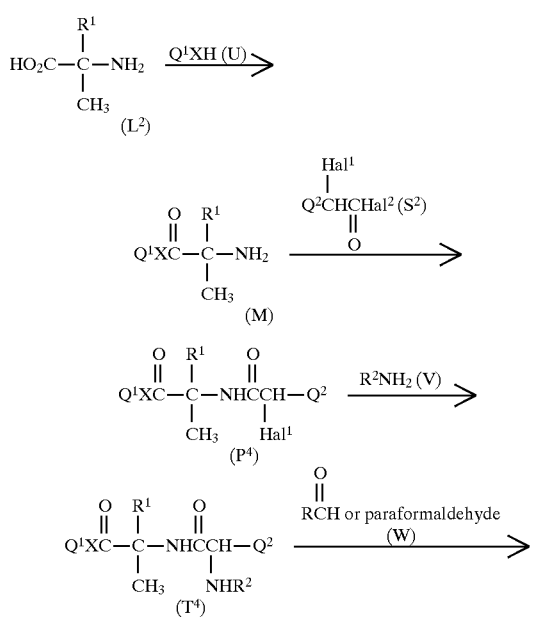

Scheme 4-1

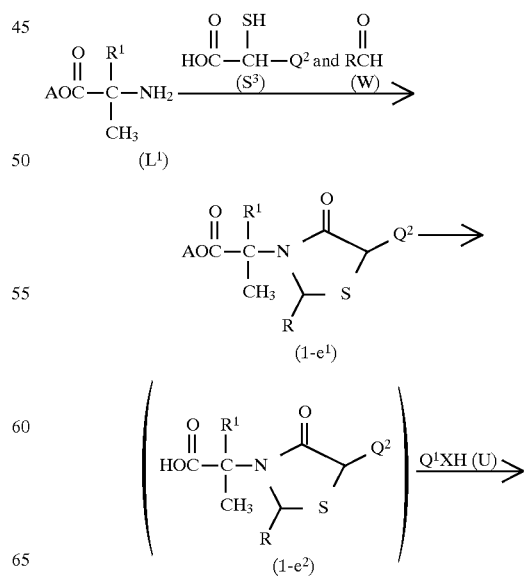

-continued
Scheme 4-1

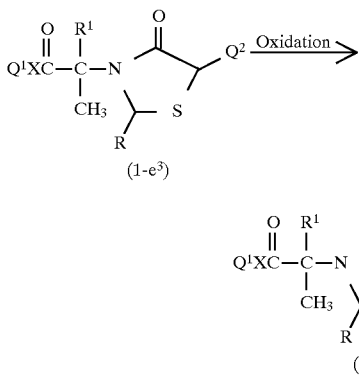

(wherein r represents 1 or 2)

H) Scheme 4-1 illustrates a process for preparing a compound of the present invention (1-e³), which comprises reacting 2-aminoisobutyric ester (L¹) with σ-mercaptoacetic acid derivative (S³) and aldehyde (W) to prepare an acid-ester derivative of thiazolidinone (1-e¹), hydrolyzing the acid-ester derivative of thiazolidinone (1-e¹) to form an acid (1-e²) and converting the acid (1-e²) into a reactive compound which is then reacted with Q¹XH(U) to give the compound (1-e³), and one which comprises direct transesterification of the acid-ester derivative of thiazolidinone (1-e¹) with Q¹XH(U) or amidation of the acid-ester derivative via amine degradation to give the compound (1-e³), as well as a process for preparing an S-oxidized thiazolidinone derivative (1-e), one of the compounds of the present invention, comprising oxidation of a compound of the present invention (1-e³).

A compound of the present invention can be, if necessary, separated and purified by any purification method such as recrystallization, column chromatography, etc.

When a compound according to the present invention has an asymmetric carbon atom, both the optical active isomers, i.e. (+)-isomer and (−)-isomer, are included within the present invention.

The following Examples specifically illustrate a process for preparing the compound of the present invention. However, it should be recognized that the scope of the present invention is not limited to these Examples.

EXAMPLE 1

Preparation of N-(2,5-dichlorophenyl)-2-(4-methyl--2-oxo-3-phenyl-1,2,5,6-tetrahydropyridin-1-yl)isobutyramide (Compound No. A-8)

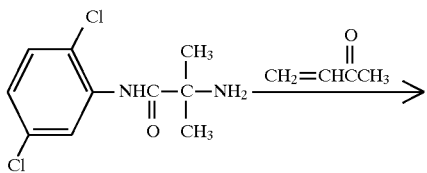

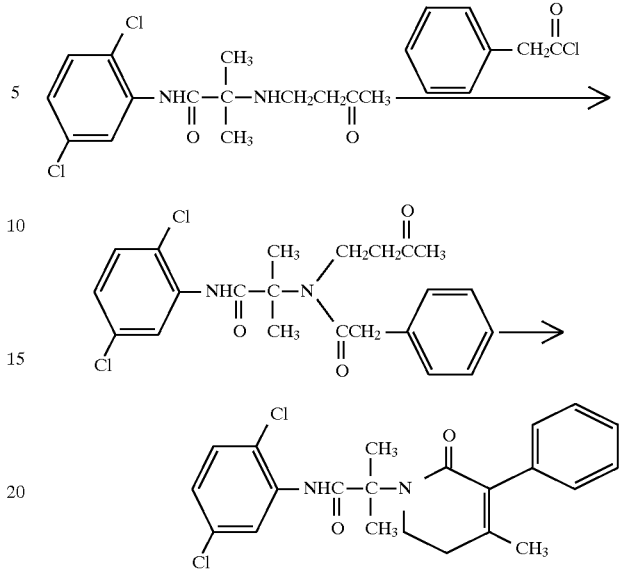

(1) Methyl vinyl ketone (1.02 g) was added to a solution of N-(2,5-dichlorophenyl)-2-aminoisobutyramide (2.4 g) in tetrahydrofuran (10 mL) and the mixture was heated at reflux for 30 hours. After distilling off the solvent under reduced pressure, 3 g of N-(2,5-dichlorophenyl)-2-(3-oxobutylamino)isobutyramide was obtained.

(2) Triethylamine (1.05 g) was added to a solution of N-(2,5-dichlorophenyl)-2-(3-oxobutylamino)isobutyramide (3.0 g) in acetone (20 mL). To the solution was added dropwise phenylacetyl chloride (1.61 g) under ice-cooling. After adding dropwise, it was stirred for 24 hours at room temperature. After distilling off the solvent, water was added to the residue, which was extracted with ethyl acetate, washed with diluted hydrochloric acid and then a saturated sodium hydrogencarbonate aqueous solution, dried over anhydrous sodium sulfate. After distilling off ethyl acetate under reduced pressure, 2.2 g of N-(2,5-dichlorophenyl)-2-[N'-(3-oxobutyl) phenylacetoamino]isobutyramide was obtained.

(3) To a solution of N-(2,5-dichlorophenyl)-2-[N'-(3-oxobutyl)phenylacetoamino]isobutyramide (2.2 g) in absolute ethanol (20 mL) was added 95% sodium methoxide (0.31 g), and the mixture was heated at reflux for 1 hour. After distilling off ethanol, water was added to the residue, which was extracted with ethyl acetate. The extract was sequentially washed with diluted hydrochloric acid, a saturated sodium hydrogencarbonate aqueous solution and a saturated sodium chloride aqueous solution, and dried over anhydrous sodium sulfate. After distilling off ethyl acetate under reduced pressure, the resulting crude product was purified by preparative thin-layer chromatography (developing solvent: chloroform/ethyl acetate=10/1) to obtain 0.13 g of the title compound.

EXAMPLE 2

Preparation of N-(2.5-dichlorophenyl)-2-[4-methyl-2-oxo-3-(thiophen-3-yl)-3-pyrrolin-1-yl]isobutyramide (Compound No. A-2)

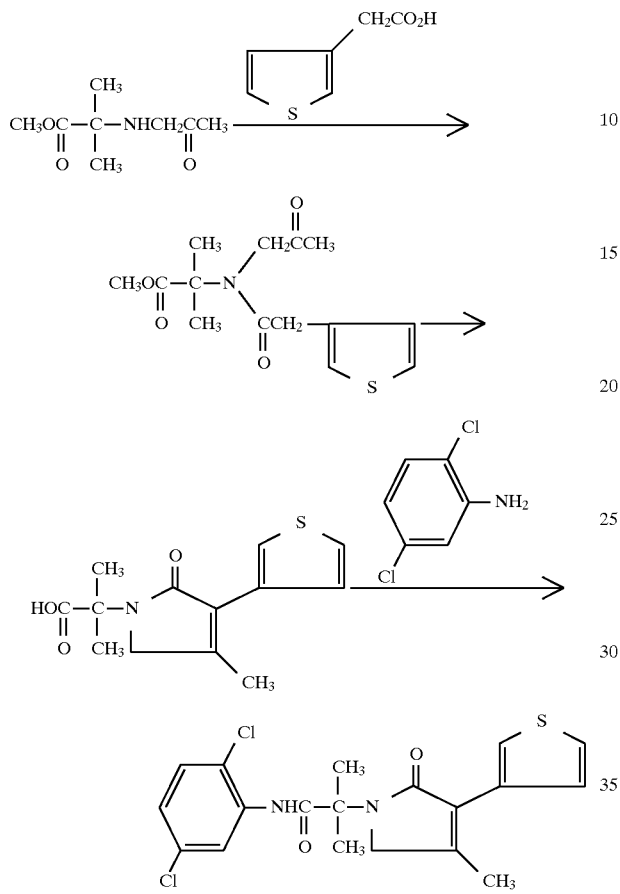

(1) To a solution of thiophen-3-acetic acid (8.7 g) in dichloromethane (70 mL) was added 1-(3-dimethylaminopropyl)-3-ethylcarbodiimide hydrochloride (11.7 g), and the mixture was stirred for 10 minutes at room temperature. To the solution was added dropwise a solution of methyl 2-(2-oxopropylamino)isobutyrate (10.6 g) in dichloromethane (10 mL) at room temperature, and the mixture was then stirred for 24 hours at room temperature. After distilling off the solvent, water was added, and then the mixture was extracted with ethyl acetate. The extract was washed with a saturated sodium hydrogencarbonate aqueous solution and dried over anhydrous sodium sulfate. After distilling off ethyl acetate, 7.61 g of methyl 2-[N-(2-oxopropyl)thiophene-3-yl-acetylamino]isobutyrate was obtained.

(2) To a solution of methyl 2-[N-(2-oxopropyl)thiophene-3-yl-acetylamino]isobutyrate (7.6 g) in absolute ethanol (50 mL) was added 95% sodium methoxide (1.6 g), and the mixture was heated at reflux for 30 minutes. To the solution were added water (3.5 mL) and 85% potassium hydroxide (0.88 g), and the mixture was heated at reflux for 1 hour. After distilling off the solvent, the residue was poured into ice-water and washed with diethyl ether. It was adjusted to pH 2–3 with concentrated hydrochloric acid and the precipitated crystals were filtered, washed with water and dried to give 4.47 g of 2-[4-methyl-2-oxo-3-(thiophen-3-yl)-3-pyrrolin-1-yl]isobutyric acid.

(3) Triphenylphosphine (1.3 g) was added to a suspension of 2-[4-methyl-2-oxo-3-(thiophen-3-yl)-3-pyrrolin-1-yl]isobutyric acid (1 g) in carbon tetrachloride (9 mL) and dichloromethane (9 mL), and the mixture was heated at reflux for 30 minutes at 70° C. After ice-cooling the reaction solution, 2,5-dichloroaniline (0.61 g) and then triethylamine (0.38 g) were added, and the mixture was stirred for 24 hours at room temperature. After the reaction was completed, distilling off the solvent, water was added and the resulting mixture was extracted with ethyl acetate. The extract was washed with diluted hydrochloric acid and a saturated sodium hydrogencarbonate aqueous solution, and dried over anhydrous sodium sulfate. After distilling off ethyl acetate, the resulting crude product was purified by preparative thin-layer chromatography (developing solvent: chloroform/ethyl acetate=20/1) to give 0.35 g of the title compound.

EXAMPLE 3

Preparation of 2-(3-phenyl-tetrahydro-2-pyrimidon-1-yl)isobutyric acid (Compound No. B-1)

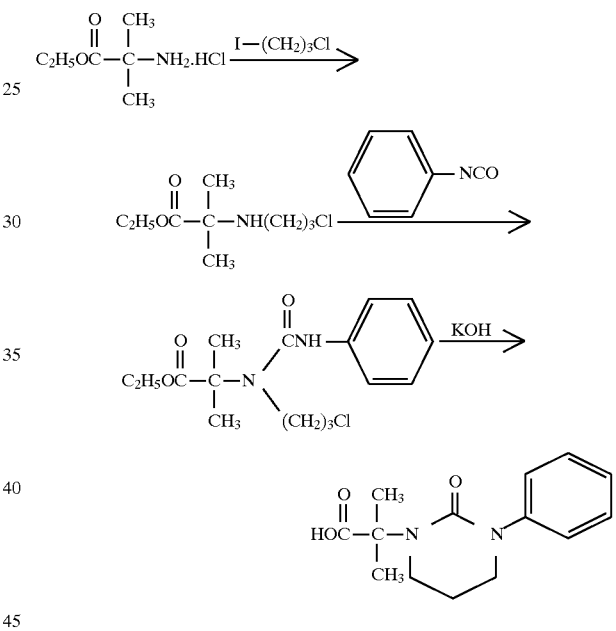

(1) A solution of ethyl aminoisobutyrate hydrochloride (10 g) in DMF (50 mL) was cooled to 0° C. To the solution were added potassium carbonate (18 g) and 1-chloro-3-iodopropane (12 g), and the mixture was stirred overnight at 0° C. to room temperature. Water was added to the reaction solution and the mixture was extracted with ethyl acetate. The organic layer was washed with water and dried over anhydrous sodium sulfate. The solvent was distilled off under reduced pressure to give 12.5 g of crude ethyl 2-(3-chloropropylamino)isobutyrate.

(2) Phenyl isocyanate (2.8 g) was added to a solution of the above crude ethyl 2-(3-chloropropylamino)isobutyrate (5 g) in toluene (30 mL) which was cooled to 0° C., and the mixture was stirred overnight at 0° C. to room temperature. After adding water, the reaction solution was extracted with ethyl acetate. The organic layer was washed with water, dried over anhydrous sodium sulfate, and the solvent was distilled off under reduced pressure to give 7.4 g of crude ethyl 2-[3-phenyl-1-(3-chloropropyl)ureido]isobutyrate.

(3) Powdered potassium hydroxide (1.3 g) was added to a solution of the above obtained crude ethyl 2-[3-phenyl-1-

(3-chloropropyl)ureido]isobutyrate (7.4 g) in ethanol (30 mL), and the mixture was heated at reflux for 30 minutes. After concentrated under reduced pressure, water was added and the mixture was washed with diethyl ether.

The aqueous layer was acidified with concentrated hydrochloric acid and extracted with ethyl acetate. The organic layer was washed with water and dried over anhydrous sodium sulfate, and then the solvent was distilled off under reduced pressure. The resulting crude product was washed with diisopropyl ether to give 1.8 g of 2-(3-phenyl-tetrahydro-2-pyrimidon-1-yl)isobutyric acid.

EXAMPLE 4

Preparation of N-(5-chlorothiazolyl) 2-(3-phenyl-tetrahydro-2-pyrimidon-1-yl)isobutyramide (Compound No. B-4)

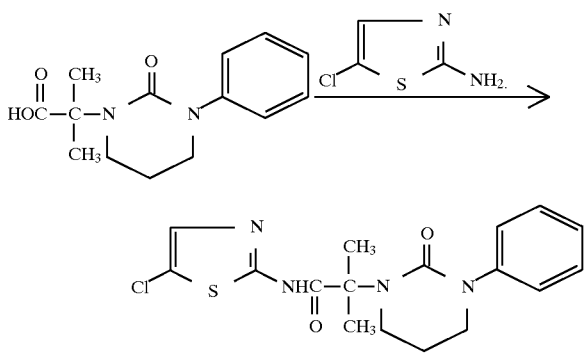

A solution of 2-(3-phenyl-tetrahydro-2-pyrimidon-1-yl) isobutyric acid (0.5 g) prepared according to Example 3 in dichloromethane (20 mL) was cooled to 0° C. To the solution were added 4-dimethylaminopyridine (50 mg) and 1-(3-dimethylaminopropyl)-3-ethylcarbodiimide hydrochloride (0.5 g), and the mixture was stirred for 10 minutes at 0° C. to room temperature. To the solution were then added 4-dimethylaminopyridine (0.3 g) and 2-amino-5-chlorothiazole hydrochloride (0.4 g), and the mixture was stirred overnight at room temperature. After adding acidic water whose pH was about 2, the mixture was extracted with chloroform. The organic layer was washed with water and dried over anhydrous sodium sulfate, and the solvent was distilled off under reduced pressure. The resulting crude product was washed with diisopropyl ether to give 0.47 g of N-(5-chlorothiazolyl) 2-(3-phenyl-tetrahydro-2-pyrimidon-1-yl)isobutyramide.

EXAMPLE 5

Preparation of 2-[3-(2-fluorophenyl)-tetrahydro-2-pyrimidon-1-yl]isobutyric acid (Compound No. B-5)

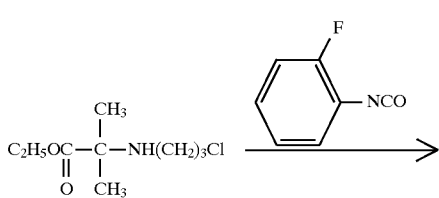

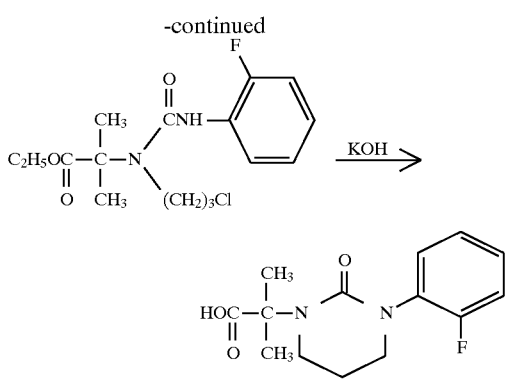

(1) A solution of ethyl 2-(3-chloropropylamino) isobutyrate (7.5 g) prepared according to Example 3-(1) in toluene (45 mL) was cooled to 0° C. To the solution was added 2-fluoropheyl isocyanate (5 g), and the mixture was stirred overnight at 0° C. to room temperature. Water was added to the reaction solution and the resulting mixture was extracted with ethyl acetate. The organic layer was washed with water and dried over anhydrous sodium sulfate. The solvent was distilled off under reduced pressure to give 10.9 g of crude ethyl 2-[3-(2-fluorophenyl)-1-(3-chloropropyl) ureido]isobutyrate.

(2) Powdered potassium hydroxide (1.8 g) was added to a solution of the above obtained crude ethyl 2-[3-(2-fluorophenyl)-1-(3-chloropropyl)ureido]isobutyrate (10.9 g) in ethanol (30 mL), and the mixture was heated at reflux for 30 minutes. After the mixture was concentrated under reduced pressure and water was added, the resulting mixture was washed with diethyl ether. The aqueous layer was acidified with concentrated hydrochloric acid and then extracted with ethyl acetate. The organic layer was washed with water and dried over anhydrous sodium sulfate. After distilling off the solvent under reduced pressure, the resulting crude product was washed with diisopropyl ether to give 2.8 g of 2-[3-(2-fluorophenyl)-tetrahydro-2-pyrimidon-1-yl] isobutyric acid.

EXAMPLE 6

Preparation of N-(3,5-dichlorophenyl) 2-[3-(2-fluorophenyl)-tetrahydro-2-pyrimidon-1-yl] isobutyramide (Compound No. B-6)

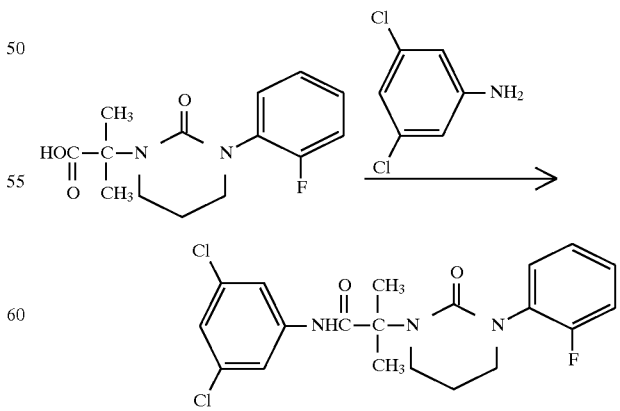

A solution of 2-[3-(2-fluorophenyl)-tetrahydro-2-pyrimidon-1-yl]isobutyric acid (0.6 g) prepared according to Example 5 in dichloromethane (20 mL) was cooled to 0° C., to which were added 4-dimethylaminopyrimidine (50 mg) and 1-(3-dimethylaminopropyl)-3-ethylcarbodiimide hydrochloride (0.5 g). The mixture was stirred for 10 minutes at 0° C. to room temperature. To the mixture was added 3,5-dichloroaniline (0.4 g), and the mixture was stirred overnight at room temperature. After adding water whose pH was about 2, the mixture was extracted with chloroform. The organic layer was washed with water and dried over anhydrous sodium sulfate. After distilling off the solvent under reduced pressure, the resulting crude product was isolated by thin-layer chromatography (SiO$_2$, developing solvent: ethyl acetate/n-hexane=5/4), which was then washed with diisopropyl ether to give 0.58 g of N-(3,5-dichlorophenyl) 2-[3-(2-fluorophenyl)-tetrahydro-2-pyrimidon-1-yl]isobutyramide.

EXAMPLE 7

Preparation of ethyl 2-(1-ethyl-5-phenylimidazolidin-4-on-3-yl)isobutyrate (Compound No. C-2)

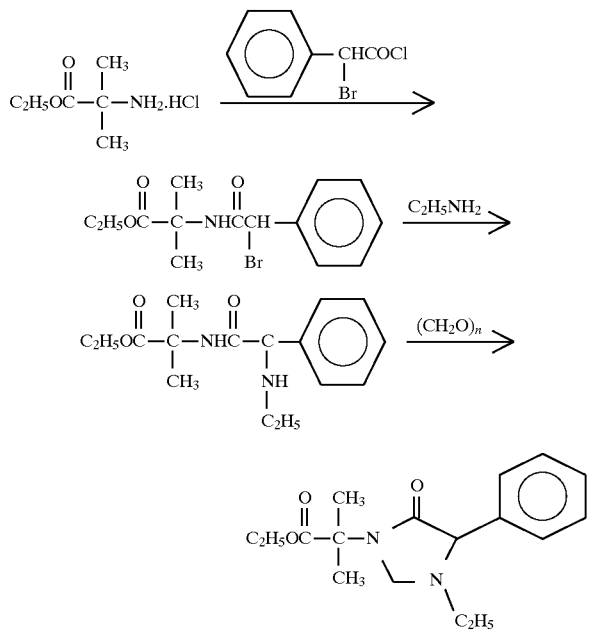

(1) Triethylamine (11 g) was added to a suspension of ethyl aminoisobutyrate (7.5 g) in acetonitrile (80 mL) cooled to 0° C., and to the mixture was slowly added dropwise a solution of o-bromophenylacetyl chloride (11g) in acetonitrile (20 mL). After the addition was completed, the solution was warmed to room temperature, and stirred overnight. The reaction solution was poured into a sodium hydrogencarbonate aqueous solution and the mixture was extracted with ethyl acetate. The organic layer was washed with water, dried over anhydrous sodium sulfate and concentrated under reduced pressure, and then the resulting crude product was washed with diisopropyl ether to give 6.4 g of ethyl 2-(o-bromophenylacetylamino)isobutyrate.

$^1$H-NMR[CDCl$_3$]: 1.22 (3H, t, J=7 Hz), 1.58 (6H, s), 4.18 (2H, q, J=7 Hz), 5.38 (1H, s), 7.31–7.60 (5H, m).

m.p.: 81°–83° C.

(2) To a suspension of ethyl 2-(o-bromophenylacetylamino) isobutyrate (6.3 g) in ethanol (30 mL) was added a 70% ethylamine aqueous solution (20 g) at room temperature, and the mixture was stirred overnight. After the mixture was concentrated under reduced pressure, water was added, and then the mixture was acidified with concentrated hydrochloric acid and extracted with diethyl ether. After separating the extract, the aqueous layer was basified with sodium hydrogencarbonate and extracted with ethyl acetate. The organic layer was washed with water and dried over anhydrous sodium sulfate. The solvent was distilled off under reduced pressure to give 4.4 g of ethyl 2-(o-ethylaminophenylacetylamino)isobutyrate as viscous liquid.

$^1$H-NMR[CDCl$_3$]: 1.14 (3H, t, J=7 Hz), 1.17 (3H, t, J=7 Hz), 1.53 (6H, s), 1.92 (1H, s), 2.70 (2H, q, J=7 Hz), 4.13 (2H, q, J=7 Hz), 4.11 (1H, s), 7.32 (5H, s), 7.95 (1H, brs).

(3) To a solution of ethyl 2-(o-ethylaminophenylacetylamino) isobutyrate (4 g) in ethanol (30 mL) were added potassium carbonate (1.5 g) and paraformaldehyde (0.6 g), and the mixture was heated at reflux for 3 hours. The reaction solution was added to water and the mixture was extracted with ethyl acetate. The organic layer was washed with water and dried over anhydrous sodium sulfate. After distilling off the solvent under reduced pressure, the resulting crude product was purified by column (silica gel, diethyl ether/n-hexane=2/1) to give 3.8 g of the title compound.

EXAMPLE 8

Preparation of 2-(1-ethyl-5-phenylimidazolidin-4-on-3-yl)isobutyric acid (Compound No. C-3)

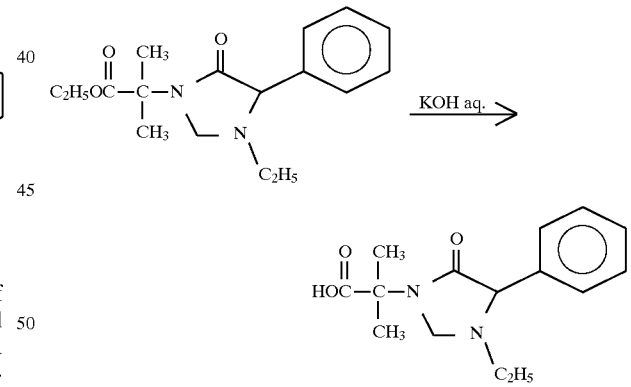

To ethyl 2-(1-ethyl-5-phenylimidazolidin-4-on-3-yl) isobutyrate (3.8 g) prepared according to Example 7 was added a 15% potassium hydroxide aqueous solution (10 mL), and the mixture was heated at reflux for 1 hour. After cooling, the mixture was extracted with diethyl ether. After separating the extract, the aqueous layer was acidified with concentrated hydrochloric acid and extracted with ethyl acetate. The organic layer was washed with water and dried over anhydrous sodium sulfate. After distilling off the solvent under reduced pressure, the resulting crude product was washed with diisopropyl ether to give 2.2 g of the title compound.

EXAMPLE 9

Preparation of N-(2,3-dichlorophenyl)-2-(1-ethyl-5-phenylimidazolidin-4-on-3-yl)isobutyramide
(Compound No. C-20)

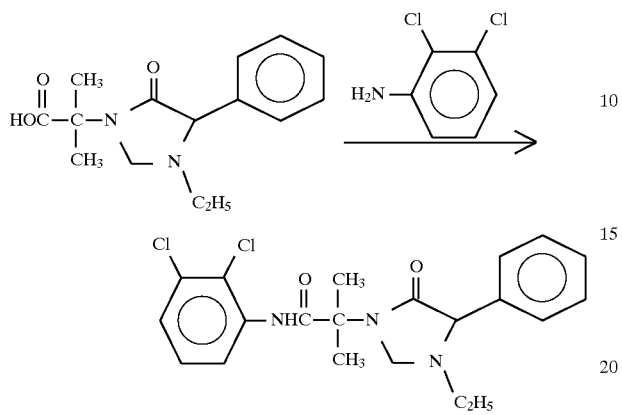

Dimethylaminopyridine (50 mg) and dimethylaminopropylethylcarbodiimide hydrochloride (0.5 g) were added to a solution of 2-(1-ethyl-5-phenylimidazolidin-4-on-3-yl)isobutyric acid (0.6 g) prepared according to Example 8 in dichloromethane (15 mL) at 0° C. After stirring for 15 minutes at 0° C. to room temperature, 2,3-dichloroaniline (0.4 g) was added and the mixture was stirred overnight at room temperature. The reaction solution was poured into water whose pH was 2, and the mixture was extracted with chloroform. The organic layer was washed with water and dried over anhydrous sodium sulfate. After distilling off the solvent under reduced pressure, the resulting crude product was purified by thin-layer chromatography (silica gel, ethyl acetate/n-hexane=2/3) to give 0.2 g of the title compound.

EXAMPLE 10

Preparation of N-(2,5-dichlorophenyl)-2-(1-ethyl-5-phenylimidazolidin-4-on-3-yl)isobutyramide
(Compound No. C-1)

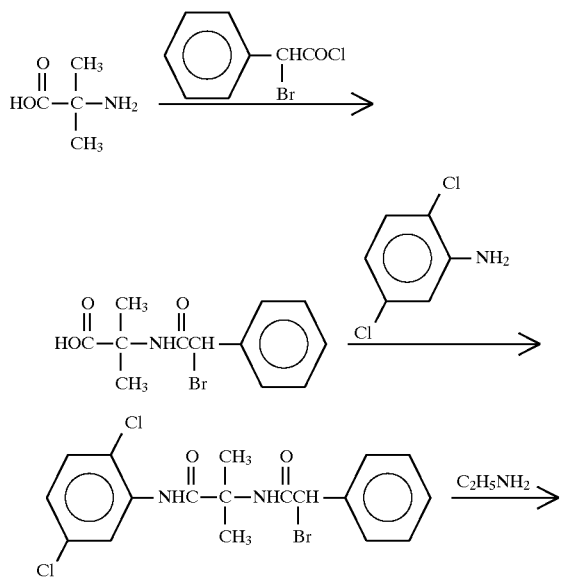

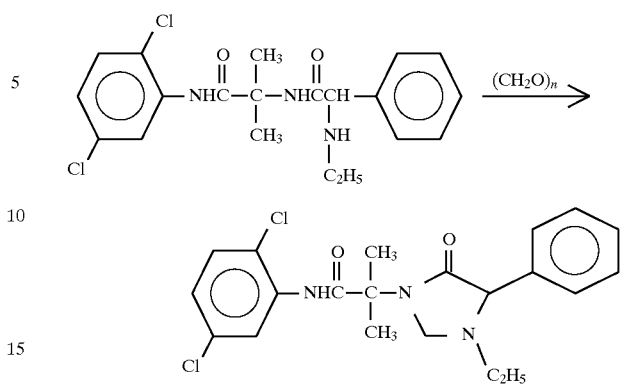

(1) A sodium hydroxide (1.6 g) aqueous solution (40 mL) was added to aminoisobutyric acid (2.1 g). The solution was cooled to 0° C., to which a solution of σ-bromophenylacetyl chloride (6 g) in acetonitrile (5 mL) was slowly added dropwise. After the addition was completed, the mixture was warmed to room temperature and stirred overnight. The precipitate was filtered off and washed with water to give 3.4 g of 2-(σ--bromophenylacetylamino)isobutyric acid.

$^1$H-NMR[CDCl$_3$+DMSO-d$_6$]: 1.47 (3H, s), 1.50 (3H, s), 5.60 (1H, s), 7.27–7.56 (5H, m), 8.27 (2H, brs).

m.p.: 163°–164° C.

(2) A solution of 2-(σ-bromophenylacetylamino) isobutyric acid (1.9 g) in dichloromethane (30 mL) was cooled to 0° C., to which dimethylaminopropylethylcarbodiimide hydrochloride (1.3 g) was added. The mixture was stirred for 10 minutes at 0° C. to room temperature. 2,5-Dichloroaniline (1.0 g) was added to the mixture, which was stirred overnight at room temperature. The reaction solution was poured into water and the mixture was extracted with chloroform. The organic layer was washed with water and dried over anhydrous sodium sulfate. After distilling off the solvent, 2.3 g of N-(2,5-dichlorophenyl)-2-(σ-bromophenylacetylamino)isobutyramide was obtained as viscous liquid.

(3) To a solution of N-(2,5-dichlorophenyl)-2-(σ-bromophenylacetylamino)isobutyramide (2.3 g) in ethanol (20 mL) were added a 70% ethylamine aqueous solution (20 g) and potassium iodide (150 mg), and the mixture was stirred overnight at room temperature. After concentrated under reduced pressure, water was added, and the mixture was then acidified with concentrated hydrochloric acid. The mixture was extracted with diethyl ether. After separating the extract, the aqueous layer was basified with sodium hydrogencarbonate and extracted with ethyl acetate. The organic layer was washed with water and dried over anhydrous sodium sulfate. After distilling off the solvent under reduced pressure, 0.9 g of N-(2,5-dichlorophenyl)-2-(σ-ethylaminophenylacetylamino)isobutyramide as viscous liquid.

(4) To a solution of N-(2,5-dichlorophenyl)-2-(σ-ethylaminophenylacetylamino)isobutyramide (0.9 g) in ethanol (15 mL) were added potassium carbonate (0.5 g) and paraformaldehyde (0.5 g), and the mixture was heated at reflux for 4 hours. After the reaction solution was added to water, the mixture was extracted with ethyl acetate. The organic layer was washed with water and dried over anhydrous sodium sulfate. After distilling off the solvent under reduced pressure, the resulting crude product was purified by thin-layer chromatography (silica gel, diethyl ether/n-hexane=1/1) to give 0.4 g of the title compound.

EXAMPLE 11

Preparation of ethyl 2-(5-phenylthiazolidin-4-on-3-yl)isobutyrate (Compound No. D-2)

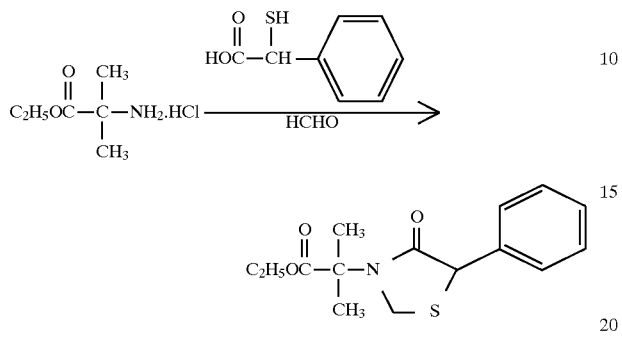

Triethylamine (3 g) was added to a suspension of ethyl 2-aminoisobutyrate hydrochloride (5 g) in toluene (60 mL) at room temperature. 2-Mercaptophenylacetic acid (6.44 g) was added to the mixture, which was then stirred at room temperature. After 10 minutes, a 35% formaldehyde aqueous solution (2.61 g) was added dropwise to the mixture. After the addition was completed, a catalytic amount of p-toluenesulfonic acid was added, and the mixture was allowed to react under heating at reflux for 4 hours, while water generated was excluded by azeotropic distillation from the reaction system. The reaction mixture was cooled to room temperature, to which ethyl acetate was added, and was then washed with a saturated sodium hydrogencarbonate aqueous solution and a saturated aqueous sodium chloride and dried over anhydrous sodium sulfate. The solvent was distilled under reduced pressure to give 5.49 g of the title compound as viscous oil.

EXAMPLE 12

Preparation of 2-(5-phenylthiazolidin-4-on-3-yl)isobutyric acid (Compound No. D-3)

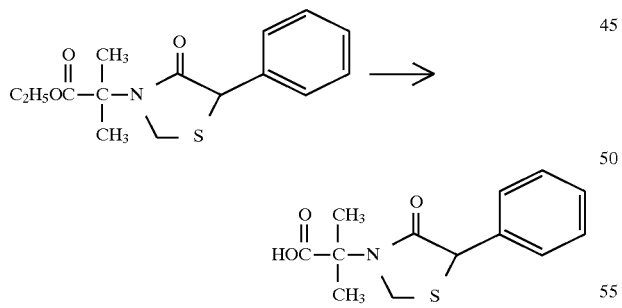

To a solution of ethyl 2-(5-phenylthiazolidin-4-on-3-yl)isobutyrate (2 g) prepared according to Example 11 in ethanol (10 mL) were added 85% potassium hydroxide (0.45 g) and water (1 mL), and the mixture was then heated at reflux for 1 hour. After distilling off the solvent under reduced pressure, ice-water was added to the residue and the resulting mixture was acidified to pH 2–3 with concentrated hydrochloric acid. The mixture was then extracted with ethyl acetate, washed with a saturated aqueous sodium chloride and dried over anhydrous sodium sulfate. After distilling off ethyl acetate under reduced pressure, the residual viscous product was crystallized by adding isopropyl ether. The crystals were filtered off and washed with isopropyl ether to give 1 g of the title compound as crystals.

EXAMPLE 13

Preparation of N-(2,5-difluorophenyl)-2-(5-phenylthiazolidin-4-on-3-yl)isobutyramide (Compound No. D-5)

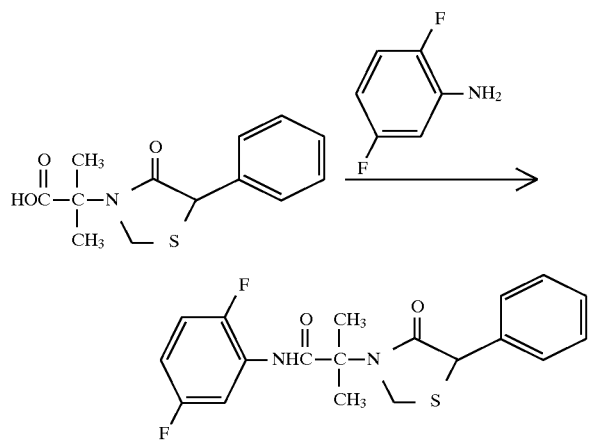

Triphenylphosphine (1.93 g) was added to a suspension of 2-(5-phenylthiazolidin-4-on-3-yl)isobutyric acid (1.5 g) prepared according to Example 12 in carbon tetrachloride (15 mL) and dichloromethane (15 mL), and the mixture was heated for 40 minutes at 70° C. The reaction mixture was cooled with ice-water, to which 2,5-difluoroaniline (0.73 g) and then triethylamine (0.57 g) were added, and the mixture was stirred for 3 days at room temperature. The reaction mixture was diluted with chloroform, and then sequentially washed with water, diluted hydrochloric acid and a saturated sodium hydrogencarbonate aqueous solution, and dried over anhydrous sodium sulfate. After distilling off the solvent under reduced pressure, the resulting crude product was purified by preparative thin-layer chromatography (developing solvent: chloroform/ethyl acetate=10/1) to give 0.92 g of the title compound as viscous oil.

Example 14

Preparation of N-(2,5-difluorophenyl)-2-(1,1-dioxo-5-phenylthiazolidin-4-on-3-yl)isobutyramide (Compound No. D-6)

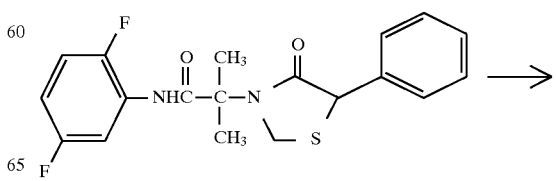

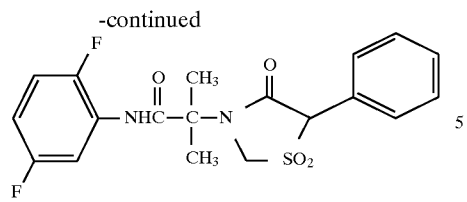

To a solution of N-(2,5-difluorophenyl)-2-(5-phenylthiazolidin-4-on-3-yl)isobutyramide (1.3 g) prepared according to Example 13 in dichloromethane (25 mL) was added portionwise 70% m-chloroperbenzoic acid (1 g) under ice-cooling, and the mixture was stirred for 30 minutes at room temperature. After adding a small amount of sodium thiosulfate, the mixture was diluted with chloroform and washed with a saturated sodium hydrogencarbonate aqueous solution. After distilling off the solvent under reduced pressure, the resulting crude product was purified by preparative thin-layer chromatography (developing solvent: chloroform/ethyl acetate=3/1) to give crystals, which were washed with a mixture of isopropyl ether-ethanol (10:1) to give 0.26 g of the title compound as crystals.

The compounds of the present invention prepared according to the procedures illustrated in the above Schemes and Examples are shown in the following tables, including the compounds specifically described in the above Examples. Their structural formulas are shown in Tables 1-A to 1-D, and their physical properties in Tables 2-A to 2-D.

TABLE 1A

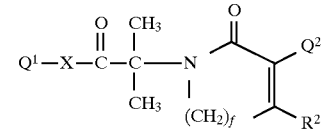

| Compound No. | $Q^1$ | X | $R^2$ | f | $Q^2$ |
|---|---|---|---|---|---|
| A-1 | Et | O | Me | 1 | Q-5 |
| A-2 | 2,5-$Cl_2$-Ph | NH | Me | 1 | Q-5 |
| A-3 | H | O | Me | 1 | Q-4 |
| A-4 | 2,5-$Cl_2$-Ph | NH | Me | 1 | Q-4 |
| A-5 | Q-24 | NH | Me | 1 | Ph |
| A-6 | Q-32 | NH | Me | 1 | Ph |
| A-7 | Q-39 | NH | Me | 1 | Ph |
| A-8 | 2,5-$Cl_2$-Ph | NH | Me | 2 | Ph |
| A-9 | Q-40 | NH | Me | 1 | Ph |
| A-10 | 3,5-$Cl_2$-Ph | NH | Me | 1 | Q-5 |
| A-11 | 5-Me-Q-32 | NH | Me | 1 | Ph |
| A-12 | Q-57 | NH | Me | 1 | Ph |
| A-13 | 3,5-$Cl_2$-Ph | NH | Me | 2 | Ph |
| A-14 | 3,5-$Cl_2$-Ph | NH | Et | 2 | Ph |
| A-15 | 2-$NO_2$-Ph | NH | Me | 1 | Q-5 |
| A-16 | 5-$CF_3$-Q-32 | NH | Me | 1 | Ph |
| A-17 | 5-t-Bu-Q-32 | NH | Me | 1 | Ph |
| A-18 | 5-EtS-Q-32 | NH | Me | 1 | Ph |
| A-19 | 5-EtSO-Q-32 | NH | Me | 1 | Ph |
| A-20 | 5-$EtSO_2$-Q-32 | NH | Me | 1 | Ph |
| A-21 | 5-c-Pr-Q-32 | NH | Me | 1 | Ph |
| A-22 | 5-Cl-Q-24 | NH | Me | 1 | Ph |
| A-23 | 4-Me-Q-24 | NH | Me | 1 | Ph |
| A-24 | 3,5-$Cl_2$-Ph | NH | Me | 2 | Q-4 |
| A-25 | 3,5-$Cl_2$-Ph | NH | Me | 2 | Q-5 |
| A-26 | 6-OMe-Q-57 | NH | Me | 1 | Ph |
| A-27 | 5-Me-Q-24 | NH | Me | 1 | Ph |
| A-28 | 5-Br-Q-24 | NH | Me | 1 | Ph |
| A-29 | 4,5-$Me_2$-Q-24 | NH | Me | 1 | Ph |
| A-30 | 2,5-$Cl_2$-Ph | NH | Me | 2 | Q-4 |
| A-31 | 3,5-$Cl_2$-Ph | NH | Me | 2 | 2-F-Ph |
| A-32 | 4-Cl-Q-57 | NH | Me | 1 | Ph |

TABLE 1A-continued

| Compound No. | $Q^1$ | X | $R^2$ | f | $Q^2$ |
|---|---|---|---|---|---|
| A-33 | 5-Cl-Q-24 | NH | Me | 1 | 2-F-Ph |
| A-34 | 2,5-$Cl_2$-Ph | NH | Me | 2 | 2-F-Ph |
| A-35 | 3,5-$F_2$-Ph | NH | Me | 2 | Ph |
| A-36 | 6-Cl-Q-57 | NH | Me | 1 | Ph |
| A-37 | 6-F-Q-57 | NH | Me | 1 | Ph |
| A-38 | 5-$NO_2$-Q-24 | NH | Me | 1 | Ph |
| A-39 | 4-t-Bu-Q-24 | NH | Me | 1 | Ph |
| A-40 | 3,5-$F_2$-Ph | NH | Me | 2 | 2-F-Ph |
| A-41 | 5-$CF_3$-Q-32 | $NCH_3$ | Me | 1 | Ph |
| A-42 | 5-Br-Q-32 | NH | Me | 1 | Ph |
| A-43 | 3,5-$Cl_2$-Ph | NH | Me | 2 | 2-Cl-Ph |
| A-44 | 4-Me-5-Cl-Q-24 | NH | Me | 1 | Ph |
| A-45 | 6-Cl-Q-40 | NH | Me | 1 | Ph |
| A-46 | 4-Me-5-Br-Q-24 | NH | Me | 1 | Ph |
| A-47 | 3-$CF_3$-Ph | NH | Me | 2 | 2-F-Ph |
| A-48 | 5-Br-Q-32 | NH | Me | 1 | 2-F-Ph |
| A-49 | Q-27 | NH | Me | 1 | Ph |
| A-50 | Q-47 | NH | Me | 1 | Ph |
| A-51 | Q-44 | NH | Me | 1 | Ph |
| A-52 | 4,6-$Cl_2$-Q-44 | NH | Me | 1 | Ph |
| A-53 | 3,4,5-$Cl_3$-Ph | NH | Me | 2 | Ph |
| A-54 | 3,4,5-$Cl_3$-Ph | NH | Me | 2 | 2-F-Ph |
| A-55 | 2-F-5-Cl-Ph | NH | Me | 2 | Ph |
| A-56 | 2-F-5-Cl-Ph | NH | Me | 2 | 2-F-Ph |
| A-57 | 4-Me-5-Cl-Q-24 | NH | Me | 1 | 2-F-Ph |
| A-58 | 5-Br-Q-24 | NH | Me | 1 | 2-F-Ph |
| A-59 | 5-Cl-Q-24 | NH | Et | 1 | Ph |
| A-60 | 4,6-$(OMe)_2$-Q-44 | NH | Me | 1 | Ph |
| A-61 | 2,5-$F_2$-Ph | NH | Me | 2 | Ph |
| A-62 | 2,5-$F_2$-Ph | NH | Me | 2 | 2-F-Ph |
| A-63 | 3,5-$Cl_2$-Ph | NH | Me | 2 | 2,6-F2-Ph |
| A-64 | 2-Cl-5-F-Ph | NH | Me | 2 | Ph |
| A-65 | 2-Cl-5-F-Ph | NH | Me | 2 | 2-F-Ph |
| A-66 | 4-Me-5-Br-Q-24 | NH | Me | 1 | 2-F-Ph |
| A-67 | 3-Cl-Q-10($R^4$ = Me) | NH | Me | 1 | Ph |
| A-68 | 3,4-$Cl_2$-Q-10($R^4$ = Me) | NH | Me | 1 | Ph |
| A-69 | 2,3,5-$Cl_3$-Ph | NH | Me | 2 | 2-F-Ph |
| A-70 | Q-10($R^4$ = Me) | NH | Me | 1 | Ph |
| A-71 | 3-Me-Q-10($R^4$ = Me) | NH | Me | 1 | Ph |
| A-72 | 2-Cl-5-$CF_3$-Ph | NH | Me | 2 | 2-F-Ph |
| A-73 | 3-$CF_3$-Ph | NH | Me | 2 | Ph |
| A-74 | 3,5-$(CF_3)_2$-Ph | NH | Me | 2 | Ph |
| A-75 | 3,5-$(CF_3)_2$-Ph | NH | Me | 2 | 2-F-Ph |
| A-76 | 5-Cl-Q-32 | NH | Me | 1 | Ph |
| A-77 | 5-Cl-Q-32 | NH | Me | 1 | 2-F-Ph |
| A-78 | 2-F-5-$CF_3$-Ph | NH | Me | 2 | Ph |
| A-79 | 2-F-5-$CF_3$-Ph | NH | Me | 2 | 2-F-Ph |
| A-80 | 3,5-$F_2$-Ph | NH | Et | 2 | Ph |
| A-81 | 3,5-$F_2$-Ph | NH | Et | 2 | 2-F-Ph |
| A-82 | 3-Cl-Ph | NH | Me | 2 | Ph |
| A-83 | 3-Cl-Ph | NH | Me | 2 | 2-F-Ph |
| A-84 | 3-Cl-Ph | NH | Me | 2 | 2-Cl-Ph |
| A-85 | 2-F-5-Cl-Ph | NH | Me | 2 | 2-Cl-Ph |
| A-86 | 2,5-$F_2$-Ph | NH | Me | 2 | 2-Cl-Ph |
| A-87 | 3-$CF_3$-Ph | NH | Me | 2 | 2-Cl-Ph |
| A-88 | 2-F-5-$CF_3$-Ph | NH | Me | 2 | 2-Cl-Ph |
| A-89 | 3-$CF_3$-Q-10($R^4$ = Me) | NH | Me | 1 | Ph |
| A-90 | 3-i-Pr-Ph | NH | Me | 2 | Ph |
| A-91 | 2,5-$F_2$-Ph | NH | Me | 2 | 2,6-F2-Ph |
| A-92 | 2-F-5-Cl-Ph | NH | Me | 2 | 2,6-F2-Ph |
| A-93 | 3-$CF_3$-Ph | NH | Me | 2 | 2,6-F2-Ph |
| A-94 | 3-$OCHF_2$-Ph | NH | Me | 2 | Ph |
| A-95 | 3-CN-Ph | NH | Me | 2 | Ph |
| A-96 | 3-CN-Ph | NH | Me | 2 | 2-F-Ph |
| A-97 | 3-CN-Ph | NH | Me | 2 | 2-Cl-Ph |
| A-98 | 3-Br-Ph | NH | Me | 2 | Ph |
| A-99 | 3-Br-Ph | NH | Me | 2 | 2-F-Ph |
| A-100 | 3-Me-Ph | NH | Me | 2 | Ph |
| A-101 | 3-Me-Ph | NH | Me | 2 | 2-F-Ph |

TABLE 1A-continued

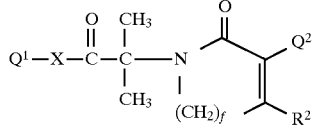 

| Compound No. | Q¹ | X | R² | f | Q² |
|---|---|---|---|---|---|
| A-102 | 3-CF$_3$-Ph | NH | Me | 2 | Q-4 |
| A-103 | 2,5-F$_2$-Ph | NH | Me | 2 | Q-4 |
| A-104 | 3-F-Ph | NH | Me | 2 | Ph |
| A-105 | 3-F-Ph | NH | Me | 2 | 2-F-Ph |
| A-106 | 3-F-5-CF$_3$-Ph | NH | Me | 2 | Ph |
| A-107 | 3-OMe-Ph | NH | Me | 2 | Ph |
| A-108 | 3-OMe-Ph | NH | Me | 2 | 2-F-Ph |
| A-109 | 3-I-Ph | NH | Me | 2 | Ph |
| A-110 | 3-I-Ph | NH | Me | 2 | 2-F-Ph |
| A-111 | 2-F-5-Me-Ph | NH | Me | 2 | Ph |
| A-112 | 2-F-5-Me-Ph | NH | Me | 2 | 2-F-Ph |
| A-113 | 3-Me-Q-34 | NH | Me | 1 | Ph |
| A-114 | 4-CF$_3$-Q-24 | NH | Me | 1 | Ph |
| A-115 | 4-CF$_3$-Q-24 | NH | Me | 1 | 2-F-Ph |
| A-116 | 4-C$_2$F$_5$-Q-24 | NH | Me | 1 | Ph |
| A-117 | 4-Et-5-Me-Q-24 | NH | Me | 1 | Ph |
| A-118 | 2-Cl-5-CF$_3$-Ph | NH | Me | 2 | Ph |
| A-119 | 2-F-5-Br-Ph | NH | Me | 2 | Ph |
| A-120 | 3-F-5-CF$_3$-Ph | NH | Me | 2 | 2-F-Ph |
| A-121 | | | | | |
| A-122 | | | | | |
| A-123 | | | | | |
| A-124 | | | | | |
| A-125 | | | | | |
| A-126 | | | | | |
| A-127 | | | | | |
| A-128 | | | | | |
| A-129 | | | | | |
| A-130 | | | | | |
| A-131 | | | | | |
| A-132 | | | | | |
| A-133 | | | | | |
| A-134 | | | | | |
| A-135 | | | | | |
| A-136 | | | | | |
| A-137 | | | | | |

TABLE 1-B

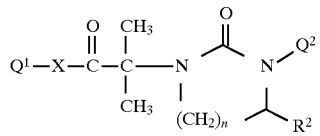

| Compound No. | Q¹ | X | R² | n | Q² |
|---|---|---|---|---|---|
| B-1 | H | O | H | 2 | Ph |
| B-2 | 3,5-Cl$_2$-Ph | NH | H | 2 | Ph |
| B-3 | 2,5-Cl$_2$-Ph | NH | H | 2 | Ph |
| B-4 | 5-Cl-Q-24 | NH | H | 2 | Ph |
| B-5 | H | O | H | 2 | 2-F-Ph |
| B-6 | 3,5-Cl$_2$-Ph | NH | H | 2 | 2-F-Ph |
| B-7 | 2,5-Cl$_2$-Ph | NH | H | 2 | 2-F-Ph |
| B-8 | 5-Cl-Q-24 | NH | H | 2 | 2-F-Ph |
| B-9 | 2,5-F$_2$-Ph | NH | H | 2 | 2-F-Ph |
| B-10 | 6-Cl-Q-40 | NH | H | 2 | Ph |
| B-11 | 5-Cl-Q-39 | NH | H | 2 | Ph |
| B-12 | 2-Cl-Q-40 | NH | H | 2 | Ph |
| B-13 | 5-Br-Q-32 | NH | H | 2 | Ph |
| B-14 | 3,4,5-Cl$_3$-Ph | NH | H | 2 | Ph |
| B-15 | 2-F-5-Cl-Ph | NH | H | 2 | Ph |
| B-16 | 4,6-(OMe)$_2$-Q-44 | NH | H | 2 | Ph |
| B-17 | Q-45 | NH | H | 2 | Ph |
| B-18 | 3,5-Me$_2$-Q-9(R$^4$ = Me) | NH | H | 2 | Ph |
| B-19 | 2-Cl-5-NO$_2$-Ph | NH | H | 2 | Ph |

TABLE 1-B-continued

| Compound No. | Q¹ | X | R² | n | Q² |
|---|---|---|---|---|---|
| B-20 | 2,5-Cl$_2$-Ph | O | H | 2 | Ph |
| B-21 | 3,5-F$_2$-Ph | NH | H | 2 | Ph |
| B-22 | 3,5-F$_2$-Ph | NH | H | 2 | 2-F-Ph |
| B-23 | 2-Cl-3,5-F$_2$-Ph | NH | H | 2 | Ph |
| B-24 | 2-Cl-3,5-F$_2$-Ph | NH | H | 2 | 2-F-Ph |
| B-25 | 2,3,5-Cl$_3$-Ph | NH | H | 2 | Ph |
| B-26 | 2,3,5-Cl$_3$-Ph | NH | H | 2 | 2-F-Ph |
| B-27 | 2,5-F$_2$-Ph | NH | H | 2 | Ph |
| B-28 | 2-Cl-5-F-Ph | NH | H | 2 | Ph |
| B-29 | 2,4,5-F$_3$-Ph | NH | H | 2 | Ph |
| B-30 | 2,3,4,5-F$_4$-Ph | NH | H | 2 | Ph |
| B-31 | 6-Cl-Q-45 | NH | H | 2 | Ph |
| B-32 | 3-CF$_3$-Ph | NH | H | 2 | Ph |
| B-33 | 2-Cl-5-CF$_3$-Ph | NH | H | 2 | Ph |
| B-34 | 3-CN-Ph | NH | H | 2 | Ph |
| B-35 | 2,6-Cl$_2$-Q-45 | NH | H | 2 | Ph |
| B-36 | 2-F-5-Cl-Ph | NH | H | 2 | 2-F-Ph |
| B-37 | 2-Cl-5-F-Ph | NH | H | 2 | 2-F-Ph |
| B-38 | 2,4,5-F$_3$-Ph | NH | H | 2 | 2-F-Ph |
| B-39 | 2,5-Br$_2$-Ph | NH | H | 2 | Ph |
| B-40 | 2-F-5-CF$_3$-Ph | NH | H | 2 | Ph |
| B-41 | Q-10(R$^4$ = Me) | NH | H | 2 | Ph |
| B-42 | 3-Cl-Q-10(R$^4$ = Me) | NH | H | 2 | Ph |
| B-43 | Q-47 | NH | H | 2 | Ph |
| B-44 | 3,5-(CF$_3$)$_2$-Ph | NH | H | 2 | Ph |
| B-45 | 2,6-F$_2$-Ph | NH | H | 2 | Ph |
| B-46 | 2-Cl-5-CO$_2$i-Pr-Ph | NH | H | 2 | Ph |
| B-47 | Q-8(R$^4$ = Me) | NH | H | 2 | Ph |
| B-48 | 4-Br-Q-8(R$^4$ = Me) | NH | H | 2 | Ph |
| B-49 | 3,5-Cl$_2$-Ph | NH | H | 1 | Ph |
| B-50 | 5-Cl-Q-24 | NH | H | 1 | Ph |
| B-51 | 3-CF$_3$-Ph | NH | H | 2 | 2-F-Ph |
| B-52 | 2-F-5-CF3-Ph | NH | H | 2 | 2-F-Ph |
| B-53 | 3-C$_2$H$_5$-Ph | NH | H | 2 | Ph |
| B-54 | 3-i-Pr-Ph | NH | H | 2 | Ph |
| B-55 | 3,5-Cl$_2$-Q-9(R$^4$ = Me) | NH | H | 2 | Ph |
| B-56 | 2,5-(CF$_3$)$_2$-Ph | NH | H | 2 | Ph |
| B-57 | 6-Cl-Q-47 | NH | H | 2 | Ph |
| B-58 | 3-CF$_3$-Q-10(R$^4$ = Me) | NH | H | 2 | Ph |
| B-59 | 2,3,6-F$_3$-Ph | NH | H | 2 | Ph |
| B-60 | 2-Cl-5-CF$_3$-Ph | NH | H | 2 | 2-F-Ph |
| B-61 | 3-OCHF$_2$-Ph | NH | H | 2 | Ph |
| B-62 | 3-F-5-CF$_3$-Ph | NH | H | 2 | Ph |
| B-63 | 3-F-5-CF$_3$-Ph | NH | H | 2 | 2-F-Ph |
| B-64 | 2-Cl-5-CN-Ph | NH | H | 2 | Ph |
| B-65 | 3-Me-Ph | NH | H | 2 | Ph |
| B-66 | 3-OMe-Ph | NH | H | 2 | Ph |
| B-67 | 3-Br-Ph | NH | H | 2 | Ph |
| B-68 | 3-I-Ph | NH | H | 2 | Ph |
| B-69 | 2-F-5-Me-Ph | NH | H | 2 | Ph |
| B-70 | 3-Cl-Ph | NH | H | 2 | Ph |
| B-71 | 3-CO$_2$Me | NH | H | 2 | Ph |
| B-72 | H | O | H | 2 | 2-Cl-Ph |
| B-73 | H | O | H | 2 | 2-CF$_3$-Ph |
| B-74 | 3,5-F$_2$-Ph | NH | H | 2 | 2-Cl-Ph |
| B-75 | 3,5-F$_2$-Ph | NH | H | 2 | 2-CF$_3$-Ph |
| B-76 | 3-OCF$_3$-Ph | NH | H | 2 | Ph |
| B-77 | 3-F-Ph | NH | H | 2 | Ph |
| B-78 | 3-Br-Ph | NH | H | 2 | 2-F-Ph |
| B-79 | 3-SMe-Ph | NH | H | 2 | Ph |
| B-80 | 3-SOMe-Ph | NH | H | 2 | Ph |
| B-81 | 3-SO$_2$Me-Ph | NH | H | 2 | Ph |
| B-82 | Q-34 | NH | H | 2 | Ph |
| B-83 | 3-Me-Q-34 | NH | H | 2 | Ph |
| B-84 | 3-Cl-5-CF$_3$-Ph | NH | H | 2 | Ph |
| B-85 | 3-Cl-5-CF$_3$-Ph | NH | H | 2 | 2-F-Ph |
| B-86 | 2-Cl-5-Br-Ph | NH | H | 2 | Ph |
| B-87 | 4-CF$_3$-Q-24 | NH | H | 2 | Ph |
| B-88 | 4-C$_2$F$_5$-Q-24 | NH | H | 2 | Ph |

TABLE 1-B-continued

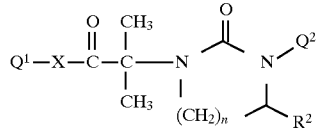

| Compound No. | Q¹ | X | R² | n | Q² |
|---|---|---|---|---|---|
| B-89 | H | NH | H | 2 | Ph |
| B-90 | H | O | Me | 2 | Ph |
| B-91 | 3,5-F₂-Ph | NH | Me | 2 | Ph |
| B-92 | 5-Cl-Q-24 | NH | Me | 2 | Ph |
| B-93 | 3-F-5-I-Ph | NH | H | 2 | Ph |
| B-94 | 3-Cl-5-Br-Ph | NH | H | 2 | Ph |
| B-95 | 4-Et-5-Me-Q-24 | NH | H | 2 | Ph |
| B-96 | H | O | H | 1 | Ph |
| B-97 | 3,5-F₂-Ph | NH | H | 1 | Ph |
| B-98 | 3-Cl-Ph | NH | H | 2 | 2-F-Ph |
| B-99 | 3-Br-5-CF₃-Ph | NH | H | 2 | Ph |
| B-100 | 3,5-Br₂-Ph | NH | H | 2 | Ph |
| B-101 | 2-F-5-Br-Ph | NH | H | 2 | Ph |
| B-102 | 5-Cl-Q-34 | NH | H | 2 | Ph |
| B-103 | H | O | H | 2 | 2,6-F₂-Ph |
| B-104 | 3,5-F₂-Ph | NH | H | 2 | 2,6-F₂-Ph |
| B-105 | 3-Br-Ph | NH | H | 2 | 2,6-F₂-Ph |
| B-106 | 5-Cl-Q-24 | NH | H | 2 | 2,6-F₂-Ph |
| B-107 | 4-CF₃-5-Cl-Q-24 | NH | H | 2 | Ph |
| B-108 | 4-CF₃-5-Br-Q-24 | NH | H | 2 | Ph |
| B-109 | 4-Cl-Q-24 | NH | H | 2 | Ph |
| B-110 | 3-Cl-Ph | NH | H | 2 | 2,6-F₂-Ph |
| B-111 | 3-Me-Q-34 | NH | H | 2 | 2-F-Ph |
| B-112 | 3-Cl-Ph | NH | Me | 2 | Ph |
| B-113 | 3-F-5-CF₃-Ph | NH | Me | 2 | Ph |
| B-114 | H | O | Me | 2 | 2-F-Ph |
| B-115 | 3,5-F₂-Ph | NH | Me | 2 | 2-F-Ph |
| B-116 | 3-Cl-Ph | NH | Me | 2 | 2-F-Ph |
| B-111 | 5-Cl-Q-24 | NH | Me | 2 | 2-F-Ph |
| B-118 | 4-CF₃-5-Cl-Q-24 | NH | H | 2 | 2-F-Ph |
| B-119 | 4-CF₃-5-Br-Q-24 | NH | H | 2 | 2-F-Ph |
| B-120 | 4-CF₃-Q-24 | NH | H | 2 | 2-F-Ph |
| B-121 | 3-Cl-5-OMe-Ph | NH | H | 2 | Ph |
| B-122 | 3-Cl-5-F-Ph | NH | H | 2 | Ph |
| B-123 | 3-F-4-CF₃-Ph | NH | H | 2 | Ph |
| B-124 | 2-Me-5-Cl-Ph | NH | H | 2 | Ph |
| B-125 | 2-F-5-CN-Ph | NH | H | 2 | Ph |
| B-126 | 2-F-5-CN-Ph | NH | H | 2 | 2-F-Ph |
| B-127 | | | | | |
| B-128 | | | | | |
| B-129 | | | | | |
| B-130 | | | | | |
| B-131 | | | | | |
| B-132 | | | | | |
| B-133 | | | | | |
| B-134 | | | | | |
| B-135 | | | | | |
| B-136 | | | | | |
| B-137 | | | | | |
| B-138 | | | | | |
| B-139 | | | | | |
| B-140 | | | | | |
| B-141 | | | | | |
| B-142 | | | | | |
| B-143 | | | | | |
| B-144 | | | | | |
| B-145 | | | | | |
| B-146 | | | | | |
| B-147 | | | | | |

TABLE 1-C

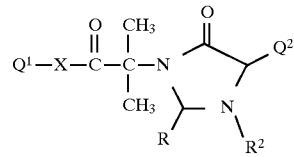

| Compound No. | R² | R | X | Q¹ | Q² |
|---|---|---|---|---|---|
| C-1 | Et | H | NH | 2,5-Cl₂-Ph | Ph |
| C-2 | Et | H | O | Et | Ph |
| C-3 | Et | H | O | H | Ph |
| C-4 | Et | H | NH | Ph | Ph |
| C-5 | Et | H | NR | 2-OMe-Ph | Ph |
| C-6 | Et | H | NH | 2-OMe-5-Cl-Ph | Ph |
| C-7 | Et | H | NH | c-Hex | Ph |
| C-8 | Et | H | NH | Q-24 | Ph |
| C-9 | Et | H | NH | 3,5-Cl₂-Ph | Ph |
| C-10 | Et | H | NH | 4-OMe-Ph | Ph |
| C-11 | Et | H | NH | 3,5-(OMe)₂-Ph | Ph |
| C-12 | Et | H | NH | 2,5-F₂-Ph | Ph |
| C-13 | Et | H | NH | 2-Et-Ph | Ph |
| C-14 | Et | H | O | Prop | Ph |
| C-15 | Et | H | NH | 3-Cl-Ph | Ph |
| C-16 | Et | H | NH | 2-Cl-Ph | Ph |
| C-17 | Et | H | NH | 4-Cl-Ph | Ph |
| C-18 | Et | H | NH | 2,4,5-Cl₃-Ph | Ph |
| C-19 | Et | H | NH | 3-NO₂-Ph | Ph |
| C-20 | Et | H | NH | 2,3-Cl₂-Ph | Ph |
| C-21 | Et | H | NH | 2,4-Cl₂-Ph | Ph |
| C-22 | Et | H | NH | 3,4-Cl₂-Ph | Ph |
| C-23 | Et | H | NH | 3,5-(CF₃)₂-Ph | Ph |
| C-24 | Et | H | NH | Q-53 | Ph |
| C-25 | Et | H | O | H | 2-Cl-Ph |
| C-26 | Et | H | NH | 3,5-Cl₂-Ph | 2-Cl-Ph |
| C-27 | Me | H | O | H | 2-Cl-Ph |
| C-28 | Me | H | NH | 2,5-Cl₂-Ph | 2-Cl-Ph |
| C-29 | Me | H | NH | 3,5-Cl₂-Ph | 2-Cl-Ph |
| C-30 | Et | H | NH | 5-Me-Q-32 | Ph |
| C-31 | Et | H | NH | 3,5-(CO₂Me)₂-Ph | Ph |
| C-32 | Et | H | NH | 2,5-Cl₂-Ph | 2-F-Ph |
| C-33 | Et | H | NH | 3,5-Cl₂-Ph | 2-F-Ph |
| C-34 | Me | H | NH | 3,5-Cl₂-Ph | Ph |
| C-35 | Me | H | NH | 2,5-Cl₂-Ph | Ph |
| C-36 | Me | H | NH | 3,5-Cl₂-Ph | 2-F-Ph |
| C-37 | Me | H | NH | 2,5-Cl₂-Ph | 2-F-Ph |
| C-38 | Et | H | NH | 5-Cl-Q-24 | Ph |
| C-39 | Me | H | NH | 5-Cl-Q-24 | 2-F-Ph |
| C-40 | Et | H | NH | 3-Me-Q-23 | Ph |
| C-41 | Et | H | NH | 3-Me-Q-16 | Ph |
| C-42 | Me | H | NH | 3,4,5-Cl₃-Ph | 2-F-Ph |
| C-43 | Me | H | NH | 3,5-F₂-Ph | 2-F-Ph |
| C-44 | Me | H | NH | 3-Br-Ph | 2-F-Ph |
| C-45 | | | | | |
| C-46 | | | | | |
| C-47 | | | | | |
| C-48 | | | | | |
| C-49 | | | | | |
| C-50 | | | | | |
| C-51 | | | | | |
| C-52 | | | | | |
| C-53 | | | | | |
| C-54 | | | | | |
| C-55 | | | | | |
| C-56 | | | | | |
| C-57 | | | | | |

TABLE 1-D $$Q^1-X-\underset{\underset{O}{\|}}{C}-\underset{\underset{R}{|}}{\overset{\overset{CH_3}{|}}{C}}-N(\underset{S(O)_r}{CH_3})-\underset{\underset{O}{\|}}{C}-Q^2$$

| Compound No. | r | R | X | Q¹ | Q² |
|---|---|---|---|---|---|
| D-1 | 0 | H | NH | 3,5-Cl₂-Ph | Ph |
| D-2 | 0 | H | O | Et | Ph |
| D-3 | 0 | H | O | H | Ph |
| D-4 | 0 | H | NH | 3,5-F₂-Ph | Ph |
| D-5 | 0 | H | NH | 2,5-F₂-Ph | Ph |
| D-6 | 2 | H | NH | 2,5-F₂-Ph | Ph |
| D-7 | 1 | H | NH | 2,5-F₂-Ph | Ph |
| D-8 | 0 | H | NH | 3-Cl-Ph | Ph |
| D-9 | 0 | H | NH | 3-OMe-5-CF₃-Ph | Ph |
| D-10 | | | | | |
| D-11 | | | | | |
| D-12 | | | | | |
| D-13 | | | | | |
| D-14 | | | | | |
| D-15 | | | | | |
| D-16 | | | | | |
| D-17 | | | | | |

TABLE 2-A

| Compound No. | ¹H—NMRδ (ppm) (Solvent) | Physical property |
|---|---|---|
| A-1 | 1.24(3H, t, J=7Hz), 1.59(6H, s), 2.21(3H, s), 3.99(2H, s), 4.21(2H, q, J=7Hz), 7.19~7.83(3H, m) [CDCl₃] | m.p. 63~65° C. |
| A-2 | 1.71(6H, s), 2.25(3H, s), 4.09(2H, s), 6.82~7.83(5H, m), 8.50(1H, d, J=2Hz), 8.81(1H, bs) [CDCl₃] | glassy |
| A-3 | 1.54(6H, s), 2.27(3H, d, J=2Hz), 4.10(2H, s), 6.95~7.99(3H, m), 10.06(1H, bs) [d₆-DMSO] | m.p. 137~140° C. |
| A-4 | 1.68(6H, s), 2.26(3H, s), 4.08(2H, s), 6.39~7.68(5H, m), 8.46(1H, d, J=2Hz), 8.70(1H, bs) [CDCl₃] | viscous oil |
| A-5 | 1.61(6H, s), 2.11(3H, s), 3.89(2H, s), 6.91(1H, d, J=4Hz), 7.15~8.31(5H, m), 8.86(1H, d, J=2Hz) [CDCl₃] | m.p. 115~118° C. |
| A-6 | 1.60(6H, s), 2.05(3H, s), 4.10(2H, s), 6.93~7.98(5H, m), 8.76(1H, s), 12.32(1H, bs) [CDCl₃] | m.p. 225~228° C. |
| A-7 | 1.64(6H, s), 2.11(3H, s), 4.03(2H, s), 6.78~8.40(9H, m), 8.98(1H, bs) [CDCl₃] | viscous oil |
| A-8 | 1.55(6H, s), 1.80(3H, s), 2.57(2H, t, J=6Hz), 3.53(2H, t, J=6Hz), 6.73~7.37(7H, m), 8.22(1H, bs), 8.40(1H, d, J=2Hz) [CDCl₃] | m.p. 165~170° C. |
| A-9 | 1.69(6H, s), 2.08(3H, s), 4.02(2H, s), 6.86~8.33(8H, m), 8.63(1H, d, J=2Hz), 9.75(1H, s) [CDCl₃] | glassy |
| A-10 | 1.75(6H, s), 2.23(3H, s), 4.06(2H, s), 6.97~7.82(6H, m), 9.75(1H, bs) | glassy |
| A-11 | [CDCl₃] 1.57(6H, s), 2.23(3H, s), 2.63(3H, s), 4.20(2H, s), 7.40(5H, bs), 12.1(1H, s) | m.p. 232~234° C. |
| A-12 | [CDCl₃] 1.66(6H, s), 2.13(3H, s), 3.94(2H, s), 7.35~8.01(9H, m), 10.56(1H, bs) | m.p. 230~233° C. |
| A-13 | [CDCl₃] 1.46(6H, s), 1.78(3H, s), 2.54(2H, t, J=7Hz), 3.52(2H, t, J=7Hz), 6.71~7.62(8H, m), 7.99(1H, s) | m.p. 176~178° C. |
| A-14 | [CDCl₃] 1.02(3H, t, J=8Hz), 1.52(6H, s), 2.11(2H, q, J=8Hz), 2.57(2H, t, J=6Hz), 3.55(2H, t, J=6Hz), 6.90~7.68(8H, m), 7.93(1H, bs) | m.p. 123~125° C. |
| A-15 | [CDCl₃] 1.66(6H, s), 2.26(3H, s), 4.11(2H, s), 6.84~8.89(7H, m), 10.95(1H, bs), | glassy |
| A-16 | [CDCl₃] 1.65(6H, s), 2.15(3H, s), 4.24(2H, s), 7.10~7.71(5H, m), 12.4(1H, bs) | m.p. 171~175° C. |
| A-17 | [CDCl₃] 1.46(9H, s), 1.70(6H, s), 2.14(3H, s), 4.25(2H, s), 7.25~8.20(5H, m), 11.46(1H, bs) | m.p. 146~148° C. |
| A-18 | [CDCl₃] 1.41(3H, t, J=7Hz), 1.59(6H, s), 2.17(3H, s), 3.16(2H, q, J=7Hz), 4.12(2H, s), 7.20~7.61(5H, m), 11.98(1H, s) | m.p. 185~186° C. |
| A-19 | [CDCl₃] 1.32(3H, t, J=7Hz), 1.61(6H, s), 2.21(3H, s), 3.25(2H, q, J=7Hz), 4.19(2H, s), 7.29~7.66(5H, m), 12.69(1H, bs) | m.p. 226~228° C. |
| A-20 | [d₆-DMSO] 1.38(3H, t, J=7Hz), 1.61(6H, s), 2.11(3H, s), 3.33(2H, q, J=7Hz), 4.14(2H, s), 7.21~7.88(5H, m), 12.48(1H, bs) | glassy |
| A-21 | [CDCl₃] 0.90~1.29(5H, m), 1.61(6H, s), 2.13(3H, s), 4.09(2H, s), 7.09~7.61(5H, m), 11.57(1H, bs) | m.p. 220~223° C. |
| A-22 | [CDCl₃] 1.51(6H, s), 2.13(3H, s), 3.79(2H, s), 7.17(1H, s), 7.09~7.66(5H, m), 11.00(1H, bs) | viscous liquid |
| A-23 | [CDCl₃] 1.66(6H, s), 2.09(3H, s), 2.20(3H, s), 4.01(2H, s), 6.35(1H, bs), 7.12~7.81(5H, m), 10.06(1H, bs) | m.p. 114~116° C. |
| A-24 | [CDCl₃] 1.46(6H, s), 1.91(3H, s), 2.50(2H, t, J=7Hz), 3.48(2H, t, J=7Hz), 6.26~7.60(6H, m), 8.18(1H, s) | glassy |
| A-25 | [CDCl₃] 1.46(6H, s), 1.83(3H, s), 2.50(2H, t, J=7Hz), 3.45(2H, t, J=7Hz), 6.79~7.40(6H, m), 7.92(1H, s) | m.p. 105~108° C. |
| A-26 | [CDCl₃] 1.63(6H, s), 2.09(3H, s), 3.78(2H, s), 3.89(2H, s), 6.73~7.62(8H, m), 10.20(1H, bs) | m.p. 203~206° C. |
| A-27 | [CDCl₃] 1.59(6H, s), 2.13(3H, s), 2.34(3H, s), 3.85(2H, s), 6.80~7.85(6H, m), 10.70(1H, bs) | m.p. 214~216° C. |

TABLE 2-A-continued

| Compound No. | $^1$H—NMRδ (ppm) (Solvent) | Physical property |
|---|---|---|
| A-28 | [CDCl$_3$]<br>1.47(6H, s), 2.08(3H, s),<br>3.85(2H, s), 7.20(1H, s),<br>7.22~8.20(5H, m) | glassy |
| A-29 | [CDCl$_3$]<br>1.67(6H, s), 2.15(6H, s),<br>2.25(3H, s), 3.49(2H, s),<br>6.18~7.09(5H, m), 9.08(1H, bs) | m.p. 225~227° C. |
| A-30 | [CDCl$_3$]<br>1.56(6H, s), 2.00(3H, s),<br>2.61(2H, t, J=7Hz),<br>3.55(2H, t, J=7Hz),<br>6.80~7.52(5H, m), 8.25(1H, bs),<br>8.94~9.08(1H, m) | m.p. 186~189° C. |
| A-31 | [CDCl$_3$]<br>1.49(6H, s), 1.80(3H, s),<br>2.59(2H, t, J=6.5Hz),<br>3.55(2H, t, J=6.5Hz),<br>6.84~7.48(7H, m), 7.91(1H, s) | m.p. 178~180° C. |
| A-32 | [CDCl$_3$]<br>1.68(6H, s), 2.21(3H, s),<br>4.02(2H, s), 6.98~7.70(8H, m),<br>9.70(1H, bs) | m.p. 244~249° C. |
| A-33 | [CDCl$_3$]<br>1.56(6H, s), 2.01(3H, s),<br>3.92(2H, s), 6.79~7.51(5H, m),<br>10.80(1H, bs), | glassy |
| A-34 | [CDCl$_3$]<br>1.56(6H, s), 1.83(3H, s),<br>2.64(2H, t, J=7Hz),<br>3.59(2H, t, J=7Hz),<br>6.77~7.39(6H, m), 8.32(1H, bs),<br>8.47~8.63(1H, m) | m.p. 224~226° C. |
| A-35 | [CDCl$_3$]<br>1.55(6H, s), 1.82(3H, s),<br>2.57(2H, t, J=7Hz),<br>3.52(2H, t, J=7Hz),<br>6.25~6.57(1H, m),<br>6.90~7.45(7H, m), 7.80(1H, bs) | m.p. 154~156° C. |
| A-36 | [CDCl$_3$]<br>1.68(6H, s), 2.12(3H, s),<br>3.93(2H, s), 7.10~7.68(8H, m),<br>10.40(1H, bs) | m.p. 236~241° C. |
| A-37 | [CDCl$_3$]<br>1.69(6H, s), 2.14(3H, s),<br>3.95(2H, s), 6.95~7.35(9H, m) | m.p. > 250° C. |
| A-38 | [CDCl$_3$]<br>1.66(6H, s), 2.13(3H, s),<br>3.96(2H, s), 7.26(5H, s),<br>8.07(1H, s), 10.98(1H, bs) | m.p. 173~182° C. |
| A-39 | [CDCl$_3$]<br>1.26(6H, s), 1.70(3H, s),<br>2.14(9H, s), 4.02(2H, s),<br>6.42(1H, s), 7.20~7.43(6H, m) | m.p. 179~181° C. |
| A-40 | [CDCl$_3$]<br>1.50(6H, s), 1.75(3H, s),<br>2.56(2H, t, J=7Hz),<br>3.50(2H, t, J=7Hz),<br>6.15~7.38(7H, m), 7.80(1H, bs) | m.p. 141~144° C. |
| A-41 | [CDCl$_3$]<br>1.57(6H, s), 2.13(3H, s),<br>3.70(3H, s), 4.02(2H, s),<br>7.27(5H, s), | m.p. 136~142° C. |
| A-42 | [CDCl$_3$]<br>1.56(6H, s), 2.16(3H, s),<br>4.13(2H, s), 7.24(6H, s) | m.p. 219~220° C. |
| A-43 | [CDCl$_3$]<br>1.56(6H, s), 1.73(3H, s),<br>2.57(2H, t, J=7Hz),<br>3.53(2H, t, J=7Hz),<br>6.95~7.55(7H, m), 7.94(1H, bs) | m.p. 163~165° C. |
| A-44 | [CDCl$_3$]<br>1.55(6H, s), 2.14(3H, d, J=1Hz),<br>2.17(3H, s), 3.95(2H, s),<br>7.12~7.43(5H, m), 9.90(1H, bs) | m.p. 221~223° C. |
| A-45 | [CDCl$_3$]<br>1.54(6H, s), 2.13(3H, s),<br>4.04(2H, s), 7.03~7.55(5H, m),<br>7.85(1H, d, J=3Hz),<br>8.00(1H, d, J=3Hz),<br>8.35(1H, d, J=3Hz), 9.78(1H, bs) | glassy |
| A-46 | [CDCl$_3$]<br>1.68(6H, s), 2.18(3H, s),<br>2.24(3H, s), 4.03(2H, s),<br>7.40(6H, s) | m.p. 187~190° C. |
| A-47 | [CDCl$_3$]<br>1.53(6H, s), 1.80(3H, s),<br>2.60(2H, t, J=7Hz),<br>3.55(2H, t, J=7Hz),<br>6.83~8.02(9H, m) | m.p. 172~174° C. |
| A-48 | [CDCl$_3$]<br>1.65(6H, s), 1.97(3H, d, J=3Hz),<br>4.16(2H, s), 6.80~7.40(5H, m) | m.p. 204~208° C. |
| A-49 | [CDCl$_3$]<br>1.57(6H, s), 2.00(3H, s),<br>3.13(2H, t, J=9Hz),<br>3.74(2H, t, J=9Hz), 3.99(2H, s),<br>7.00~7.62(6H, m) | m.p. 83~88° C. |
| A-50 | [CDCl$_3$]<br>1.72(6H, s), 2.20(3H, s),<br>4.09(2H, s), 7.10~7.59(5H, m),<br>8.12~8.36(2H, m), 9.07(1H, bs),<br>9.55~9.69(1H, m) | m.p. 137~140° C. |
| A-51 | [CDCl$_3$]<br>1.72(6H, s), 2.14 (3H, s),<br>4.02(2H, s), 6.84(1H, t, J=4Hz),<br>7.11~7.50(5H, m),<br>8.46(2H, d, J=7Hz), 9.45(1H, bs) | glassy |
| A-52 | [CDCl$_3$]<br>1.67(6H, s), 2.19(3H, s),<br>4.09(2H, s), 7.08(1H, s),<br>7.44(5H, bs), 9.55(1H, bs) | m.p. 175~178° C. |
| A-53 | [CDCl$_3$]<br>1.43(6H, s), 1.83(3H, s),<br>2.54(2H, t, J=7Hz),<br>3.55(2H, t, J=7Hz),<br>6.96~7.42(5H, m),<br>7.53(2H, s), 8.07(1H, bs) | m.p. 235~237° C. |
| A-54 | [CDCl$_3$]<br>1.47(6H, s), 1.76(3H, s),<br>2.56(2H, t, J=7Hz),<br>3.51(2H, t, J=7Hz),<br>6.86~7.20(4H, m), 7.44(2H, s),<br>7.79(1H, bs) | m.p. 209~214° C. |
| A-55 | [CDCl$_3$]<br>1.56(6H, s), 1.81(3H, s),<br>2.55(2H, t, J=7Hz),<br>3.51(2H, t, J=7Hz),<br>6.75~7.30(7H, m), 7.81(1H, bs),<br>8.25~8.44(1H, m) | m.p. 199~202° C. |
| A-56 | [CDCl$_3$]<br>1.57(6H, s), 1.82(3H, s),<br>2.61(2H, t, J=7Hz),<br>3.55(2H, t, J=7Hz),<br>6.80~7.35(6H, m), 7.92(1H, bs),<br>8.35~8.55(1H, m) | m.p. 205~207° C. |
| A-57 | [CDCl$_3$]<br>1.76(6H, s), 2.05(3H, d, J=3Hz),<br>2.23(3H, s), 4.10(2H, s),<br>6.90~7.65(5H, m) | m.p. 222~227° C. |
| A-58 | [CDCl$_3$]<br>1.61(6H, s), 2.04(3H, d, J=3Hz),<br>3.95(2H, s), 6.83~7.55(5H, m),<br>10.75(1H, bs) | m.p. 192~195° C. |
| A-59 | [CDCl$_3$]<br>1.17(3H, t, J=7Hz), 1.60(6H, s),<br>2.60(2H, q, J=7Hz), 3.98(2H, s),<br>7.16(1H, s), 7.20~7.63(5H, m),<br>10.70(1H, bs) | m.p. 193~196° C. |
| A-60 | [CDCl$_3$]<br>1.73(6H, s), 2.18(3H, s),<br>3.94 (6H, s), 4.09(2H, s),<br>5.76(1H, s), 7.44(5H, bs),<br>9.13(1H, bs) | glassy |

TABLE 2-A-continued

| Compound No. | $^1$H—NMRδ (ppm) (Solvent) | Physical property |
|---|---|---|
| A-61 | [CDCl$_3$]<br>1.53(6H, s), 1.79(3H, s),<br>2.07(2H, t, J=7Hz),<br>3.55(2H, t, J=7Hz),<br>6.50~7.42(7H, m), 7.96(1H, bs),<br>8.04~8.43(1H, m) | m.p. 174~177° C. |
| A-62 | [CDCl$_3$]<br>1.55(6H, s), 1.79(3H, s),<br>2.58(2H, t, J=7Hz),<br>3.50(2H, t, J=7Hz),<br>6.32~7.36(6H, m), 7.85(1H, bs),<br>7.85~8.15(1H, m) | m.p. 156~160° C. |
| A-63 | [CDCl$_3$]<br>1.50(6H, s), 1.81(3H, s),<br>2.59(2H, t, J=7Hz),<br>3.51(2H, t, J=7Hz),<br>6.61~7.30(6H, m), 7.69(1H, bs) | m.p. 150~154° C. |
| A-64 | [CDCl$_3$]<br>1.57(6H, s), 1.80(3H, s),<br>2.57(2H, t, J=7Hz),<br>3.53(2H, t, J=7Hz),<br>6.46~7.30(7H, m),<br>7.95~8.30(2H, m) | m.p. 204~205° C. |
| A-65 | [CDCl$_3$]<br>1.57(6H, s), 1.83(3H, s),<br>2.63(2H, t, J=7Hz),<br>3.58(2H, t, J=7Hz),<br>6.45~7.43(6H, m),<br>8.13~8.45(2H, m) | m.p. 177~180° C. |
| A-66 | [CDCl$_3$]<br>1.69(6H, s), 2.07(3H, d, J=3Hz),<br>2.26(3H, s), 4.10(2H, s),<br>6.85~7.65(5H, m) | m.p. 212~216° C. |
| A-67 | [CDCl$_3$]<br>1.76(6H, s), 2.13(3H, s),<br>3.65(3H, s), 4.07(2H, s),<br>6.25(1H, s),<br>7.05~7.51(5H, m), 10.31(1H, bs) | m.p. 188~190° C. |
| A-68 | [CDCl$_3$]<br>1.71(6H, s), 2.19(3H, s),<br>3.70(3H, s), 4.08(2H, s),<br>7.24~7.51(5H, m),<br>8.63(1H, bs) | viscous oil |
| A-69 | [CDCl$_3$]<br>1.56(6H, s), 1.83(3H, s),<br>2.65(2H, t, J=7Hz),<br>3.57(2H, t, J=7Hz),<br>6.78~7.68(5H, m),<br>8.24~8.57(2H, m) | m.p. 191~198° C. |
| A-70 | [CDCl$_3$]<br>1.71(6H, s), 2.17(3H, s),<br>3.76(3H, s), 4.06(2H, s),<br>6.70(1H, d, J=2Hz),<br>7.23(1H, d, J=2Hz),<br>7.43(5H, s), 8.80(1H, bs) | m.p. 167~169° C. |
| A-71 | [CDCl$_3$]<br>1.75(6H, s), 2.15(3H, s),<br>2.19(3H, s), 3.69(3H, s),<br>4.09(2H, s), 6.14(1H, s),<br>7.44(5H, s), 9.90(1H, bs) | m.p. 198~200° C. |
| A-72 | [CDCl$_3$]<br>1.59(6H, s), 1.84(3H, s),<br>2.63(2H, t, J=7Hz),<br>3.60(2H, t, J=7Hz),<br>6.92~7.68(5H, m),<br>8.38(1H, bs), 8.58~9.03(2H, m) | m.p. 148~151° C. |
| A-73 | [CDCl$_3$]<br>1.54(6H, s), 1.80(3H, s),<br>2.57(2H, t, J=7Hz),<br>3.54(2H, t, J=7Hz),<br>6.96~8.14(10H, m) | m.p. 186~189° C. |
| A-74 | [CDCl$_3$]<br>1.47(6H, s), 1.81(3H, s),<br>2.59(2H, t, J=7Hz),<br>3.57(2H, t, J=7Hz),<br>6.86~7.30(5H, m), 7.38(1H, s),<br>7.93(2H, s), 8.37(1H, s) | m.p. 214~215° C. |
| A-75 | [CDCl$_3$]<br>1.50(6H, s), 1.82(3H, s),<br>2.66(2H, t, J=7Hz),<br>3.60(2H, t, J=7Hz),<br>6.90~7.35(4H, m),<br>7.45(1H, s), 7.93(2H, s),<br>8.27(1H, s) | m.p. 199~201° C. |
| A-76 | [CDCl$_3$]<br>1.58(6H, s), 2.19(3H, s),<br>4.17(2H, s), 7.34(5H, s),<br>12.20(1H, bs) | m.p. 215~219° C. |
| A-77 | [CDCl$_3$]<br>1.65(6H, s), 2.08(3H, d, J=3Hz),<br>4.27(2H, s), 6.65~7.75(4H, m),<br>12.20(1H, bs) | m.p. 211~214° C. |
| A-78 | [CDCl$_3$]<br>1.58(6H, s), 1.80(3H, s),<br>2.58(2H, t, J=7Hz),<br>3.56(2H, t, J=7Hz,),<br>6.82~7.62(5H, m),<br>7.84~8.21(2H, m),<br>8.61~8.78(1H, m), 8.85(1H, bs) | m.p. 139~142° C. |
| A-79 | [CDCl$_3$]<br>1.55(6H, s), 1.80(3H, s),<br>2.60(2H, t, J=7Hz),<br>3.53(2H, t, J=7Hz),<br>6.70~7.33(4H, m),<br>7.75~8.03(2H, m),<br>8.55~8.66(1H, m), 8.70(1H, bs) | m.p. 143~145° C. |
| A-80 | [CDCl$_3$]<br>1.01(3H, t, J=7Hz), 1.53(6H, s),<br>2.10(2H, q, J=7Hz),<br>2.57(2H, t, J=7Hz),<br>3.54(2H, t, J=7Hz),<br>6.15~6.67(1H, m)<br>6.88~7.44(7H, m), 8.05(1H, bs) | m.p. 125~128° C. |
| A-81 | [CDCl$_3$]<br>1.02(3H, t, J=7Hz), 1.54(6H, s),<br>2.12(2H, q, J=7Hz),<br>2.61(2H, t, J=7Hz),<br>3.57(2H, t, J=7Hz),<br>6.20~6.78(1H, m),<br>6.83~7.34(6H, m), 7.95(1H, bs) | m.p. 152~155° C. |
| A-82 | [CDCl$_3$]<br>1.52(6H, s), 1.79(3H, s),<br>2.57(2H, t, J=7Hz),<br>3.56(2H, t, J=7Hz),<br>6.81~7.45(8H, m),<br>7.62(1H, bs), 7.84(1H, bs) | m.p. 166~168° C. |
| A-83 | [CDCl$_3$]<br>1.54(6H, s), 1.80(3H, s),<br>2.60(2H, t, J=7Hz),<br>3.57(2H, t, J=7Hz),<br>6.84~7.47(7H, m),<br>7.61(1H, bs), 7.74(1H, bs) | m.p. 179~181° C. |
| A-84 | [CDCl$_3$]<br>1.54(6H, s), 1.73(3H, s),<br>2.58(2H, t, J=7Hz),<br>3.56(2H, t, J=7Hz),<br>6.87~7.41(7H, m),<br>7.61(1H, bs), 7.87(1H, bs) | m.p. 202~205° C. |
| A-85 | [CDCl$_3$]<br>1.57(6H, s), 1.76(3H, s),<br>2.63(2H, t, J=7Hz),<br>3.59(2H, t, J=7Hz),<br>6.76~7.47(6H, m),<br>7.92(1H, bs), 8.33~8.65(1H, m) | m.p. 223~225° C. |
| A-86 | [CDCl$_3$]<br>1.57(6H, s), 1.76(3H, s),<br>2.63(2H, t, J=7Hz),<br>3.59(2H, t, J=7Hz),<br>6.43~7.85(6H, m),<br>7.86~8.43(2H, m) | m.p. 195~196° C. |
| A-87 | [CDCl$_3$]<br>1.56(6H, s), 1.74(3H, s),<br>2.61(2H, t, J=7Hz),<br>3.58(2H, t, J=7Hz), | m.p. 173~175° C. |

TABLE 2-A-continued

| Compound No. | $^1$H—NMRδ (ppm) (Solvent) | Physical property |
|---|---|---|
| | 7.02~7.70(7H, m),<br>7.74(1H, s), 7.97(1H, bs)<br>[CDCl$_3$] | |
| A-88 | 1.58(6H, s), 1.77(3H, s),<br>2.67(2H, t, J=7Hz),<br>3.67(2H, t, J=7Hz),<br>6.98~7.54(4H, m),<br>7.97~8.26(2H, m),<br>8.74~8.86(1H, bs), 8.90(1H, bs)<br>[CDCl$_3$] | m.p. 151~154° C. |
| A-89 | 1.77(6H, s), 2.16(3H, s),<br>3.80(3H, s), 4.12(2H, s),<br>6.66(1H, s), 7.43(5H, s),<br>[CDCl$_3$] | glassy |
| A-90 | 1.21(6H, d, J=7Hz), 1.57(6H, s),<br>1.78(3H, s), 2.54(2H, t, J=7Hz),<br>2.86(1H, sept, J=7Hz),<br>3.53(2H, t, J=7Hz),<br>6.78~7.46(9H, m), 7.73(1H, bs)<br>[CDCl$_3$] | m.p. 151~155° C. |
| A-91 | 1.57(6H, s), 1.84(3H, s),<br>2.65(2H, t, J=7Hz),<br>3.59(2H, t, J=7Hz),<br>6.53~7.43(5H, m),<br>7.77~8.39(2H, m)<br>[CDCl$_3$] | m.p. 122~125° C. |
| A-92 | 1.57(6H, s), 1.85(3H, s),<br>2.66(2H, t, J=7Hz),<br>3.58(2H, t, J=7Hz),<br>6.63~7.42(5H, m),<br>7.87(1H, bs), 8.32~8.58(1H, m)<br>[CDCl$_3$] | m.p. 192~194° C. |
| A-93 | 1.50(6H, s), 1.77(3H, s),<br>2.56(2H, t, J=7Hz),<br>3.48(2H, t, J=7Hz),<br>6.47~7.56(6H, m),<br>7.64(1H, s), 7.79(1H, s)<br>[CDCl$_3$] | m.p. 170~172° C. |
| A-94 | 1.47(6H, s), 1.76(3H, s),<br>2.53(2H, t, J=6.5Hz),<br>3.50(2H, t, J=6.5Hz),<br>6.48(1H, t, J=74Hz),<br>6.59~7.64(9H, m), 7.99(1H, s)<br>[CDCl$_3$] | m.p. 130~132° C. |
| A-95 | 1.50(6H, s), 1.80(3H, s),<br>2.60(2H, t, J=7Hz),<br>3.56(2H, t, J=7Hz),<br>6.93~7.74(8H, m),<br>7.85(1H, bs), 8.14(1H, bs)<br>[CDCl$_3$] | m.p. 171~175° C. |
| A-96 | 1.54(6H, s), 1.81(3H, s),<br>2.63(2H, t, J=7Hz),<br>3.57(2H, t, J=7Hz),<br>6.76~7.70(7H, m),<br>7.84(1H, bs), 7.98(1H, bs)<br>[CDCl$_3$] | m.p. 162~166° C. |
| A-97 | 1.55(6H, s), 1.74(3H, s),<br>2.60(2H, t, J=7Hz),<br>3.56(2H, t, J=7Hz),<br>6.98~7.67(7H, m),<br>7.71(1H, bs), 7.89(1H, bs)<br>[CDCl$_3$] | m.p. 144~147° C. |
| A-98 | 1.53(6H, s), 1.80(3H, s),<br>2.56(2H, t, J=7Hz),<br>3.53(2H, t, J=7Hz),<br>6.94~7.55(8H, m),<br>7.63~7.87(2H, m)<br>[CDCl$_3$] | m.p. 174~176° C. |
| A-99 | 1.55(6H, s), 1.81(3H, s),<br>2.61(2H, t, J=7Hz),<br>3.57(2H, t, J=7Hz),<br>6.86~7.53(7H, m),<br>7.65~7.87(2H, m)<br>[CDCl$_3$] | m.p. 190~192° C. |
| A-100 | 1.55(6H, s), 1.76(3H, s),<br>2.25(3H, s),<br>2.49(2H, t, J=7Hz), | m.p. 136~138° C. |
| | 3.48(2H, t, J=7Hz),<br>6.62~7.35(9H, m), 7.64(1H, bs)<br>[CDCl$_3$] | |
| A-101 | 1.55(6H, s), 1.77(3H, s),<br>2.24(3H, s),<br>2.52(2H, t, J=7Hz),<br>3.48(2H, t, J=7Hz),<br>6.69~7.20(8H, m), 7.56(1H, bs)<br>[CDCl$_3$] | m.p. 164~167° C. |
| A-102 | 1.56(6H, s), 1.97(3H, s),<br>2.57(2H, t, J=7Hz),<br>3.53(2H, t, J=7Hz),<br>6.81~8.02(8H, m)<br>[CDCl$_3$] | m.p. 174~177° C. |
| A-103 | 1.57(6H, s), 2.00(3H, s),<br>2.60(2H, t, J=7Hz),<br>3.55(2H, t, J=7Hz),<br>6.42~7.44(5H, m), 7.93(1H, bs),<br>8.04~8.39(1H, m)<br>[CDCl$_3$] | m.p. 142~144° C. |
| A-104 | 1.55(6H, s), 1.80(3H, s),<br>2.57(2H, t, J=7Hz),<br>3.54(2H, t, J=7Hz),<br>6.50~7.56(9H, m), 7.87(1H, bs)<br>[CDCl$_3$] | m.p. 147~149° C. |
| A-105 | 1.53(6H, s), 1.79(3H, s),<br>2.57(2H, t, J=7Hz),<br>3.53(2H, t, J=7Hz),<br>6.50~7.64(8H, m), 7.86(1H, bs)<br>[CDCl$_3$] | m.p. 135~137° C. |
| A-106 | 1.52(6H, s), 1.82(3H, s),<br>2.60(2H, t, J=7Hz),<br>3.57(2H, t, J=7Hz),<br>6.72~7.81(8H, m), 8.08(1H, bs)<br>[CDCl$_3$] | m.p. 138~139° C. |
| A-107 | 1.58(6H, s), 1.80(3H, s),<br>2.56(2H, t, J=7Hz),<br>3.54(2H, t, J=7Hz), 3.76(3H, s),<br>6.44~7.37(9H, m), 7.77(1H, bs)<br>[CDCl$_3$] | m.p. 116~118° C. |
| A-108 | 1.56(6H, s), 1.79(3H, s),<br>2.57(2H, t, J=7Hz),<br>3.53(2H, t, J=7Hz), 3.76(3H, s),<br>6.44~7.50(8H, m), 7.74(1H, bs)<br>[CDCl$_3$] | m.p. 132~135° C. |
| A-109 | 1.55(6H, s), 1.81(3H, s),<br>2.57(2H, t, J=7Hz),<br>3.54(2H, t, J=7Hz),<br>6.72~7.91(10H, m)<br>[CDCl$_3$] | m.p. 172~176° C. |
| A-110 | 1.53(6H, s), 1.80(3H, s),<br>2.58(2H, t, J=7Hz),<br>3.54(2H, t, J=7Hz),<br>6.73~7.92(9H, m)<br>[CDCl$_3$] | m.p. 180~181° C. |
| A-111 | 1.56(6H, s), 1.81(3H, s),<br>2.27(3H, s),<br>2.58(2H, t, J=7Hz),<br>3.55(2H, t, J=7Hz),<br>6.59~7.42(6H, m), 7.77(1H, bs),<br>7.95~8.20(2H, m)<br>[CDCl$_3$] | m.p. 192~195° C. |
| A-112 | 1.56(6H, s), 1.79(3H, s),<br>2.23(3H, s),<br>2.56(2H, t, J=7Hz),<br>3.51(2H, t, J=7Hz),<br>6.60~7.39(5H, m), 7.75(1H, bs),<br>7.93~8.20(2H, m)<br>[CDCl$_3$] | m.p. 196~200° C. |
| A-113 | 1.72(6H, s), 2.19(3H, s),<br>2.49(3H, s), 4.07(2H, s),<br>7.40(5H, s), 10.85(1H, bs)<br>[CDCl$_3$] | m.p. 245~248° C. |
| A-114 | 1.69(6H, s), 2.20(3H, s),<br>4.08(2H, s), 7.20~7.50(6H, m),<br>10.00(1H, bs)<br>[CDCl$_3$] | m.p. 195~201° C. |

TABLE 2-A-continued

| Compound No. | ¹H—NMRδ (ppm) (Solvent) | Physical property |
|---|---|---|
| A-115 | 1.69(6H, s), 2.09(3H, s), 4.14(2H, s), 6.80~7.65(5H, m), 10.20(1H, bs) [CDCl₃] | m.p. 160~164° C. |
| A-116 | 1.64(6H, s), 2.22(3H, s), 4.09(2H, s), 7.43(6H, s), 9.95(1H, bs) [CDCl₃] | m.p. 190~194° C. |
| A-117 | 1.14(3H, t, J=7Hz), 1.67(6H, s), 2.16(3H, s), 2.24(3H, s), 2.52(2H, q, J=7Hz), 4.00(2H, s), 7.10~7.49(5H, m), 9.25(1H, bs) [CDCl₃] | m.p. 201~203° C. |
| A-118 | 1.58(6H, s), 1.84(3H, s), 2.63(2H, t, J=7Hz), 3.59(2H, t, J=7Hz), 6.95~7.50(6H, m), 8.36(1H, bs), 8.60~8.84(2H, m) [CDCl₃] | m.p. 155~162° C. |
| A-119 | 1.54(6H, s), 1.80(3H, s), 2.59(2H, t, J=7Hz), 3.52(2H, t, J=7Hz), 6.95~7.36(8H, m), 8.25(1H, bs) [CDCl₃] | m.p. 187~188° C. |
| A-120 | 1.49(6H, s), 1.81(3H, s), 2.60(2H, t, J=7Hz), 3.57(2H, t, J=7Hz), 6.79~7.75(7H, m), 8.12(1H, s) [CDCl₃] | glassy |
| A-121 | | |
| A-122 | | |
| A-122 | | |
| A-123 | | |
| A-124 | | |
| A-125 | | |
| A-126 | | |
| A-127 | | |
| A-128 | | |
| A-129 | | |
| A-130 | | |
| A-131 | | |
| A-132 | | |

TABLE 2-B

| Compound No. | ¹H-NMR δ (ppm) (Solvent) Physical property |
|---|---|
| B-1 | 1.46(6H, s), 2.05~2.23(2H, m), 3.36~3.75(4H, m), 7.23(5H, s) [CDCl₃ + DMSO – d₆] m.p. 218~220° C. |
| B-2 | 1.51(6H, s), 2.03~2.25(2H, m), 3.33~3.73(4H, m), 6.95(1H, t, J=2Hz), 7.19~7.47(7H, m), 8.16(1H, s) [CDCl₃] viscous liquid |
| B-3 | 1.56(6H, s), 2.10~2.32(2H, m), 3.40~3.79(4H, m), 6.95~7.21(7H, m), 8.40(1H, s), 8.52~8.59(1H, m) [CDCl₃] m.p. 148~151° C. |
| B-4 | 1.50(6H, s), 2.05~2.35(2H, m), 3.40~3.80(4H, m), 7.21(6H, s), 11.10(1H, s) [CDCl₃ + DMSO – d₆] m.p. 225~228° C. |
| B-5 | 1.46(6H, s), 2.05~2.35(2H, m), 3.40~3.65(4H, m), 6.95~7.35(4H, m) [CDCl₃ + DMSO – d₆] m.p. 209~211° C. |
| B-6 | 1.53(6H, s), 2.10~2.30(2H, m), 3.35~3.70(4H, m), 6.95~7.20(5H, m), 7.46(2H, d, J=2Hz), 8.14(1H, s) [CDCl₃] m.p. 159~161° C. |
| B-7 | 1.55(6H, s), 2.19~2.34(2H, m), |

TABLE 2-B-continued

| Compound No. | ¹H-NMR δ (ppm) (Solvent) Physical property |
|---|---|
| | 3.40~3.69(4H, m), 6.94~7.29(6H, m), 8.39~8.55(2H, m) [CDCl₃] m.p. 169~171° C. |
| B-8 | 1.49(6H, s), 2.05~2.40(2H, m), 3.45~3.70(4H, m), 7.08~7.19(5H, m), 11.11(1H, s) [CDCl₃ + DMSO – d₆] m.p. 219~221° C. |
| B-9 | 1.56(6H, s), 2.05~2.35(2H, m), 3.40~3.71(4H, m), 6.55~7.17(6H, m), 8.07~8.40(2H, m) [CDCl₃] m.p. 142~144° C. |
| B-10 | 1.52(6H, s), 2.05~2.31(2H, m), 3.40~3.80(4H, m), 7.10~7.25(6H, m), 8.17 (1H, ddd, J=8, 3, 0, 3Hz), 8.54~8.59(1H, m), 8.96~9.02(1H, m) [CDCl₃ + DMSO – d₆] m.p. 200~202° C. |
| B-11 | 1.50(6H, s), 2.00~2.20(2H, m), 3.29~3.70(4H, m), 7.13~7.62(6H, m), 8.13(1H, d, J=2Hz), 8.33(1H, d, J=4Hz) [CDCl₃] glassy |
| B-12 | 1.54(6H, s), 2.04~2.29(2H, m), 3.38~3.78(4H, m), 7.05~7.25(6H, m), 8.00(1H, dd, J=5, 2Hz), 8.40(1H, s), 8.73(1H, dd, J=8, 2Hz) [CDCl₃] m.p. 176~177° C. |
| B-13 | 1.59(6H, s), 2.04~2.25(2H, m), 3.52~3.71(4H, m), 7.19(5H, s), 11.47(1H, s) [CDCl₃] m.p. 232~234° C. |
| B-14 | 1.43(6H, s), 2.09~2.27(2H, m), 3.30~3.75(4H, m), 7.17(5H, s), 7.89(2H, s), 9.30(1H, s) [CDCl₃ + DMSO – d₆] m.p. 202~205° C. |
| B-15 | 1.56(6H, s), 2.05~2.35(2H, m), 3.38~3.78(4H, m), 6.88~7.26(6H, m), 8.06~8.12(1H, m), 8.44~8.57(1H, m) [CDCl₃] m.p. 120~122° C. |
| B-16 | 1.56(6H, s), 2.02~2.81(2H, m), 3.37~3.84(4H, m), 3.91(6H, s), 5.70(1H, s), 7.22~7.28(5H, m), 8.25(1H, s) [CDCl₃] glassy |
| B-17 | 1.53(6H, s), 2.05~2.32(2H, m), 3.35~3.78(4H, m), 7.18(5H, s), 8.15~8.60(3H, m), 8.79(1H, s) [CDCl₃] m.p. 195~197° C. |
| B-18 | 1.53(6H, s), 2.06(6H, s), 2.06~2.28(2H, m), 3.39~3.78(4H, m), 3.64(3H, s), 7.24(5H, s), 7.67(1H, s) [CDCl₃ + DMSO – d₆] m.p. 185~188° C. |
| B-19 | 1.59(6H,s), 2.14~2.35(2H, m), 3.44~3.82(4H, m), 7.22(5H, s), 7.53~7.95(2H, m), 8.57(1H, s), 9.38(1H, d, J=3Hz) [CDCl₃] m.p. 180~182° C. |
| B-20 | 1.61(6H, s), 2.05~2.32(2H, m), 3.38~3.74(4H, m), 7.10~7.38(8H, m) [CDCl₃] m.p. 144~147° C. |
| B-21 | 1.55(6H, s), 2.08~2.27(2H, m), 3.36~3.77(4H, m), 6.25~6.65(1H, m), 7.00~7.25(1H, m), 8.19(1H, s) [CDCl₃] m.p. 147~149° C. |

TABLE 2-B-continued

| Compound No. | ¹H-NMR δ (ppm) (Solvent) Physical property |
|---|---|
| B-22 | 1.55(6H, s), 2.05~2.35(2H, m), 3.35~3.65(4H, m), 6.25~6.65(1H, m), 7.01~7.15(6H, m), 8.18(1H, s) [CDCl$_3$] m.p. 141~143° C. |
| B-23 | 1.57(6H, s), 2.10~2.33(2H, m), 3.41~3.81(4H, m), 6.60(1H, ddd, J=9.5, 8.5, 3Hz), 7.22(5H, s), 8.15(1H, ddd, J=12, 3, 2Hz), 8.53(1H, s) [CDCl$_3$] m.p. 173~174° C. |
| B-24 | 1.57(6H, s), 2.15~2.36(2H, m), 3.42~3.72(4H, m), 6.56(1H, ddd, J=9.5, 8.5, 3Hz), 6.95~7.25(4H, m), 8.15(1H, ddd, J=12, 3, 2Hz), 8.45(1H, s) [CDCl$_3$] m.p. 184~185° C. |
| B-25 | 1.55(6H, s), 2.05~2.32(2H, m), 3.39~3.79(4H, m), 7.09~7.28(6H, m), 8.47~8.52(2H, m) [CDCl$_3$] m.p. 186~188° C. |
| B-26 | 1.56(6H, s), 2.10~2.40(2H, m), 3.42~3.65(4H, m), 7.06~7.18(5H, m), 8.47~8.52(2H, m) [CDCl$_3$] m.p. 185~187° C. |
| B-27 | 1.56(6H,s), 2.00~2.29(2H, m), 3.37~3.77(4H, m), 6.50~7.10(2H, m), 7.21(5H, s), 7.95~8.35(2H, m) [CDCl$_3$] m.p. 131~133° C. |
| B-28 | 1.56(6H, s), 2.05~2.31(2H, m), 3.40~3.79(4H, m), 6.45~6.75(1H, m), 7.10~7.20(6H, m), 8.10~8.45(2H, m) [CDCl$_3$] m.p. 142~144° C. |
| B-29 | 1.57(6H, s), 2.05~2.31(2H, m), 3.39~3.80(4H, m), 6.70~7.05(1H, m), 7.24(5H, s), 7.95~8.55(2H, m) [CDCl$_3$] m.p. 142~144° C. |
| B-30 | 1.55(6H, s), 2.09~2.29(2H, m), 3.37~3.77(4H, m), 7.20(5H, s), 7.95~8.25(2H, m) [CDCl$_3$] m.p. 153~154° C. |
| B-31 | 1.53(6H, s), 2.10~2.32(2H, m), 3.37~3.80(4H, m), 7.16~7.32(5H, m), 8.33(1H, d, J=1Hz), 8.55(1H, s), 8.61(1H, d, J=1Hz) [CDCl$_3$] glassy |
| B-32 | 1.57(6H, s), 2.05~2.27(2H, m), 3.36~3.77(4H, m), 7.22~7.82(9H, m), 8.17(1H, s) [CDCl$_3$] m.p. 139~142° C. |
| B-33 | 1.57(6H, s), 2.10~2.32(2H, m), 3.40~3.80(4H, m), 7.11~7.38(7H, m), 8.55(1H, s), 8.85(1H, d, J=1Hz) [CDCl$_3$] m.p. 148~149° C. |
| B-34 | 1.53(6H, s), 2.00~2.27(2H, m), 3.36~3.76(4H, m), 7.15~7.88(9H, m), 8.24(1H, s) [CDCl$_3$] glassy |
| B-35 | 1.51(6H, s), 2.00~2.30(2H, m), 3.34~3.79(4H, m), 7.22(5H, s), 8.23(1H, s), 8.46(1H, s) [CDCl$_3$] glassy |
| B-36 | 1.57(6H, s), 2.05~2.35(2H, m), 3.35~3.70(4H, m), 6.87~7.25(6H, m), 8.05(1H, brs), 8.35~8.50(1H, m) [CDCl$_3$] m.p. 163~164° C. |
| B-37 | 1.58(6H, s), 2.10~2.45(2H, m), 3.42~3.75(4H, m), 6.45~6.70(1H, m), 7.08~7.35(5H, m), 8.15~8.45(2H, m) [CDCl$_3$] m.p. 147~149° C. |
| B-38 | 1.56(6H, s), 2.05~2.30(2H, m), 3.41~3.71(4H, m), 6.80~7.35(5H, m), 7.90~8.60(2H, m) [CDCl$_3$] m.p. 160~162° C. |
| B-39 | 1.56(6H, s), 2.14~2.33(2H, m), 3.41~3.81(4H, m), 6.85~7.39(7H, m), 8.40(1H, s), 8.69(1H, d, J=2Hz) [CDCl$_3$] m.p. 177~178° C. |
| B-40 | 1.59(6H, s), 2.05~2.40(2H, m), 3.40~3.80(4H, m), 7.10~7.25(7H, m), 8.19(1H, brs), 8.76~8.87(1H, m) [CDCl$_3$] m.p. 153~154° C. |
| B-41 | 1.50(6H, s), 2.00~2.21(2H, m), 3.29~3.64(4H, m), 3.64(3H, s), 6.65(1H, d, J=2Hz) 7.10~7.35(6H, m), 8.19(1H, s) [CDCl$_3$] glassy |
| B-42 | 1.52(6H, s), 2.05~2.35(2H, m), 3.38~3.80(4H, m), 3.63(3H, s), 6.03(1H, s), 7.27(5H, s), 8.83(1H, s) [CDCl$_3$ + DMSO – d$_6$] m.p. 201~203° C. |
| B-43 | 1.54(6H, s), 2.05~2.35(2H, m), 3.34~3.74(4H, m), 7.19(5H, s), 8.15~8.24(2H, m), 8.32(1H, s), 9.60(1H, d, J=1Hz) [CDCl$_3$] glassy |
| B-44 | 1.56(6H, s), 2.10~2.30(2H, m), 3.40~3.78(4H, m), 7.20(5H, s), 7.41~7.46(1H, m), 7.96(2H, s), 8.43(1H, s) [CDCl$_3$] m.p. 190~191° C. |
| B-45 | 1.52(6H, s), 2.00~2.35(2H, m), 3.39~3.79(4H, m), 6.89~7.31(8H, m), 8.41(1H, s) [CDCl$_3$ + DMSO – d$_6$] m.p. 210~211° C. |
| B-46 | 1.34(6H, d, J=6Hz), 1.59(6H, s), 2.12~2.33(2H, m), 3.41~3.80(4H, m), 5.23(1H, sept, J=6Hz), 7.15~7.78(7H, m), 8.50(1H, s), 9.09(1H, d, J=2Hz) [CDCl$_3$] m.p. 129~132° C. |
| B-47 | 1.53(6H, s), 2.03~2.35(2H, m), 3.33~3.70(4H, m), 3.70(3H, s), 6.66(1H, d, J=2Hz), 7.13~7.28(6H, m), 8.18(1H, s) [CDCl$_3$] glassy |
| B-48 | 1.60(6H, s), 2.02~2.24(2H, m), 3.36~3.72(4H, m), 3.72(3H, s), 7.19~7.30(6H, m), 7.97(1H, s) [CDCl$_3$] glassy |
| B-49 | 1.52(6H, s), 3.59(2H, t, J=8Hz) 3.89(2H, t, J=8Hz), 6.98~7.01(2H, m), 7.28(2H, t, J=8Hz), 7.54(2H, d, J=8Hz), 7.71(2H, d, J=2Hz), 9.36(1H, s)(500MHz) [CDCl$_3$ + DMSO – d$_6$] m.p. 217~218° C. |
| B-50 | 1.52(6H, s), 3.55~3.90(4H, m), 6.95~7.60(6H, m), 11.59(1H, s) [CDCl$_3$ + DMSO – d$_6$] m.p. 214~215° C. |
| B-51 | 1.59(6H, s), 2.10~2.40(2H, m), 3.40~3.70(4H, m), |

TABLE 2-B-continued

| Compound No. | ¹H-NMR δ (ppm) (Solvent) Physical property |
|---|---|
| B-52 | 7.12~7.80(7H, m),<br>7.82~7.84(1H, m), 8.23(1H, s)<br>[CDCl₃] m.p. 138~140° C.<br>1.56(6H, s), 2.17~2.31(2H, m),<br>3.39~3.69(4H, m),<br>7.00~7.27(6H, m),<br>8.12~8.19(1H, m),<br>8.69~8.84(1H, m)<br>[CDCl₃] m.p 144~146° C. |
| B-53 | 1.18(3H, t, J=7Hz), 1.54(6H, s),<br>1.98~2.18(2H, m),<br>2.57(2H, q, J=7Hz),<br>3.28~3.69(4H, m),<br>6.75~7.39(9H, m), 7.97(1H, s)<br>[CDCl₃] m.p. 113~115° C. |
| B-54 | 1.21(6H, d, J=7Hz), 1.55(6H, s),<br>2.00~2.35(2H, m),<br>2.84(4H, sept, J=7Hz),<br>3.30~3.70(4H, m),<br>6.75~7.43(9H, m), 8.01(1H, s)<br>[CDCl₃] glassy |
| B-55 | 1.55(6H, s), 2.03~2.22(2H, m),<br>3.30~3.74(4H, m),<br>3.68(3H, s), 7.17~7.29(5H, m),<br>7.51(1H, s)<br>[CDCl₃] glassy |
| B-56 | 1.57(6H, s), 1.99~2.48(2H, m),<br>3.42~3.81(4H, m),<br>7.26~7.81(7H, m),<br>8.49(1H, brs), 9.04 (1H, s)<br>[CDCl₃] m.p. 124~126° C. |
| B-57 | 1.54(6H, s), 2.03~2.31(2H, m),<br>3.34~3.76(4H, m),<br>7.17~7.42(1H, s),<br>8.36(1H, s), 9.51(1H, s)<br>[CDCl₃] glassy |
| B-58 | 1.60(6H, s), 2.01~2.35(2H, m),<br>3.36~3.67(4H, m),<br>3.69(3H, s), 6.38(1H, s),<br>7.13~7.30(5H, m), 8.33(1H, brs)<br>[CDCl₃] m.p. 209~211° C. |
| B-59 | 1.54(6H, s), 2.05~2.31(2H, m),<br>3.43~3.81(4H, m),<br>6.82~7.26(7H, m), 8.56(1H, s)<br>[CDCl₃ + DMSO - d₆] m.p. 204~205° C. |
| B-60 | 1.58(6H, s), 2.15~2.45(2H, m),<br>3.44~3.75(4H, m),<br>7.05~7.50(6H, m), 8.55(1H, s),<br>8.82(1H, s)<br>[CDCl₃] m.p. 156~157° C. |
| B-61 | 1.51(6H, s), 2.01~2.30(2H, m),<br>3.32~3.70(4H, m),<br>6.45(1H, t, J=75Hz),<br>6.64~7.53(9H, m),<br>8.11(1H, s)<br>[CDCl₃] m.p. 129~131° C. |
| B-62 | 1.59(6H, s), 2.09~2.40(2H, m),<br>3.41~3.81(4H, m),<br>6.89~7.88(8H, m), 8.34(1H, brs)<br>[CDCl₃] m.p. 128~131° C. |
| B-63 | 1.59(6H, s), 2.05~2.41(2H, m),<br>3.41~3.72(4H, m),<br>6.81~7.80(7H, m), 8.33(1H, s)<br>[CDCl₃] m.p. 126~128° C. |
| B-64 | 1.57(6H, s), 2.14~2.40(2H, m),<br>3.41~3.80(4H, m),<br>7.10~7.48(7H, m), 8.49(1H, s),<br>8.80(1H, d, J=2Hz)<br>[CDCl₃] m.p. 165~166° C. |
| B-65 | 1.53(6H, s), 1.97~2.29(2H, m),<br>2.25(3H, s), 3.29~3.68(4H, m),<br>6.70~7.37(9H, m), 7.94(1H, s)<br>[CDCl₃] glassy |
| B-66 | 1.55(6H, s), 2.00~2.30(2H, m),<br>3.31~3.75(4H, m), 3.71(3H, s),<br>6.45~6.65(1H, m),<br>6.80~7.35(8H, m), 8.00(1H, s) |
| B-67 | [CDCl₃] m.p. 155~157° C.<br>1.50(6H, s), 1.95~2.35(2H, m),<br>3.36~3.76(4H, m),<br>7.05~7.60(8H, m), 7.86(1H, s),<br>8.59(1H, s)<br>[CDCl₃ + DMSO - d₆] m.p. 136~138° C. |
| B-68 | 1.55(6H, s), 2.03~2.24(2H, m),<br>3.35~3.75(4H, m),<br>6.80~7.55(6H, m),<br>7.93~8.03(2H, m)<br>[CDCl₃] m.p. 160~161° C. |
| B-69 | 1.58(6H, s), 1.99~2.28(2H, m),<br>2.28(3H, s), 3.39~3.79(4H, m),<br>6.75~6.95(2H, m), 7.25(5H, m),<br>7.95~8.30(2H, m)<br>[CDCl₃] m.p. 135~136° C. |
| B-70 | 1.53(6H, s), 1.81~2.35(2H, m),<br>3.32~3.78(4H, m),<br>6.74~7.47(8H, m),<br>7.64(1H, s), 8.07(1H, bs)<br>[CDCl₃] glassy |
| B-71 | 1.50(6H, s), 1.90~2.25(2H, m),<br>3.29~3.66(4H, m), 3.78(3H, s),<br>6.95~7.30(6H, m),<br>7.55~8.04(3H, m), 8.25(1H, s)<br>[CDCl₃] glassy |
| B-72 | 1.42(6H, s), 2.05~2.35(2H, m),<br>3.38~3.58(4H, m),<br>7.26~7.33(4H, m)<br>[CDCl₃ + DMSO - d₆] m.p. 231~233° C. |
| B-73 | 1.42(6H, s), 2.05~2.35(2H, m),<br>3.39~3.58(4H, m),<br>7.25~7.80(4H, m)<br>[CDCl₃ + DMSO - d₆] m.p. 213~214° C. |
| B-74 | 1.51(6H, s), 2.05~2.26(2H, m),<br>3.35~3.59(4H, m),<br>6.42(1H, t of t, J=9.2Hz),<br>7.00~7.45(6H, m), 8.18(1H, s)<br>[CDCl₃] glassy |
| B-75 | 1.49(6H, s), 2.05~2.30(2H, m),<br>3.35~3.55(4H, m),<br>6.40(1H, t of t, J=9.2Hz),<br>6.99~7.70(6H, m), 8.02(1H, s)<br>[CDCl₃] glassy |
| B-76 | 1.60(6H, s), 2.01~2.39(2H, m),<br>3.39~3.80(3H, m),<br>7.11~7.67(9H, m), 8.17(1H, bs)<br>[CDCl₃] m.p. 132~134° C. |
| B-77 | 1.52(6H, s), 1.90~2.25(2H, m),<br>3.30~3.70(4H, m),<br>6.50~6.80(1H, m),<br>7.00~7.65(8H, m), 8.07(1H, s)<br>[CDCl₃] m.p. 175~177° C. |
| B-78 | 1.51(6H, s), 1.95~2.25(2H, m),<br>3.30~3.62(4H, m),<br>7.00~7.35(7H, m),<br>7.75~7.80(1H, m), 8.03(1H, s)<br>[CDCl₃] m.p. 162~165° C. |
| B-79 | 1.59(6H, s), 2.00~2.30(2H, m),<br>2.45(3H, s), 3.37~3.77(4H, m),<br>6.90~7.24(8H, m),<br>7.58~7.60(1H, m), 8.05(1H, brs)<br>[CDCl₃] m.p. 136~138° C. |
| B-80 | 1.57(6H, s), 2.05~2.35(2H, m),<br>2.66(3H, s), 3.39~3.80(4H, m),<br>7.16~7.80(8H, m), 8.27(1H, s)<br>[CDCl₃] m.p. 177~179° C. |
| B-81 | 1.57(6H, s), 2.05~2.35(2H, m),<br>3.00(3H, s), 3.39~3.79(4H, m),<br>7.15~7.50(7H, m),<br>7.89~8.00(2H, m), 8.23(1H, brs)<br>[CDCl₃] m.p. 85~87° C. |
| B-82 | 1.42(6H, s), 2.05~2.30(2H, m),<br>3.30~3.75(4H, m), 7.24(5H, s),<br>9.00(1H, brs), 11.70(1H, brs),<br>[CDCl₃ + DMSO - d₆] m.p. 175~180° C. |
| B-83 | 1.54(6H, s), 2.05~2.30(2H, m), |

TABLE 2-B-continued

| Compound No. | $^1$H-NMR δ (ppm) (Solvent) Physical property |
|---|---|
| | 2.50(3H, s), 3.35~3.78(4H, m), 7.20(5H, s), 9.70(1H, brs) [CDCl$_3$] m.p. 258~260° C. |
| B-84 | 1.57(6H, s), 2.03~2.46(2H, m), 3.39~3.83(3H, m), 7.24(5H, s), 7.63~7.89(3H, m), 8.26(1H, bs) [CDCl$_3$] m.p. 172~174° C. |
| B-85 | 1.50(6H, s), 1.89~2.35(2H, m), 3.37~3.67(3H, m), 6.91~7.84(7H, m), 8.29(1H, s) (CDCl$_3$) glassy |
| B-86 | 1.56(6H, s), 2.08~2.39(2H, m), 3.34~3.76(3H, m), 6.93~7.19(7H, m), 8.25(1H, bs), 8.55(1H, bs) [CDCl$_3$] m.p. 153~155° C. |
| B-87 | 1.55(6H, s), 197~2.44(2H, m), 3.22~3.83(4H, m), 5.42(1H, bs), 6.85~7.46(6H, m) [CDCl$_3$] m.p. 160~164° C. |
| B-88 | 1.56(6H, s), 1.98~2.50(2H, m), 3.28~3.80(4H, m), 7.25(5H, s), 7.39(1H, s), 9.29(1H, bs) [CDCl$_3$] m.p. 178~179° C. |
| B-89 | 1.45(6H, s), 2.00~2.30(2H, m), 3.25~3.70(4H, m), 5.73(2H, brs), 7.24(5H, s) [CDCl$_3$] m.p. 162~165° C. |
| B-90 | 1.15(3H, d, J=6Hz), 1.46(6H, s), 1.95~2.45(2H, m), 3.35~3.60(2H, m), 3.75~4.10(1H, m), 7.23(5H, s) [CDCl$_3$ + DMSO - d$_6$] m.p. 199~201° C. |
| B-91 | 1.15(3H, d, J=6Hz), 1.51(6H, s), 2.00~2.50(2H, m), 3.40~3.60(2H, m), 3.80~4.15(1H, m), 6.25~6.65(1H, m), 7.00~7.40(7H, m), 8.68(1H, s) [CDCl$_3$ + DMSO - d$_6$] m.p. 144~145° C. |
| B-92 | 1.05(3H, d, J=6Hz), 1.43(3H, s), 1.48(3H, s), 1.90~2.30(2H, m), 3.20~3.45(2H, m), 3.70~4.00(1H, m), 7.00~7.32(6H, m), 9.69(1H, s) [CDCl$_3$] glassy |
| B-93 | 1.55(6H, s), 1.99~2.38(2H, m), 3.30~3.83(3H, m), 6.94~7.60(8H, m), 8.09(1H, bs) [CDCl$_3$] m.p. 142~144° C. |
| B-94 | 1.48(6H, s), 1.89~2.32(2H, m), 3.28~3.72(3H, m), 6.90~7.61(8H, m), 8.13(1H, s) [CDCl$_3$] m.p. 191~193° C. |
| B-95 | 1.17(3H, t, J=7Hz), 1.55(6H, s), 2.26(3H, m), 2.20~2.75(4H, m), 3.28~3.86(4H, m), 7.25(5H, s), 8.83(1H, bs) [CDCl$_3$] m.p. 196~200° C. |
| B-96 | 1.50(6H, s), 3.55~3.80(4H, m), 6.85~7.55(5H, m) [CDCl$_3$ + DMSO - d$_6$] m.p. 215~216° C. |
| B-97 | 1.51(6H, s), 3.55~4.00(4H, m), 6.30~6.65(1H, m), 6.95~7.65(7H, m), 9.40(1H, brs) [CDCl$_3$ + DMSO - d$_6$] m.p. 181~182° C. |
| B-98 | 1.54(6H, s), 2.00~2.35(2H, m), 3.35~3.60(4H, m), 7.00~7.60(8H, m), 8.05(1H, brs) [CDCl$_3$] m.p. 153~155° C. |
| B-99 | 1.54(6H, s), 2.02~2.39(2H, m), 3.35~3.80(3H, m), 7.14~7.37(6H, m), 7.70(1H, s), 7.93(1H, s), 8.29(1H, bs) [CDCl$_3$] m.p. 166~168° C. |
| B-100 | 1.55(6H, s), 1.94~2.36(2H, m), 3.35~3.79(3H, m), 7.08~7.32(6H, m), 7.65(2H, s), 8.11(1H, s) [CDCl$_3$] m.p. 201~203° C. |
| B-101 | 1.57(6H, s), 2.08~2.45(2H, m), 3.36~3.80(3H, m), 6.46~8.23(8H, m), 8.43(1H, bs) [CDCl$_3$] m.p. 166~167° C. |
| B-102 | 1.45(6H, s), 1.95~2.25(2H, m), 3.35~3.75(4H, m), 7.20(5H, s), 12.80(1H, brs) [CDCl$_3$ + DMSO - d$_6$] m.p. 256~257° C. |
| B-103 | 1.41(6H, s), 2.00~2.30(2H, m), 3.38~3.57(4H, m), 6.90~7.35(3H, m) [CDCl$_3$ + DMSO - d$_6$] m.p. 255~257° C. |
| B-104 | 1.55(6H, s), 2.10~2.45(2H, m), 3.39~3.66(4H, m), 6.25~6.65(1H, s), 6.80~7.35(5H, m), 8.15(1H, brs) [CDCl$_3$] m.p. 151~152° C. |
| B-105 | 1.56(6H, s), 2.05~2.40(2H, m), 3.39~3.66(4H, m), 6.75~7.55(6H, m), 8.50(1H, brs), 8.08(1H, brs) [CDCl$_3$] m.p. 175~176° C. |
| B-106 | 1.47(6H, s), 2.13~2.32(2H, m), 3.43~3.62(4H, m), 6.80~7.13(3H, m), 7.25(1H, s), 11.73(1H, s) [CDCl$_3$ + DMSO - d$_6$] m.p. 212~214° C. |
| B-107 | 1.52(6H, s), 2.01~2.48(2H, m), 3.32~3.80(4H, m), 7.25(5H, s), 9.25(1H, bs) [CDCl$_3$] m.p. 201~203° C. |
| B-108 | 1.53(6H, s), 2.15~2.65(2H, m), 3.37~3.95(4H, m), 7.26(5H, s), 9.30(1H, bs) [CDCl$_3$] m.p. 164~166° C. |
| B-109 | 1.54(6H, s), 2.05~2.58(2H, m), 3.30~3.84(4H, m), 6.66(1H, s), 7.25(5H, s), 9.21(1H, bs) [CDCl$_3$] m.p. 219~222° C. |
| B-110 | 1.57(6H, s), 1.95~2.40(2H, m), 3.39~3.67(4H, m), 6.89~7.30(6H, m), 7.66~7.69(1H, m), 8.07(1H, bs) [CDCl$_3$] m.p. 163~164° C. |
| B-111 | 1.55(6H, s), 2.05~2.35(2H, m), 2.52(3H, m), 3.39~3.70(4H, m), 7.10~7.25(4H, m), 9.65(1H, bs) [CDCl$_3$] m.p. 244~247° C. |
| B-112 | 1.14(3H, d, J=6Hz), 1.54(6H, s), 1.90~2.40(2H, m), 3.37~3.57(2H, m), 3.75~4.15(1H, m), 6.95~7.45(8H, m), 7.65~7.70(1H, m), 8.08(1H, bs) [CDCl$_3$] m.p. 138~140° C. |
| B-113 | 1.16(3H, d, J=6Hz), 1.51(3H, s), 1.54(3H, s), 2.00~2.30(2H, m), 3.39~3.60(2H, m), 3.75~4.10(1H, m), 6.80~7.55(7H, m), 7.65~7.75(1H, m), 8.30(1H, m) [CDCl$_3$] m.p. 154~156° C. |
| B-114 | 1.11(3H, d, J=7Hz), 1.47(6H, s), 1.95~2.30(2H, m), 3.35~3.55(2H, m), 3.65~4.00(1H, m), 7.00~7.50(4H, m), 10.02(1H, bs) [CDCl$_3$] m.p. 205~207° C. |
| B-115 | 1.13(3H, d, J=6Hz), 1.52(6H, s), 2.00~2.35(2H, m), 3.37~3.57(2H, m), 3.75~4.00(1H, m), 6.42(1H, tt, J=9Hz, 2Hz) 7.00~7.15(6H, m), 8.09(1H, bs) |

TABLE 2-B-continued

| Compound No. | $^1$H-NMR δ (ppm) (Solvent) Physical property |
|---|---|
| B-116 | [CDCl$_3$] m.p. 149~150° C. 1.11(3H, d, J=7Hz), 1.52(6H, s), 1.90~2.25(2H, m), 3.35~3.56(2H, m), 3.65~3.95(1H, m), 6.95~7.25(7H, m), 7.63(1H, bs), 7.98(1H, bs) |
| B-117 | [CDCl$_3$] m.p. 136~137° C. 1.10(3H, d, J=7Hz), 1.50(6H, s), 1.95~2.40(2H, m), 3.33~3.52(2H, m), 3.65~3.95(1H, m), 7.03~7.27(5H, m), 9.35(1H, bs) |
| B-118 | [CDCl$_3$] glassy 1.52(6H, s), 2.06~2.56(2H, m), 3.37~3.70(4H, m), 7.03~7.46(4H, m), 9.20(1H, bs) |
| B-119 | [CDCl$_3$] m.p. 210~212° C. 1.52(6H, s), 2.00~2.55(2H, m), 3.26~3.77(4H, m), 6.96~7.33(4H, m), 9.20(1H, bs) |
| B-120 | [CDCl$_3$] m.p. 206~209° C. 1.56(6H, s), 2.05~2.47(2H, m), 3.30~3.72(4H, m), 6.95~7.45(5H, m), 9.27(1H, bs) |
| B-121 | [CDCl$_3$] m.p. 173~174° C. 1.56(6H, s), 2.06~2.39(2H, m), 3.27~3.69(4H, m), 3.74(3H, s), 6.59(1H, t, J=2Hz), 7.05(1H, t, J=2Hz), 7.24(5H, s), 8.05(1H, bs) |
| B-122 | [CDCl$_3$] glassy 1.56(6H, s), 1.92~2.35(2H, m), 3.27~3.80(4H, m), 6.61~6.86(1H, m), 7.00~7.48(7H, m), 8.16(1H, bs) |
| B-123 | [CDCl$_3$] m.p. 162~165° C. 1.57(6H, s), 2.03~2.42(2H, m), 3.35~3.85(4H, m), 7.07~8.02(8H, m), 8.39(1H, bs) |
| B-124 | [CDCl$_3$] m.p. 220~221° C. 1.59(6H, s), 2.18(3H, s), 1.96~2.42(2H, m), 3.27~3.84(4H, m), 6.89~7.36(7H, m), 7.93(1H, bs), 8.04(1H, bs) |
| B-125 | [CDCl$_3$] m.p. 178~180° C. 1.56(6H, s), 2.10~2.32(2H, m), 3.39~3.80(4H, m), 7.05~7.30(7H, m), 8.16(1H, bs), 8.70~8.84(1H, m) |
| B-126 | [CDCl$_3$] m.p. 172~174° C. 1.59(6H, s), 2.10~2.45(2H, m), 3.45~3.70(4H, m), 7.07~7.26(6H, m), 8.15(1H, bs), 8.70~8.85(1H, m) [CDCl$_3$] m.p. 194~196° C. |

TABLE 2-C

| Compound No. | $^1$H—NMR δ (ppm) (Solvent) | Physical property |
|---|---|---|
| C-1 | 1.08(3H, t, J=7Hz), 1.68(6H, s), 2.50~2.80(2H, m), 4.00~4.10(2H, m), 4.70~4.78(1H, m), 7.00~7.50(6H, m), 8.44(1H, d, J=2Hz), 8.60(1H, brs) [CDCl$_3$] | viscous liquid |
| C-2 | 1.04(3H, t, J=7Hz), | visoous liquid |

TABLE 2-C-continued

| Compound No. | $^1$H—NMR δ (ppm) (Solvent) | Physical property |
|---|---|---|
| | 1.19(3H, t, J=7Hz), 1.52(3H, s), 1.56(3H, s), 2.50~2.75(2H, m), 4.00~4.33(4H, m), 4.65(1H, d, J=3Hz), 7.25~7.50(5H, m), [CDCl$_3$] | |
| C-3 | 1.03(3H, t, J=7Hz), 1.52(3H, s), 1.55(3H, s), 2.50~2.75(2H, m), 3.91~4.09(2H,m), 4.61~4.68(1H, m), 7.32(5H, s) [CDCl$_3$] | m.p. 154~155° C. |
| C-4 | 1.04(3H, t, J=7Hz), 1.70(6H, s), 2.49~2.74(2H, m), 3.99~4.05(2H, m), 4.60~4.75(1H, m), 7.05~7.55(10H, m), 8.85(1H, brs) [CDCl$_3$] | viscous liquid |
| C-5 | 1.06(3H, t, J=7H), 1.67(6H, s), 2.51~2.77(2H, m), 3.72(3H, s), 3.98~4.10(2H, m), 4.65~4.71(1H, m), 6.80~7.50(8H, m), 8.27~8.40(1H, m), 8.59(1H, brs) [CDCl$_3$] | viscous liquid |
| C-6 | 1.07(3H, t, J=7H), 1.66(6H, s), 2.53~2.70(2H, m), 3.71(3H, s), 4.00~4.06(2H, m), 4.67~4.74(1H, m), 6.69(1H, d, J=9Hz), 6.96(1H, dd, J=2Hz, 9Hz), 7.24~7.51(5H, m), 8.46(1H, d, J=2Hz), 8.63(1H, brs) [CDCl$_3$] | glassy material |
| C-7 | 1.04(3H, t, J=7Hz), 1.58(6H, s), 1.0~2.0(10H, m), 2.51~2.75(2H, m), 3.5~3.9(1H, m), 3.97~4.04(2H, m), 4.55~4.70(1H, m), 6.2~6.45(1H, m), 7.20~7.55(5H, m) [CDCl$_3$] | viscous liquid |
| C-8 | 0.96(3H, t, J=7Hz), 1.54(6H, s), 2.36~2.64(2H, m), 3.84~3.89(2H, m), 4.45~4.60(1H, m), 6.95(1H, d, J=4Hz), 7.30~7.37(5H, m), 7.55(1H, d, J=4Hz) [CDCl$_3$] | m.p. 79~83° C. |
| C-9 | 1.04(3H, t, J=7Hz), 1.66(6H, s), 2.52~2.75(2H, m), 3.95~4.05(2H, m), 4.60~4.75(1H, m), 7.05(1H, t, J=2Hz), 7.20~7.55(7H, m), 9.12(1H, brs) [CDCl$_3$] | m.p. 135~138° C. |
| C-10 | 1.02(3H, t, J=7Hz), 1.67(6H, s), 2.48~2.73(2H, m), 3.72(3H, s), 4.00~4.10(2H, m), 4.60~4.75(1H, m), 6.78(2H, d, J=9Hz), 7.20~7.48(7H, m), 8.65(1H, brs) [CDCl$_3$] | glassy material |
| C-11 | 1.02(3H, t, J=7Hz), 1.67(6H, s), 2.46~2.72(2H, m), 3.70(6H, s), 3.90~4.02(2H, m), 4.55~4.70(1H, m), 6.19(1H, t, J=2Hz), 6.70(2H, d, J=2Hz), 7.34(5H, s), 8.83(1H, brs) [CDCl$_3$] | m.p. 150~151° C. |
| C-12 | 1.03(3H, t, J=7Hz), 1.64(6H, s), 2.49~2.73(2H, m), 3.95~4.10(2H, m), 4.60~4.71(1H, m), 6.55~7.47(7H, m), 7.95~8.35(1H, m), | viscous liquid |

TABLE 2-C-continued

| Compound No. | ¹H—NMR δ (ppm) (Solvent) | Physical property |
|---|---|---|
| | 8.52~8.59(1H, m)<br>[CDCl₃] | |
| C-13 | 1.07(6H, t, J=7H), 1.74(6H, s),<br>2.30~2.80(4H, m),<br>4.03~4.07(2H, m),<br>4.65~4.80(1H, m),<br>7.13~7.95(9H, m),<br>8.43~8.46(1H, m)<br>[CDCl₃] | m.p. 129~131° C. |
| C-14 | 1.03(3H, t, J=7Hz), 1.53(3H, s),<br>1.56(3H, s), 2.44~2.74(3H, m),<br>3.99~4.05(2H, m),<br>4.60~4.69(3H, m), 7.35(5H, s)<br>[CDCl₃] | viscous liquid |
| C-15 | 1.01(3H, t, J=7Hz), 1.65(6H, s),<br>2.47~2.70(2H, m),<br>3.91~4.13(2H, m),<br>4.55~4.68(1H, m),<br>6.92~7.50(9H, m), 8.75(1H, s)<br>[CDCl₃] | glassy material |
| C-16 | 1.04(3H, t, J=7Hz), 1.65(6H, s),<br>2.49~2.74(2H, m),<br>3.99~4.10(2H, m),<br>4.65~4.74(1H, m),<br>6.90~7.55(8H, m),<br>8.27~8.55(2H, m)<br>[CDCl₃] | viscous liquid |
| C-17 | 1.02(3H, t, J=7Hz), 1.63(6H, s),<br>2.47~2.72(2H, m),<br>3.94~4.01(2H, m),<br>4.60~4.75(1H, m),<br>7.10~7.60(9H, m), 8.88(1H, s)<br>[CDCl₃] | glassy material |
| C-18 | 1.09(3H, t, J=7Hz), 1.68(6H, s),<br>2.55~2.80(2H, m),<br>4.01~4.10(2H, m),<br>4.70~4.75(1H, m),<br>7.34~7.38(7H, m),<br>8.55(1H, s)<br>[CDCl₃] | glassy material |
| C-19 | 1.04(3H, t, J=7Hz), 1.68(6H, s),<br>2.52~2.75(2H, m),<br>4.06~4.15(2H, m),<br>4.65~4.75(1H, m),<br>7.10~7.90(8H, m),<br>8.32~8.36(1H, m), 9.15(1H, s)<br>[CDCl₃] | glassy material |
| C-20 | 1.07(3H, t, J=7Hz), 1.68(6H, s),<br>2.54~2.79(2H, m),<br>4.01~4.14(2H, m),<br>4.65~4.80(1H, m),<br>7.09~7.55(7H, m),<br>8.17~8.34(1H, m), 8.60(1H, s)<br>[CDCl₃] | m.p. 147~149° C. |
| C-21 | 1.05(3H, t, J=7Hz), 1.65(6H, s),<br>2.51~2.76(2H, m),<br>3.98~4.05(2H, m),<br>4.65~4.73(1H, m),<br>7.05~7.58(7H, m),<br>8.25(1H, d, J=9Hz), 8.48(1H, brs)<br>[CDCl₃] | viscous liquid |
| C-22 | 1.03(3H, t, J=7Hz), 1.63(6H, s),<br>2.50~2.74(2H, m),<br>4.03~4.15(2H, m),<br>4.64~4.72(1H, m),<br>7.08~7.70(8H, m), 8.98(1H, s)<br>[CDCl₃] | viscous liquid |
| C-23 | 1.05(3H, t, J=7Hz), 1.68(6H, s),<br>2.53~2.78(2H, m),<br>3.85~4.25(2H, m),<br>4.65~4.80(1H, m),<br>7.20~8.10(8H, m), 9.40(1H, s)<br>[CDCl₃] | glassy material |
| C-24 | 0.98(3H, t, J=7Hz), 1.71(6H, s),<br>2.42~2.68(2H, m),<br>3.95~3.99(2H, m),<br>4.60~4.75(1H, m), | |
| | 7.20~7.95(12H, m), 8.99(1H, s)<br>[CDCl₃] | glassy material |
| C-25 | 1.01(3H, t, J=7Hz), 1.54(6H, s),<br>2.45~2.70(2H, m),<br>4.00~4.14(1H, m),<br>4.56~4.75(2H, m),<br>7.15~7.60(4H, m),<br>[CDCl₃ + DMSO-d₆] | m.p. 160~162° C. |
| C-26 | 1.00(3H, t, J=7Hz), 1.67(6H, s),<br>4.00~4.10(1H, m),<br>4.62~4.72(2H, m),<br>7.02(1H, t, J=2Hz),<br>7.21~7.44(6H, m), 9.13(1H, s)<br>[CDCl₃] | m.p. 152~153° C. |
| C-27 | 1.55(3H, s), 1.58(3H, s),<br>2.37(3H, s), 4.05~4.14(1H, m),<br>4.43~4.47(1H, m),<br>4.57~4.65(1H, m),<br>7.20~7.50(4H, m),<br>[CDCl₃ + DMSO-d₆] | m.p. 174~175° C. |
| C-28 | 1.71(6H, s), 2.39(3H, s),<br>3.95~4.15(1H, m),<br>4.46~4.50(1H, m),<br>4.62~4.70(1H, m),<br>7.01(1H, d, J=2Hz),<br>7.16~7.40(5H, m),<br>8.42(1H, d, J=2Hz), 8.60(1H, s)<br>[CDCl₃] | m.p. 128~129° C. |
| C-29 | 1.70(6H, s), 2.36(3H, s),<br>4.00~4.10(1H, m),<br>4.45~4.51(1H, m),<br>4.59~4.68(1H, m),<br>7.04(1H, t, J=2Hz),<br>7.31~7.46(6H, m), 9.16(1H, s)<br>[CDCl₃] | m.p. 74~77° C. |
| C-30 | 1.00(3H, t, J=7Hz), 1.64(3H, s),<br>1.70(3H, s), 2.66(3H, s),<br>3.96~3.99(1H, m),<br>4.12~4.20(1H, m),<br>4.71~4.85(1H, m), 7.23(5H, s)<br>[CDCl₃] | m.p. 190~192° C. |
| C-31 | 1.07(3H, t, J=7Hz), 1.73(6H, s),<br>2.52~2.66(2H, m), 3.91(6H, s),<br>4.02~4.15(2H, m),<br>4.68~4.75(1H, m), 7.36(5H, s),<br>8.32~8.50(3H, m), 9.11(1H, s)<br>[CDCl₃] | m.p. 75~78° C. |
| C-32 | 1.05(3H, t, J=7H), 1.69(6H, s),<br>2.53~2.76(2H, m),<br>4.07(1H, dd, J=4Hz, 2Hz),<br>4.38(1H, brs),<br>4.71(1H, dd, J=1Hz, 4Hz),<br>6.85~7.60(6H, m),<br>8.44(1H, d, J=2Hz), 8.58(1H, s)<br>[CDCl₃] | glassy material |
| C-33 | 1.00(3H, t, J=7Hz), 1.64(6H, s),<br>2.51~2.71(2H, m),<br>3.95~4.09(1H, m), 4.29(1H, brs),<br>4.62~4.70(1H, m),<br>7.03(1H, t, J=2Hz),<br>7.10~7.50(6H, m), 8.83(1H, s)<br>[CDCl₃] | glassy material |
| C-34 | 1.67(6H, s), 2.37(3H, s),<br>3.87~4.07(2H, m),<br>4.58~4.66(1H, m),<br>7.03(1H, t, J=2Hz), 7.36(5H, s),<br>7.42(2H, d, J=2Hz), 9.11(1H, brs)<br>[CDCl₃] | glassy |
| C-35 | 1.68(6H, s), 2.42(3H, s),<br>3.84~4.08(2H, m),<br>4.62~4.70(1H, m),<br>6.85~7.55(7H, m),<br>8.45(1H, d, J=2Hz), 8.55(1H, brs)<br>[CDCl₃] | glassy |
| C-36 | 1.62(6H, s), 2.32(3H, s),<br>3.93~4.11(2H, m),<br>4.55~4.62(1H, m), | glassy |

TABLE 2-C-continued

| Compound No. | $^1$H—NMR δ (ppm) (Solvent) | Physical property |
|---|---|---|
| | 7.02(1H, t, J=2Hz), 7.05~7.40(4H, m), 7.47(1H, d, J=2Hz), 8.77(1H, s) [CDCl$_3$] | |
| C-37 | 1.70(6H, s), 2.39(3H, s), 4.00~4.25(2H, m), 4.63~4.70(1H, m), 6.90~7.45(6H, m), 8.47(1H, d, J=2Hz), 8.61(1H, brs) [CDCl$_3$] | glassy |
| C-38 | 1.04(3H, t, J=7Hz), 1.57(6H, s), 2.30~2.80(2H, m), 3.90~4.00(2H, m), 4.57~4.61(1H, m), 7.31(5H, s), 10.60(1H, brs) [CDCl$_3$] | glassy |
| C-39 | 1.58(6H, s), 2.31(3H, s), 3.92~4.11(2H, m), 4.49~4.56(1H, m), 7.02~7.32(5H, m), 10.50(1H, brs) [CDCl$_3$] | glassy |
| C-40 | 1.03(3H, t, J=7Hz), 1.60(6H, s), 2.28(3H, s), 2.45~2.75(2H, m), 4.00~4.10(2H, m), 4.64~4.69(1H, m), 6.42(1H, s), 7.36(5H, s), 10.76(1H, s) [CDCl$_3$] | glassy |
| C-41 | 1.00(3H, t, J=7Hz), 1.55(6H, s), 2.21(3H, s), 2.40~2.75(2H, m), 3.95~4.05(2H, m), 4.63~4.68(1H, m), 6.21(1H, s), 7.36(5H, s), 10.02(1H, s) [CDCl$_3$] | glassy |
| C-42 | 1.66(6H, s), 2.36(3H, s), 3.95~4.10(2H, m), 4.58~4.65(1H, m), 7.10~7.65(4H, m), 7.64(2H, s), 8.88(1H, brs) [CDCl$_3$] | glassy |
| C-43 | 1.55(3H, s), 1.59(3H, s), 2.36(3H, s), 4.05~4.25(2H, m), 4.59~4.66(1H, m), 6.30~6.75(1H, m), 6.95~7.50(6H, m), 9.49(1H, brs) [CDCl$_3$ + DMSO-d$_6$] | m.p. 102~105° C. |
| C-44 | 1.61(3H, s), 1.64(3H, s), 2.38(3H, s), 4.05~4.25(2H, m), 4.62~4.68(1H, m), 7.05~7.65(8H, m), 7.90~7.95(1H, m), 8.18(1H, brs) [CDCl$_3$ + DMSO-d$_6$] | m.p. 162~165° C. |
| C-45 | | |
| C-46 | | |
| C-47 | | |
| C-48 | | |
| C-49 | | |
| C-50 | | |
| C-51 | | |

TABLE 2-D

| Compound No. | $^1$H—NMR δ (ppm) (Solvent) Physical property |
|---|---|
| D-1 | 1.60(6H, s), 4.54(2H, d, J=2Hz), 4.77(1H, s), 6.81~7.50(8H, m), 7.86(1H, bs) [CDCl$_3$] viscous oil |
| D-2 | 1.11(3H, t, J=7Hz), 1.54(6H, s), 4.04(2H, q, J=7Hz), 4.53(2H, d, J=2Hz), 4.76(1H, bs), 7.06~7.44(5H, m) [CDCl$_3$] viscous oil |
| D-3 | 1.59(6H, s), 4.61(2H, s), 4.95(1H, s), 7.39(5H, s), |

TABLE 2-D-continued

| Compound No. | $^1$H—NMR δ (ppm) (Solvent) Physical property |
|---|---|
| | 9.85(1H, bs) [CDCl$_3$] m.p. 144~147° C. |
| D-4 | 1.61(6H, s), 4.55(2H, d, J=2Hz), 4.80(1H, s), 6.19~7.50(8H, m), 7.98(1H, bs) [CDCl$_3$] glassy |
| D-5 | 1.60(6H, s), 4.56(2H, s), 4.83(1H, s), 6.48~7.15(2H, m), 7.33(5H, s), 7.90~8.31(2H, m) [CDCl$_3$] viscous oil |
| D-6 | 1.65(6H, s), 5.02(2H, d, J=5Hz), 5.25(1H, s), 6.60~8.99(3H, m), 7.41(5H, s), 9.19(1H, s) [d$_6$ – DMSO] m.p. 187~188° C. |
| D-7 | 1.39~1.86(6H, m), 4.59(2H, d, J=3Hz), 4.78(1H, s), 6.52~7.11(2H, m), 7.28(5H, s), 7.79~8.23(1H, m), 8.38(1H, bs) [CDCl$_3$] glassy |
| D-8 | 1.57(6H, s), 4.56(2H, s), 4.81(1H, s), 6.82~7.56(9H, m), 7.99(1H, bs) [CDCl$_3$] glassy |
| D-9 | 1.62(6H, s), 3.76(3H, s), 4.61(2H, s), 4.85(1H, s), 6.74~7.55(8H, m), 8.08(1H, bs) [CDCl$_3$] glassy |
| D-10 | |
| D-11 | |

In Tables 1-A to 1-D, abbreviations used have the following meanings; Me: methyl group, Et: ethyl group, i-Pr: iso-propyl group, c-Pr: cyclopropyl group, t-Bu: tert-butyl group, c-Hex: cyclohexyl group, Prop: propargyl group, and Ph: phenyl group. Q-4, Q-5, Q-8, Q-9, Q-10, Q-16, Q-23, Q-24, Q-27, Q-32, Q-34, Q-39, Q-40, Q-44, Q-45, Q-47, Q-53 and Q-57 represent the groups illustrated below;

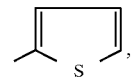 Q-4

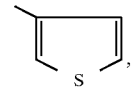 Q-5

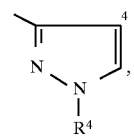 Q-8

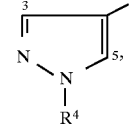 Q-9

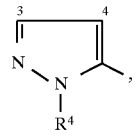 Q-10

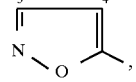 Q-16

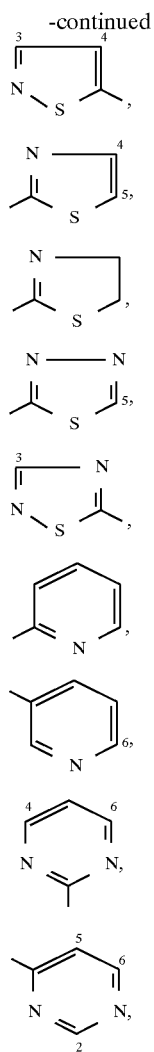
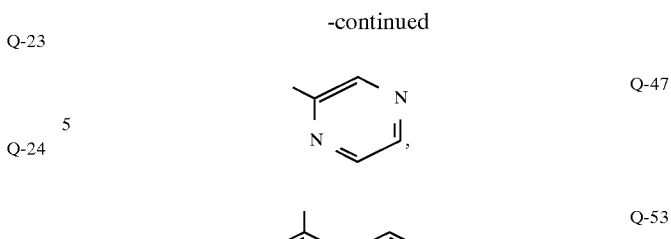

Tables 3-A-1, 3-A-2, 3-B, 3-C, 3-D and 3-E show the exemplary compounds of the present invention which can be prepared according to the procedures illustrated in the above Schemes and Examples 1 to 14, including Compounds A-1 to A-119, B-1 to B-126, C-1 to C-44 and D-1 to D-9 described above, although the present invention is not limited to these exemplary compounds.

Abbreviations used in the tables have the following meanings; Me: methyl group, Et: ethyl group, Pr: n-propyl group, i-Pr: iso-propyl group, c-Pr: cyclopropyl group, Bu: n-butyl group, t-Bu: tert-butyl group, Pen: n-pentyl group, Hex: n-hexyl group, c-Hex: cyclohexyl group, All: allyl group, and Prop: propargyl group.

TABLE 3-A-1

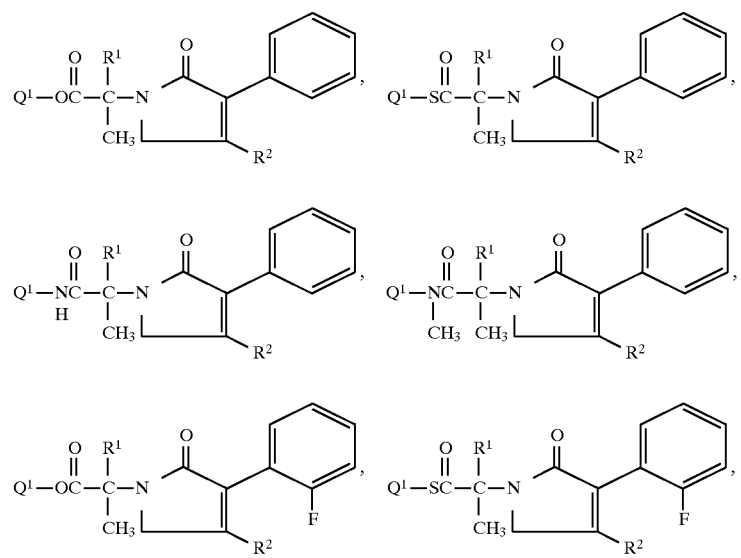

TABLE 3-A-1-continued

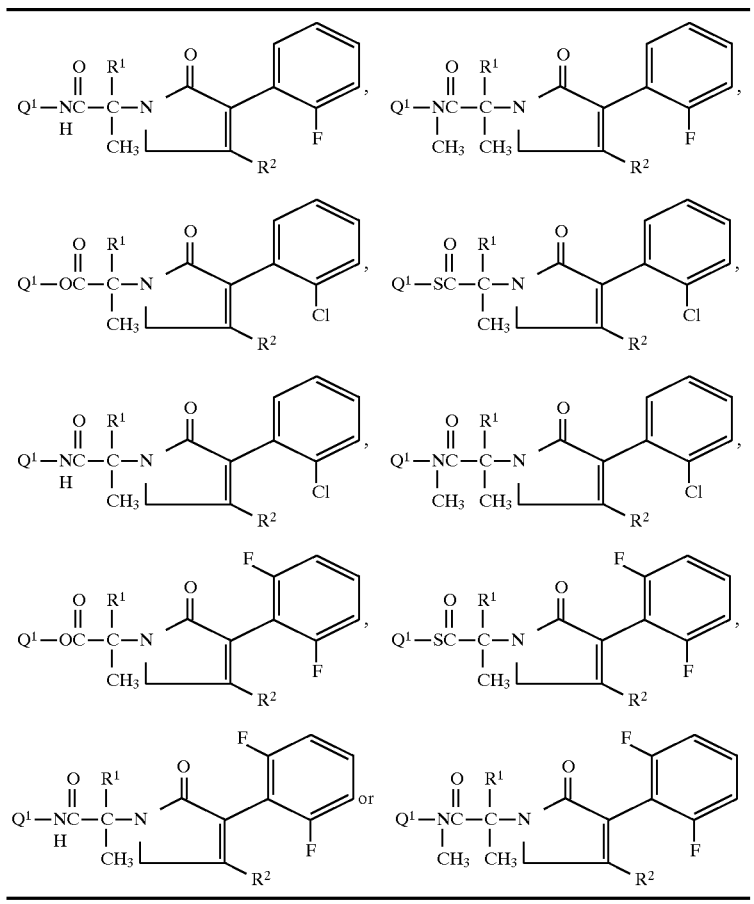

| R¹ | R² | Q¹ |
|---|---|---|
| Me | Me | Q-8 (R⁴:H) |
| Me | Me | Q-8 (R⁴:Me) |
| Me | Me | 4-Cl—Q-8 (R⁴:Me) |
| Me | Me | 4-NO₂—Q-8 (R⁴:H) |
| Me | Me | 4-NO₂—Q-8 (R⁴:Me) |
| Me | Me | Q-9 (R⁴:H) |
| Me | Me | Q-9 (R⁴:Me) |
| Me | Me | 3-Me—Q-9 (R⁴:H) |
| Me | Me | 3-Me—Q-9 (R⁴:Me) |
| Me | Me | 3,5-Cl₂—Q-9 (R⁴:Me) |
| Me | Me | 3,5-Me₂—Q-9 (R⁴:Me) |
| Me | Me | 3-CF₃—5-Cl—Q-9 (R⁴:H) |
| Me | Me | 3-CF₃—5-Cl—Q-9 (R⁴:Me) |
| Me | Me | Q-10 (R⁴:H) |
| Me | Me | Q-10 (R⁴:Me) |
| Me | Me | 3-Me—Q-10 (R⁴:H) |
| Me | Me | 3-Me—Q-10 (R⁴:Me) |
| Me | Me | 4-NO₂—Q-10 (R⁴:H) |
| Me | Me | 4-NO₂—Q-10 (R⁴:Me) |
| Me | Me | 3-Me—4-NO₂—Q-10 (R⁴:H) |
| Me | Me | 3-Me—4-NO₂—Q-10 (R⁴:Me) |
| Me | Me | 3-Me—4-Cl—Q-10 (R⁴:Me) |
| Me | Me | 3-CF₃—4-NO₂—Q-10 (R⁴:H) |
| Me | Me | 3-CF₃—4-NO₂—Q-10 (R⁴:Me) |
| Me | Me | 3-CF₃—4-Cl—Q-10 (R⁴:Me) |
| Me | Me | Q-11 (R⁴:H) |
| Me | Me | Q-11 (R⁴:Me) |
| Me | Me | 2-Me—Q-12 (R⁴:H) |
| Me | Me | 5-Me—Q-12 (R⁴:H) |
| Me | Me | Q-13 (R⁴:Me) |
| Me | Me | Q-14 |
| Me | Me | Q-15 |
| Me | Me | Q-16 |
| Me | Me | 3-Me—Q-16 |

TABLE 3-A-1-continued

| | | |
|---|---|---|
| Me | Et | 3-Me—Q-16 |
| Me | Me | 3,4-Me$_2$—Q-16 |
| Me | Me | Q-17 |
| Me | Me | Q-18 |
| Me | Me | Q-19 |
| Me | Me | Q-20 |
| Me | Et | Q-20 |
| Et | Me | Q-20 |
| Me | Me | Q-21 |
| Me | Me | 3,5-Me$_2$—Q-22 |
| Me | Me | 3-Me—Q-23 |
| Me | Et | 3-Me—Q-23 |
| Me | Me | Q-24 |
| Me | Et | Q-24 |
| Me | Me | 4-Me—Q-24 |
| Me | Me | 4-Cl—Q-24 |
| Me | Me | 5-Me—Q-24 |
| Me | Me | 5-Cl—Q-24 |
| Me | Me | 5-Br—Q-24 |
| Me | Me | 4-Me—5-Cl—-Q-24 |
| Me | Me | 4,5-Me$_2$—Q-24 |
| Me | Me | 2-Me—Q-25 |
| Me | Me | 2-Cl—Q-26 |
| Me | Me | Q-27 |
| Me | Et | Q-27 |
| Et | Me | Q-27 |
| Me | Me | 4-Me—Q-27 |
| Me | Me | 5-Me—Q-27 |
| Me | Me | 5-Cl—Q-28 |
| Me | Me | 5-Me—Q-28 |
| Me | Me | 5-Me—Q-29 |
| Me | Me | 5-Me—Q-30 |
| Me | Me | 4-Me—Q-31 |
| Me | Me | Q-32 |
| Me | Me | 5-Cl—Q-32 |
| Me | Me | 5-Me—Q-32 |
| Me | Me | 5-MeS—Q-32 |
| Me | Me | 5-MeSO—Q-32 |
| Me | Me | 5-MeSO$_2$—Q-32 |
| Me | Me | 5-EtS—Q-32 |
| Me | Me | 5-EtSO—Q-32 |
| Me | Me | 5-EtSO$_2$—Q-32 |
| Me | Me | 5-CF$_3$—Q-32 |
| Me | Me | 5-Me—Q-33 |
| Me | Me | Q-34 |
| Me | Me | 4-Me—Q-35 |
| Me | Me | Q-36 (R$^4$:H) |
| Me | Me | 3-Me—Q-37 (R$^4$:H) |
| Me | Me | Q-38 (R$^4$:Me) |
| Me | Me | Q-39 |
| Me | Et | Q-39 |
| Me | Me | 3,5-Cl$_2$—Q-39 |
| Me | Me | 3-NO$_2$—Q-39 |
| Me | Me | 3-Me—Q-39 |
| Me | Me | 4-Me—Q-39 |
| Me | Me | 4,6-Me$_2$—Q-39 |
| Me | Me | 5-Cl—Q-39 |
| Me | Me | 5-NO$_2$—Q-39 |
| Me | Me | 5-Me—Q-39 |
| Me | Me | 6-Me—Q-39 |
| Me | Me | 3-Cl—5-CF$_3$—Q-39 |
| Me | Me | 5-CF$_3$—Q-39 |
| Me | Me | 3-NO$_2$—6-Cl—Q-39 |
| Me | Me | 3-NO$_2$—6-Me—Q-39 |
| Me | Me | 4-CF$_3$—Q-39 |
| Me | Me | 3-CO$_2$Me—Q-39 |
| Me | Me | 3-CN—Q-39 |
| Me | Me | 4-CF$_3$—6-Cl—Q-39 |
| Me | Me | 2-OMe—Q-39 |
| Me | Me | 4-OMe—Q-39 |
| Me | Me | 4,6-Cl$_2$—Q-39 |
| Me | Me | 6-Cl—Q-39 |
| Me | Me | 4-Cl—Q-39 |
| Me | Me | 4-NO$_2$—Q-39 |
| Me | Me | Q-40 |
| Me | Et | Q-40 |
| Me | Me | 2-Cl—Q-40 |
| Me | Me | 6-Cl—Q-40 |
| Me | Me | 6-OMe—Q-40 |

TABLE 3-A-1-continued

| | | |
|---|---|---|
| Me | Me | 2,6-Cl$_2$—Q-40 |
| Me | Me | 2-NO$_2$—Q-40 |
| Me | Me | 2-CO$_2$Me—Q-40 |
| Me | Me | 4-Me—Q-40 |
| Me | Me | 5-CF$_3$—Q-40 |
| Me | Me | 5-Cl—Q-40 |
| Me | Me | 5-Me—Q-40 |
| Me | Me | 2,5-Cl—Q-40 |
| Me | Me | 4-Cl—Q-40 |
| Me | Me | 4-OMe—Q-40 |
| Me | Me | Q-41 |
| Et | Me | Q-41 |
| Me | Me | 2-Cl—Q-41 |
| Me | Me | 2,6-Cl$_2$—Q-41 |
| Me | Me | 2,3-Cl$_2$—Q-41 |
| Me | Me | 2,6-(CF$_3$)$_2$—Q-41 |
| Me | Me | 2,6-Me$_2$—Q-41 |
| Me | Et | 2-Me—Q-41 |
| Me | Me | 2-OMe—Q-41 |
| Me | Me | 3-NO$_2$—Q-41 |
| Me | Me | Q-42 |
| Me | Me | 6-Cl—Q-42 |
| Me | Me | 6-OMe—Q-42 |
| Me | Me | Q-43 |
| Me | Me | 6-CO$_2$Et—Q-43 |
| Me | Me | Q-44 |
| Me | Me | 4,6-Cl$_2$—Q-44 |
| Me | Me | 4-Cl—6-Me—Q-44 |
| Me | Me | 4,6-(OMe)$_2$—Q-44 |
| Me | Me | 4-Cl—6-OMe—Q-44 |
| Me | Me | 4-Me—6-OMe—Q-44 |
| Me | Me | 4-Me—Q-44 |
| Me | Me | 4,6-Me$_2$—Q-44 |
| Me | Me | 5-NO$_2$—Q-44 |
| Me | Me | 5-Cl—Q-44 |
| Me | Me | 4-OMe—Q-44 |
| Me | Me | 4,6-Cl$_2$—5-Me—Q-44 |
| Me | Me | 4-Cl—Q-44 |
| Me | Me | 4-OMe—6-CF$_3$—Q-44 |
| Me | Me | 4,6-(SMe)$_2$—Q-44 |
| Me | Me | Q-45 |
| Me | Me | 2-Cl—Q-45 |
| Me | Me | 2-OMe—Q-45 |
| Me | Me | 2-SMe—Q-45 |
| Me | Me | 5-CN—Q-45 |
| Me | Me | 2-Cl—5-CN—Q-45 |
| Me | Me | 6-Cl—Q-45 |
| Me | Me | 6-OMe—Q-45 |
| Me | Me | 5-CO$_2$Me—Q-45 |
| Me | Me | 2,6-Cl$_2$—Q-45 |
| Me | Me | 2,6-Me$_2$—Q-45 |
| Me | Me | 2,6-(OMe)$_2$—Q-45 |
| Me | Me | 2-Cl—5-F—Q-45 |
| Me | Me | 2,5-Cl$_2$—Q-45 |
| Me | Me | 2-Me—6-OMe—Q-45 |
| Me | Me | Q-46 |
| Me | Me | 4,6-Cl$_2$—Q-46 |
| Me | Me | 2,4-Cl$_2$—Q-46 |
| Me | Me | 4-Cl—Q-46 |
| Me | Me | 2-Cl—Q-46 |
| Me | Me | Q-47 |
| Me | Me | 3-CO$_2$Me—Q-47 |
| Me | Me | 3,5-Me$_2$—Q-47 |
| Me | Me | Q-48 |
| Me | Me | 4-Cl—Q-48 |
| Me | Me | 4-Me—Q-48 |
| Me | Me | 4,6-Cl$_2$—Q-48 |
| Me | Me | 4,6-(OMe)$_2$—Q-48 |
| Me | Me | 4,6-Me$_2$—Q-48 |
| Me | Me | 4-Me—6-OMe—Q-48 |
| Me | Me | Q-49 |
| Me | Me | 5,6-Me$_2$—Q-49 |
| Me | Me | Q-50 |
| Me | Et | Q-50 |
| Me | Me | 4-SCH$_3$—6-CH$_3$—Q-51 |
| Me | Me | Q-52 |
| Me | Me | 1-NO$_2$—Q-52 |
| Me | Me | 3-NO$_2$—Q-52 |
| Me | Me | 4-OMe—Q-52 |

TABLE 3-A-1-continued

| | | |
|---|---|---|
| Me | Me | 1-Br—Q-52 |
| Me | Me | 1-Cl—Q-52 |
| Me | Me | Q-53 |
| Me | Me | 2-NO$_2$—Q-53 |
| Me | Me | 2-Me—Q-53 |
| Me | Me | 8-NO$_2$—Q-53 |
| Me | Me | 4-Cl—Q-53 |
| Me | Me | Q-54 (R$^4$:H) |
| Me | Me | Q-55 (R$^4$:H) |
| Me | Me | Q-56 |
| Me | Me | 5-Cl—Q-56 |
| Me | Me | 6-Cl—Q-56 |
| Me | Me | Q-57 |
| Me | Me | 5-Cl—Q-57 |
| Me | Me | 6-Cl—Q-57 |
| Me | Me | Q-58 (R$^4$:H) |
| Me | Me | Q-59 |
| Me | Me | 4-OMe—Q-59 |
| Me | Me | 4-Cl—Q-59 |
| Me | Me | 4-Me—Q-59 |
| Me | Me | Q-60 |
| Me | Me | Q-61 |
| Me | Me | 2-Me—Q-61 |
| Me | Me | 2-Cl—Q-61 |
| Me | Me | Q-62 |
| Me | Me | Q-63 |
| Me | Me | Q-64 |
| Me | Me | Q-65 |
| Me | Me | 3-Me—Q-65 |
| Me | Me | 6-Cl—Q-65 |
| Me | Me | 3-Cl—Q-65 |
| Me | Me | Q-66 |
| Me | Me | 8-Cl—Q-66 |
| Me | Me | Q-67 |
| Me | Me | 5-t-Bu—Q-32 |
| Me | Me | 5-c-Pr—Q-32 |
| Me | Me | 6-OMe—Q-57 |
| Me | Me | 4-Cl—Q-57 |
| Me | Me | 6-F—Q-57 |
| Me | Me | 5-NO$_2$—Q-24 |
| Me | Me | 4-t-Bu—Q-24 |
| Me | Me | 5-Br—Q-32 |
| Me | Me | 4-Me—5-Br—Q-24 |
| Me | Et | 5-Cl—Q-24 |
| Me | Me | 4-F—Q-39 |
| Me | Me | 6-F—Q-39 |
| Me | Me | 3,6-F$_2$—Q-39 |
| Me | Me | 3,6-Cl$_2$—Q-39 |
| Me | Me | 4,6-F$_2$—Q-39 |
| Me | Me | 2-F—5-Cl—Q-40 |
| Me | Me | 2,6-F$_2$—Q-41 |
| Me | Me | 2,5-F$_2$—Q-41 |
| Me | Me | 2,6-F$_2$—Q-45 |
| Me | Me | 6-Cl—Q-47 |
| Me | Me | 3,6-Cl$_2$—Q-47 |
| Me | Me | 3-Cl—Q-10 (R$^4$=Me) |
| Me | Me | 3,4-Cl$_2$—Q-10 (R$^4$=Me) |
| Me | Me | 3-CF$_3$—Q-10 (R$^4$=Me) |
| Me | Me | 3-Me—Q-34 |
| Me | Me | 4-CF$_3$—Q-24 |
| Me | Me | 4-C$_2$F$_5$—Q-24 |
| Me | Me | 4,5-Cl$_2$—Q-24 |
| Me | Me | 4-Et—5-Me—Q-24 |
| Me | Me | 5-F—Q-32 |
| Me | Me | 5-F—Q-24 |

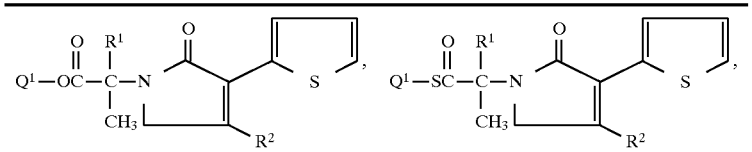

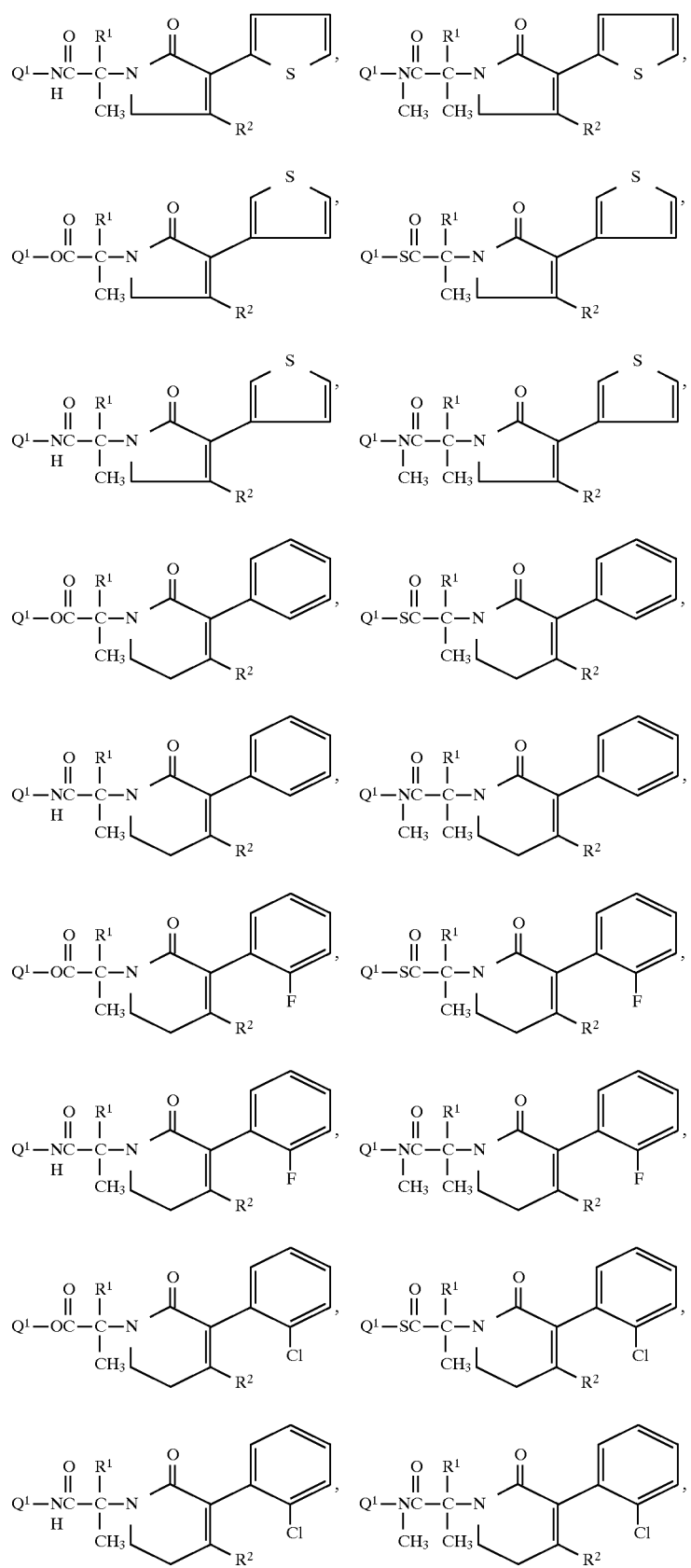

-continued
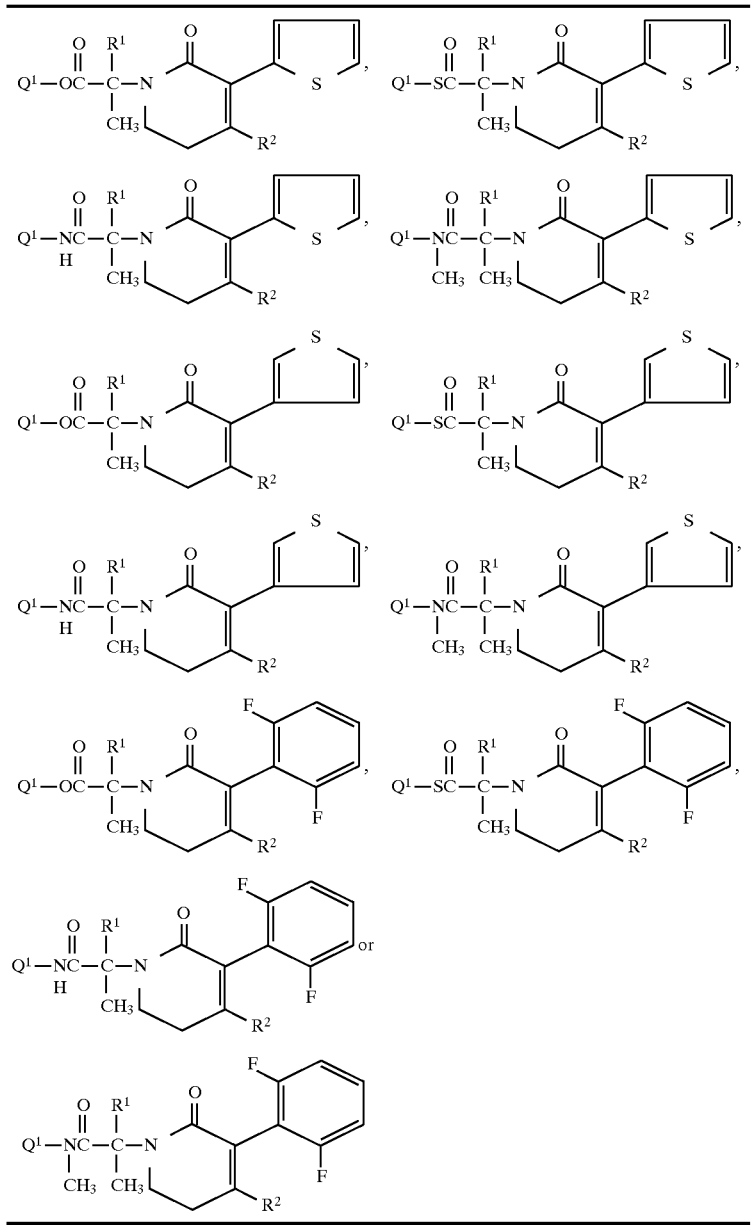
| R¹ | R² | Q¹ |
|---|---|---|
| Me | Me | H |
| Me | Et | H |
| Et | Me | H |
| Me | Me | Me |
| Me | Me | Et |
| Me | Me | Pr |
| Me | Me | i-Pr |
| Me | Me | c-Pr |
| Me | Me | Bu |
| Me | Me | t-Bu |
| Me | Me | Pen |
| Me | Me | Hex |
| Me | Me | c-Hex |
| Me | Me | All |
| Me | Me | CH=CHMe |
| Me | Me | Prop |
| Me | Me | Q-1 |
| Me | Et | Q-1 |
| Me | Me | 2-Cl—Q-1 |

-continued

| | | |
|---|---|---|
| Me | Me | 2-OMe—Q-1 |
| Me | Me | 2-NO$_2$—Q-1 |
| Me | Me | 3-NO$_2$—Q-1 |
| Me | Me | 2,5-Cl$_2$—Q-1 |
| Me | Et | 2,5-Cl$_2$—Q-1 |
| Et | Me | 2,5-Cl$_2$—Q-1 |
| Me | Me | 3-Cl—Q-1 |
| Me | Me | 2-CN—Q-1 |
| Me | Me | 2-CF$_3$—Q-1 |
| Me | Me | 2-Br—Q-1 |
| Me | Me | 2-F—Q-1 |
| Me | Me | 2-F-5-Cl—Q-1 |
| Me | Me | 2-F-5-NO$_2$—Q-1 |
| Me | Me | 2,3-Cl$_2$—Q-1 |
| Me | Me | 3,4-Cl$_2$—Q-1 |
| Me | Me | 3,5-F$_2$—Q-1 |
| Me | Me | 3-F-5-Cl—Q-1 |
| Me | Me | 3-F-5-NO$_2$—Q-1 |
| Me | Me | 3-Cl-5-NO$_2$—Q-1 |
| Me | Me | 3,5-Cl$_{2\text{-}4\text{-OMe}}$—Q-1 |
| Me | Me | 2,5-F$_2$—Q-1 |
| Me | Me | 3,5-Cl$_2$—Q-1 |
| Me | Et | 3,5-Cl$_2$—Q-1 |
| Et | Me | 3,5-Cl$_2$—Q-1 |
| Me | Me | 3-CO$_2$Et—Q-2 |
| Me | Me | 2-Me—Q-3 |
| Me | Me | 4,5-Me$_2$-3-CN—Q-6 (R$^4$:Me) |
| Me | Me | 2-CO$_2$Et—Q-7 (R$^4$:Me) |
| Me | Me | Q-8 (R$^4$:H) |
| Me | Me | 3,5-Cl—Q-9 (R$^4$:Me) |
| Me | Me | 3-Me—Q-10 (R$^4$:Me) |
| Me | Me | 3-Me—Q-16 |
| Me | Me | Q-20 |
| Me | Me | 3-Me—Q-23 |
| Me | Me | 5-Cl—Q-24 |
| Me | Me | Q-27 |
| Me | Me | 5-Cl—Q-28 |
| Me | Me | Q-32 |
| Me | Et | Q-32 |
| Me | Me | 5-Cl—Q-32 |
| Me | Me | Q-39 |
| Me | Et | Q-39 |
| Me | Me | 5-Cl—Q-40 |
| Me | Me | 2,6-Cl$_2$—Q-41 |
| Me | Me | Q-42 |
| Me | Me | Q-43 |
| Me | Me | Q-44 |
| Me | Me | Q-45 |
| Me | Me | Q-47 |
| Me | Me | Q-48 |
| Me | Me | Q-49 |
| Me | Me | Q-52 |
| Me | Me | Q-53 |
| Me | Me | Q-57 |
| Me | Et | Q-57 |
| Me | Me | Q-59 |
| Me | Me | 3-CF$_3$—Q-1 |
| Me | Me | 3-F—Q-1 |
| Me | Me | 3-Br—Q-1 |
| Me | Me | 2-Cl-5-F—Q-1 |
| Me | Me | 3,4,5-Cl$_3$—Q-1 |
| Me | Me | 2,3,5-Cl$_3$—Q-1 |
| Me | Me | 2-Cl-3,5-F$_2$—Q-1 |
| Me | Me | 2,4,5-F$_3$—Q-1 |
| Me | Me | 2,3,4,5-F$_4$—Q-1 |
| Me | Me | 2-F-3,5-Cl$_2$—Q-1 |
| Me | Me | 4-Me-5-Cl—Q-24 |
| Me | Me | 6-Cl—Q-39 |
| Me | Me | 5-Cl—Q-40 |
| Me | Me | 2,5-Cl$_2$—Q-40 |
| Me | Me | 2,6-Cl$_2$—Q-41 |
| Me | Me | 2-Cl—Q-41 |
| Me | Me | 4-Cl—Q-44 |
| Me | Me | 4,6-Cl$_2$—Q-44 |
| Me | Me | 2-Cl—Q-45 |
| Me | Me | 2,6-Cl$_2$—Q-45 |
| Me | Me | 6-Cl—Q-45 |
| Me | Me | 3,6-Cl$_2$—Q-47 |
| Me | Me | 6-Cl—Q-47 |
| Me | Me | 4,6-Cl$_2$—Q-48 |

-continued
| | | |
|---|---|---|
| Me | Me | 2-Cl-5-CF$_3$—Q-1 |
| Me | Me | 3,5-(CF$_3$)$_2$—Q-1 |
| Me | Me | 2-F-5-CF$_3$—Q-1 |
| Me | Et | 3,5-F$_2$—Q-1 |
| Me | Me | 3-i-Pr—Q-1 |
| Me | Me | 3-OCHF$_2$—Q-1 |
| Me | Me | 3-CN—Q-1 |
| Me | Me | 3-Me—Q-1 |
| Me | Me | 3-F-5-CF$_3$—Q-1 |
| Me | Me | 3-OMe—Q-1 |
| Me | Me | 3-I—Q-1 |
| Me | Me | 2-F-5-Me—Q-1 |
| Me | Me | 2-F-5-Br—Q-1 |
TABLE 3-B
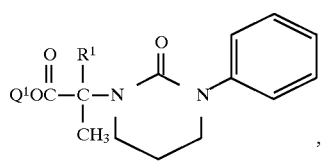
,
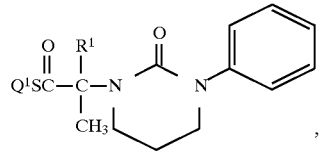
,
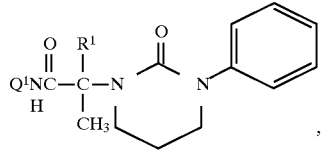
,
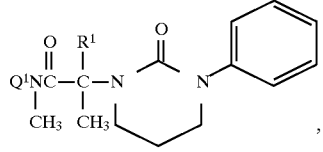
,
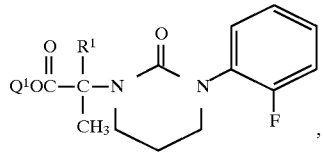
,
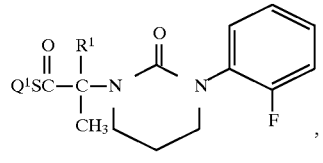
,
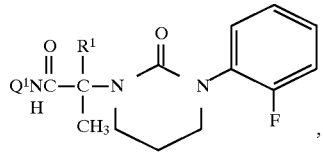
,
TABLE 3-B-continued
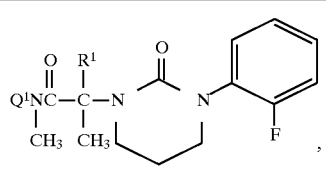
,
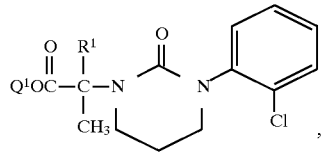
,
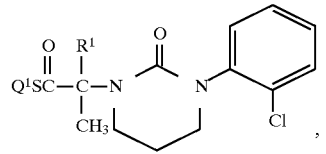
,
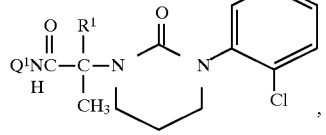
,
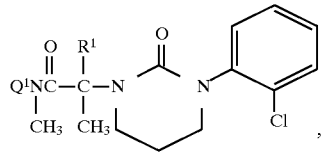
,
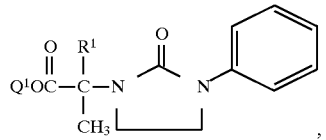
,
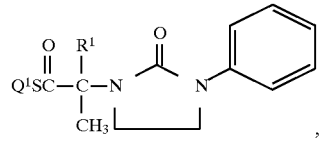
, TABLE 3-B-continued
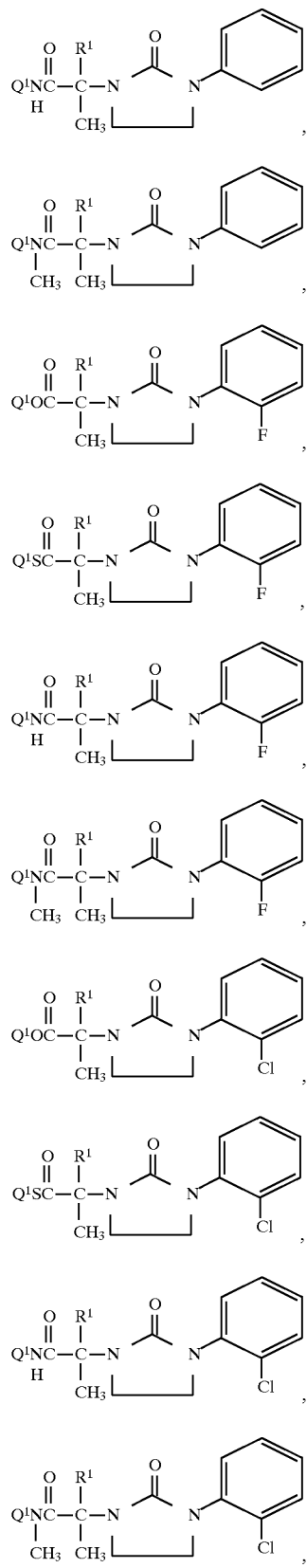
TABLE 3-B-continued
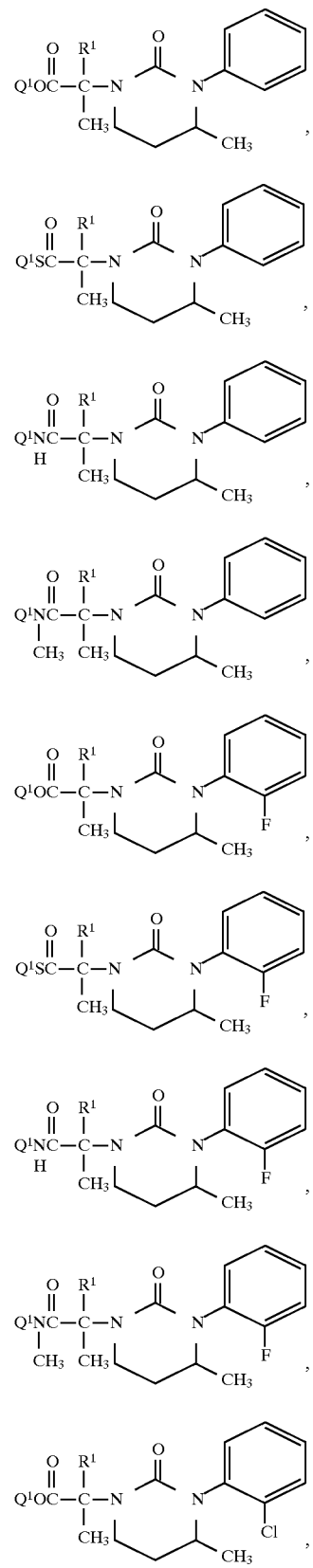

TABLE 3-B-continued

TABLE 3-B-continued

TABLE 3-B-continued

TABLE 3-B-continued
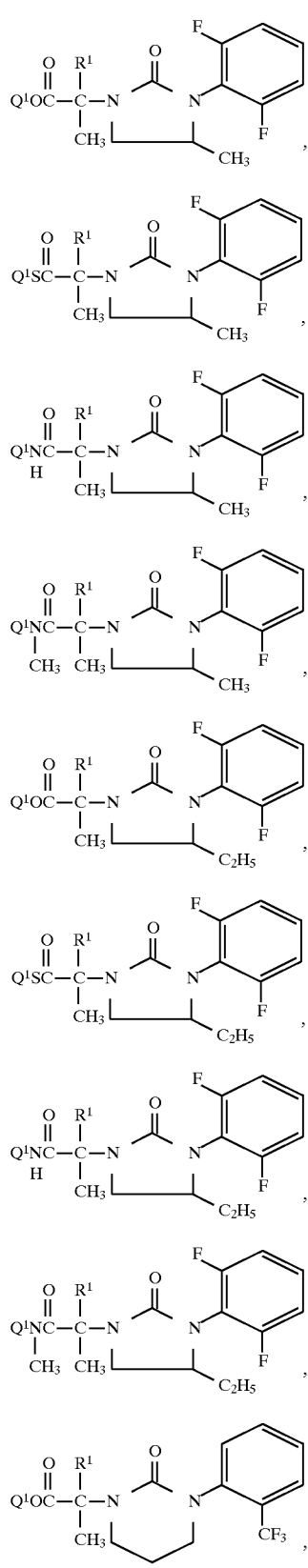
TABLE 3-B-continued
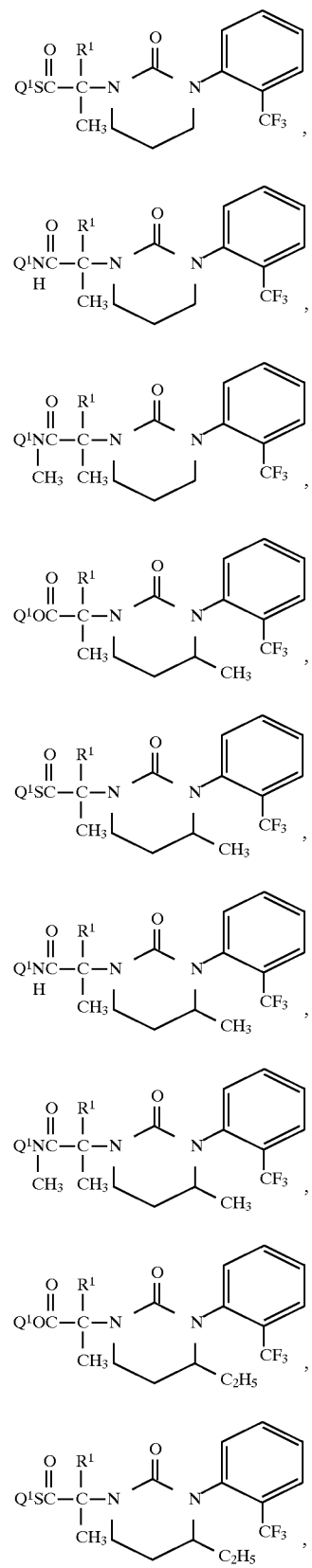

TABLE 3-B-continued
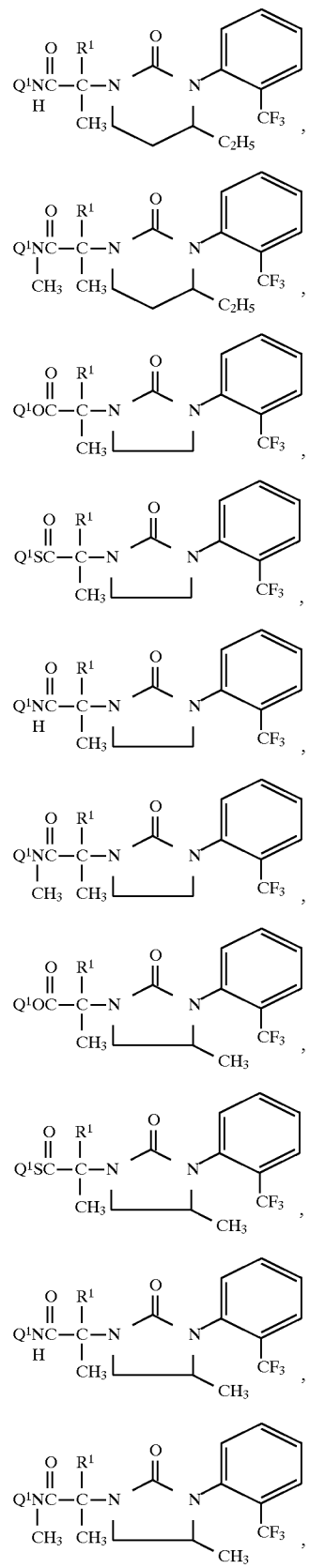
| R¹ | Q¹ |
|---|---|
| Me | H |
| Et | H |
| Me | Me |
| Me | Et |
| Me | Pr |
| Me | i-Pr |
| Me | c-Pr |
| Me | Bu |
| Me | t-Bu |
| Me | Pen |
| Me | Hex |
| Me | c-Hex |
| Me | All |
| Me | —CH=CHMe |
| Me | Prop |
| Me | Q-1 |
| Me | 2-Cl-Q-1 |
| Me | 2-OMe-Q-1 |
| Me | 2-NO₂-Q-1 |
| Me | 3-NO₂-Q-1 |
| Me | 2,5-Cl₂-Q-1 |
| Et | 2,5-Cl₂-Q-1 |
| Me | 3-Cl-Q-1 |
| Me | 2-CN-Q-1 |
| Me | 2-CF₃-Q-1 |
| Me | 2-Br-Q-1 |
| Me | 2-F-Q-1 |
| Me | 2-F-5-Cl-Q-1 |
| Me | 2-F-5-NO₂-Q-1 |
| Me | 2-Br-5-Cl-Q-1 |
| Me | 2,3-Cl₂-Q-1 |
| Me | 3,4-Cl₂-Q-1 |
| Me | 3,5-F₂-Q-1 |
| Et | 3,5-F₂-Q-1 |
| Me | 3-F-5-Cl-Q-1 |
| Me | 3-F-5-NO₂-Q-1 |
| Me | 3-Cl-5-NO₂-Q-1 |
| Me | 3,5-Br₂-Q-1 |
| Me | 2,5-Br₂-Q-1 |
| Me | 3,5-Cl₂-4-OMe-Q-1 |
| Me | 2,5-F₂-Q-1 |
| Et | 2,5-F₂-Q-1 |
| Me | 3,5-Cl₂-Q-1 |
| Et | 3,5-Cl₂-Q-1 |

TABLE 3-B-continued

| | |
|---|---|
| Me | 2,4,5-Cl$_3$-Q-1 |
| Me | 2,3,5-Cl$_3$-Q-1 |
| Me | 3,4,5-Cl$_3$-Q-1 |
| Me | 2,3,6-Cl$_3$-Q-1 |
| Me | 3-CO$_2$Et-Q-2 |
| Me | 2-Me-Q-3 |
| Me | 4,5-Me$_2$-3-CN-Q-6(R$^4$: Me) |
| Me | 2-CO$_2$Et-Q-7(R$^4$: Me) |
| Me | Q-8(R$^4$: H) |
| Me | Q-8(R$^4$: Me) |
| Me | 4-Cl-Q-8 |
| Me | 4-NO$_2$-Q-8(R$^4$: H) |
| Me | 4-NO$_2$-Q-8(R$^4$: Me) |
| Me | Q-9(R$^4$: H) |
| Me | Q-9(R$^4$: Me) |
| Me | 3-Me-Q-9(R$^4$: H) |
| Me | 3-Me-Q-9(R$^4$: Me) |
| Me | 3,5-Cl$_2$-Q-9(R$^4$: Me) |
| Me | 3,5-Me$_2$-Q-9(R$^4$: Me) |
| Me | 3-CF$_3$-5-Cl-Q-9(R$^4$: H) |
| Me | 3-CF$_3$-5-Cl-Q-9(R$^4$: Me) |
| Me | Q-10(R$^4$: H) |
| Me | Q-10(R$^4$: Me) |
| Me | 3-Me-Q-10(R$^4$: H) |
| Me | 3-Me-Q-10(R$^4$: Me) |
| Me | 3-Cl-Q-10(R$^4$: H) |
| Me | 3-Cl-Q-10(R$^4$: Me) |
| Me | 4-NO$_2$-Q-10(R$^4$: H) |
| Me | 4-NO$_2$-Q-10(R$^4$: Me) |
| Me | 3-Me-4-NO$_2$-Q-10(R$^4$: H) |
| Me | 3-Me-4-NO$_2$-Q-10(R$^4$: Me) |
| Me | 3-Me-4-Cl-Q-10(R$^4$: Me) |
| Me | 3-CF$_3$-4-NO$_2$-Q-10(R$^4$: H) |
| Me | 3-CF$_3$-4-NO$_2$-Q-10(R$^4$: Me) |
| Me | 3-CF$_3$-4-Cl-Q-10(R$^4$: Me) |
| Me | Q-11(R$^4$: H) |
| Me | Q-11(R$^4$: Me) |
| Me | 4-Cl-Q-11(R$^4$: H) |
| Me | 4,5-Cl$_2$-Q-11(R$^4$: Me) |
| Me | 2-Me-Q-12(R$^4$: H) |
| Me | 5-Me-Q-12(R$^4$: H) |
| Me | Q-13(R$^4$: Me) |
| Me | 2-Cl-Q-13(R$^4$: Me) |
| Me | 2,4-Cl$_2$-Q-13(R$^4$: Me) |
| Me | Q-14 |
| Me | Q-15 |
| Me | Q-16 |
| Me | 3-Me-Q-16 |
| Me | 3,4-Me$_2$-Q-16 |
| Me | Q-17 |
| Me | 5-Cl-Q-17 |
| Me | Q-18 |
| Me | Q-19 |
| Me | Q-20 |
| Me | Q-21 |
| Me | 3,5-Me$_2$-Q-22 |
| Me | 3-Me-Q-23 |
| Me | Q-24 |
| Me | 4-Me-Q-24 |
| Me | 4-Cl-Q-24 |
| Me | 5-Me-Q-24 |
| Me | 5-Cl-Q-24 |
| Me | 5-Br-Q-24 |
| Me | 4-Me-5-Cl-Q-24 |
| Me | 4,5-Me$_2$-Q-24 |
| Me | 2-Me-Q-25 |
| Me | 2-Cl-Q-26 |
| Me | Q-27 |
| Me | 4-Me-Q-27 |
| Me | 5-Me-Q-27 |
| Me | 5-Cl-Q-28 |
| Me | 5-Me-Q-28 |
| Me | 5-Br-Q-28 |
| Me | 5-Me-Q-29 |
| Me | 5-Me-Q-30 |
| Me | 4-Me-Q-31 |
| Me | Q-32 |
| Me | 5-F-Q-32 |
| Me | 5-Cl-Q-32 |
| Et | 5-Cl-Q-32 |
| Me | 5-Br-Q-32 |
| Me | 5-Me-Q-32 |
| Me | 5-MeS-Q-32 |
| Me | 5-MeSO-Q-32 |
| Me | 5-MeSO$_2$-Q-32 |
| Me | 5-EtS-Q-32 |
| Me | 5-EtSO-Q-32 |
| Me | 5-EtSO$_2$-Q-32 |
| Me | 5-CF$_3$-Q-32 |
| Me | Q-34 |
| Me | 5-Me-Q-35 |
| Me | Q-36(R$^4$: H) |
| Me | 3-Me-Q-37(R$^4$: H) |
| Me | Q-38(R$^4$: Me) |
| Me | Q-39 |
| Me | 3,5-Cl$_2$-Q-39 |
| Me | 3-NO$_2$-Q-39 |
| Me | 3-Me-Q-39 |
| Me | 4-Me-Q-39 |
| Me | 4,6-Me$_2$-Q-39 |
| Me | 5-Cl-Q-39 |
| Me | 5-NO$_2$-Q-39 |
| Me | 5-Me-Q-39 |
| Me | 6-Me-Q-39 |
| Me | 3-Cl-5-CF$_3$-Q-39 |
| Me | 5-CF$_3$-Q-39 |
| Me | 3-NO$_2$-6-Cl-Q-39 |
| Me | 3-NO$_2$-6-Me-Q-39 |
| Me | 4-CF$_3$-Q-39 |
| Me | 3-CO$_2$Me-Q-39 |
| Me | 3-CN-Q-39 |
| Me | 4-CF$_3$-6-Cl-Q-39 |
| Me | 2-OMe-Q-39 |
| Me | 4-OMe-Q-39 |
| Me | 4,6-Cl$_2$-Q-39 |
| Me | 6-Cl-Q-39 |
| Me | 4-Cl-Q-39 |
| Me | 4-NO$_2$-Q-39 |
| Me | 3,6-Cl$_2$-Q-39 |
| Me | Q-40 |
| Me | 2-Cl-Q-40 |
| Me | 6-Cl-Q-40 |
| Me | 6-OMe-Q-40 |
| Me | 2,6-Cl$_2$-Q-40 |
| Me | 2-NO$_2$-Q-40 |
| Me | 2-CO$_2$Me-Q-40 |
| Me | 4-Me-Q-40 |
| Me | 5-CF$_3$-Q-40 |
| Me | 5-Cl-Q-40 |
| Me | 5-Me-Q-40 |
| Me | 2,5-Cl$_2$-Q-40 |
| Me | 4-Cl-Q-40 |
| Me | 4-OMe-Q-40 |
| Me | Q-41 |
| Me | 2-Cl-Q-41 |
| Me | 2,6-Cl$_2$-Q-41 |
| Me | 2,3-Cl$_2$-Q-41 |
| Me | 2,6-(CF$_3$)$_2$-Q-41 |
| Me | 2,6-Me$_2$-Q-41 |
| Me | 2-Me-Q-41 |
| Me | 4-OMe-Q-41 |
| Me | 3-NO$_2$-Q-41 |
| Me | Q-42 |
| Me | 6-Cl-Q-42 |
| Me | 6-OMe-Q-42 |
| Me | Q-43 |
| Me | 6-CO$_2$Et-Q-43 |
| Me | Q-44 |
| Me | 4,6-Cl$_2$-Q-44 |
| Me | 4-Cl-6-Me-Q-44 |
| Me | 4,6-(OMe)$_2$-Q-44 |
| Me | 4-Cl-6-OMe-Q-44 |
| Me | 4-Me-6-OMe-Q-44 |
| Me | 4-Me-Q-44 |
| Me | 4,6-Me$_2$-Q-44 |
| Me | 5-NO$_2$-Q-44 |
| Me | 5-Cl-Q-44 |
| Me | 4-OMe-Q-44 |

TABLE 3-B-continued

| | |
|---|---|
| Me | 4,6-Cl$_2$-5-Me-Q-44 |
| Me | 4-Cl-Q-44 |
| Me | 4-OMe-6-CF$_3$-Q-44 |
| Me | 4,6-(SMe)$_2$-Q-44 |
| Me | Q-45 |
| Me | 2-Cl-Q-45 |
| Me | 2-OMe-Q-45 |
| Me | 2-SMe-Q-45 |
| Me | 5-CN-Q-45 |
| Me | 2-Cl-5-CN-Q-45 |
| Me | 6-Cl-Q-45 |
| Me | 6-OMe-Q-45 |
| Me | 5-CO$_2$Me-Q-45 |
| Me | 2,6-Cl$_2$-Q-45 |
| Me | 2,6-Me$_2$-Q-45 |
| Me | 2,6-(OMe)$_2$-Q-45 |
| Me | 2-Cl-5-F-Q-45 |
| Me | 2,5-Cl$_2$-Q-45 |
| Me | 2-Me-6-OMe-Q-45 |
| Me | Q-46 |
| Me | 4,6-Cl$_2$-Q-46 |
| Me | 2,4-Cl$_2$-Q-46 |
| Me | 4-Cl-Q-46 |
| Me | 2-Cl-Q-46 |
| Me | Q-47 |
| Me | 3-CO$_2$Me-Q-47 |
| Me | 3,5-Me$_2$-Q-47 |
| Me | 6-Cl-Q-47 |
| Me | 3,6-Cl$_2$-Q-47 |
| Me | Q-48 |
| Me | 4-Cl-Q-48 |
| Me | 4-Me-Q-48 |
| Me | 4,6-Cl$_2$-Q-48 |
| Me | 4,6-(OMe)$_2$-Q-48 |
| Me | 4,6-Me$_2$-Q-48 |
| Me | 4-Me-6-OMe-Q-48 |
| Me | Q-49 |
| Me | 5,6-Me$_2$-Q-49 |
| Me | Q-50 |
| Me | 4-SMe-6-Me-Q-51 |
| Me | Q-52 |
| Me | 1-NO$_2$-Q-52 |
| Me | 3-NO$_2$-Q-52 |
| Me | 4-OMe-Q-52 |
| Me | 1-Br-Q-52 |
| Me | 1-Cl-Q-52 |
| Me | Q-53 |
| Me | 2-NO$_2$-Q-53 |
| Me | 2-Me-Q-53 |
| Me | 8-NO$_2$-Q-53 |
| Me | 4-Cl-Q-53 |
| Me | Q-54(R$^4$: H) |
| Me | Q-55(R$^4$: H) |
| Me | Q-56 |
| Me | 5-Cl-Q-56 |
| Me | 6-Cl-Q-56 |
| Me | Q-57 |
| Me | 5-Cl-Q-57 |
| Me | 6-Cl-Q-57 |
| Me | Q-58(R$^4$: H) |
| Me | Q-59 |
| Me | 4-OMe-Q-59 |
| Me | 4-Cl-Q-59 |
| Me | 4-Me-Q-59 |
| Me | Q-60 |
| Me | Q-61 |
| Me | 2-Me-Q-61 |
| Me | 2-Cl-Q-61 |
| Me | Q-62 |
| Me | Q-63 |
| Me | Q-64 |
| Me | Q-65 |
| Me | 3-Me-Q-65 |
| Me | 6-Cl-Q-65 |
| Me | 3-Cl-Q-65 |
| Me | Q-66 |
| Me | 8-Cl-Q-66 |
| Me | Q-67 |
| Me | 5-t-Bu-Q-32 |
| Me | 5-c-Pr-Q-32 |
| Me | 3-CF$_3$-Q-1 |
| Me | 2-Cl-5-CF$_3$-Q-1 |
| Me | 2-Cl-5-NO$_2$-Q-1 |
| Me | 2-Cl-3,5-F$_2$-Q-1 |
| Me | 2-Cl-5-F-Q-1 |
| Me | 2,4,5-F$_3$-Q-1 |
| Me | 2,3,4,5-F$_4$-Q-1 |
| Me | 2-F-5-CF$_3$-Q-1 |
| Me | 3,5-(CF$_3$)$_2$-Q-1 |
| Me | 2,6-F$_2$-Q-1 |
| Me | 2-Cl-5-CO$_2$i-Pr-Q-1 |
| Me | 4-Br-Q-8(R$^4$ = Me) |
| Me | 3-Et-Q-1 |
| Me | 3-i-Pr-Q-1 |
| Me | 2,5-(CF$_3$)$_2$-Q-1 |
| Me | 3-CF$_3$-Q-10(R$^4$ = Me) |
| Me | 2,3,6-F$_3$-Q-1 |
| Me | 3-F-5-CF$_3$-Q-1 |
| Me | 3-OCHF$_2$-Q-1 |
| Me | 3-Me-Q-1 |
| Me | 2-F-5-Br-Q-1 |
| Me | 2-Cl-5-Br-Q-1 |
| Me | 2-F-5-Me-Q-1 |
| Me | 2-F-5-Et-Q-1 |
| Me | 2-F-5-i-Pr-Q-1 |
| Me | 2-Cl-5-Me-Q-1 |
| Me | 2-Cl-5-Et-Q-1 |
| Me | 2-Cl-5-i-Pr-Q-1 |
| Me | 3-CN-Q-1 |
| Me | 3-F-5-Me-Q-1 |
| Me | 3-F-5-Et-Q-1 |
| Me | 3-F-5-i-Pr-Q-1 |
| Me | 3-Cl-5-Me-Q-1 |
| Me | 3-Cl-5-Et-Q-1 |
| Me | 3-Cl-5-i-Pr-Q-1 |
| Me | 2-Me-5-F-Q-1 |
| Me | 2-Me-5-Cl-Q-1 |
| Me | 2-Me-5-Br-Q-1 |
| Me | 2,5-(Me)$_2$-Q-1 |
| Me | 2-Me-5-i-Pr-Q-1 |
| Me | 2-Me-5-t-Bu-Q-1 |
| Me | 2-F-5-OCHF$_2$-Q-1 |
| Me | 2-F-5-OCF$_3$-Q-1 |
| Me | 2-Cl-5-OCHF$_2$-Q-1 |
| Me | 2-Cl-5-OCF$_3$-Q-1 |
| Me | 2-Me-5-OCHF$_2$-Q-1 |
| Me | 2-Me-5-OCF$_3$-Q-1 |
| Me | 3-OMe-Q-1 |
| Me | 2-F-5-OMe-Q-1 |
| Me | 2-Cl-5-OMe-Q-1 |
| Me | 3-F-5-OMe-Q-1 |
| Me | 3-Cl-5-OMe-Q-1 |
| Me | 3-Br-Q-1 |
| Me | 2-Cl-5-CN-Q-1 |
| Me | 3-I-Q-1 |
| Et | 3-Cl-Q-1 |
| Et | 2-F-5-Cl-Q-1 |
| Et | 2-Cl-5-CF$_3$-Q-1 |
| Me | 3-OCF$_3$-Q-1 |
| Me | 3-F-Q-1 |
| Me | 3-CO$_2$Me-Q-1 |
| Me | 3-SMe-Q-1 |
| Me | 3-SOMe-Q-1 |
| Me | 3-SO$_2$Me-Q-1 |
| Me | 3-Cl-5-CF$_3$-Q-1 |
| Me | 3-F-5-I-Q-1 |
| Me | 3-Cl-5-Br-Q-1 |
| Me | 3-Br-5-CF$_3$-Q-1 |
| Me | 3-Me-Q-34 |
| Me | 3-Cl-Q-34 |
| Me | 4-CF$_3$-Q-24 |
| Me | 4-C$_2$F$_5$-Q-24 |
| Me | 4-CF$_3$-5-Cl-Q-24 |
| Me | 4-CF$_3$-5-Br-Q-24 |
| Me | 4-Et-5-Me-Q-24 |
| Me | 2-F-5-CN-Q-1 |

TABLE 3-C
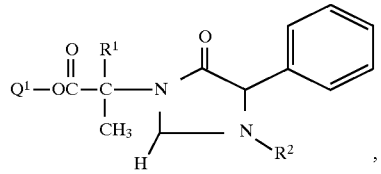
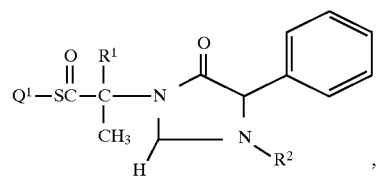
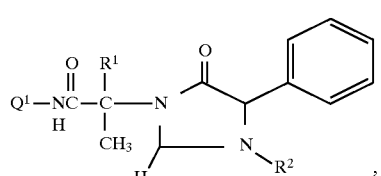
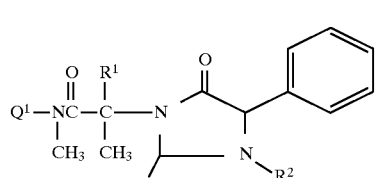
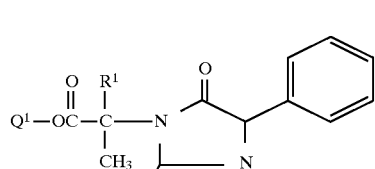
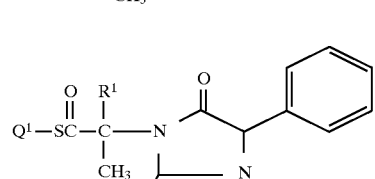
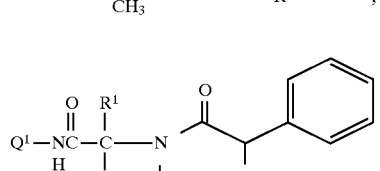
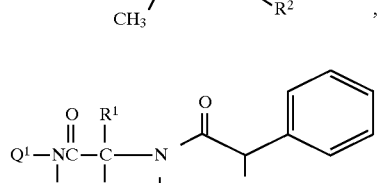
TABLE 3-C-continued
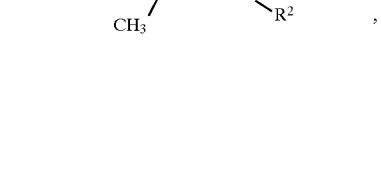
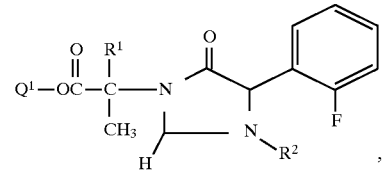
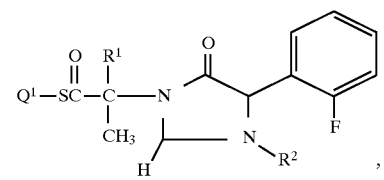
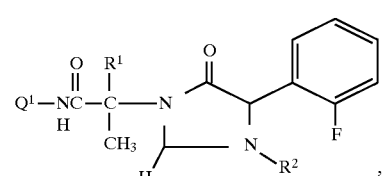
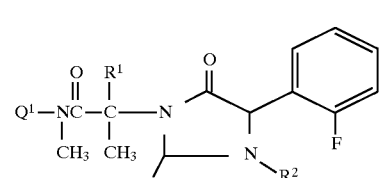
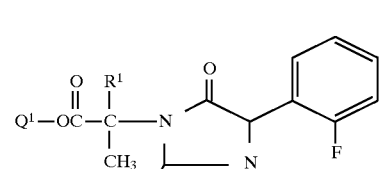
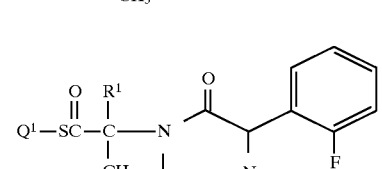
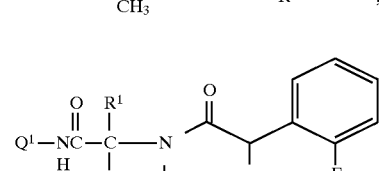

TABLE 3-C-continued
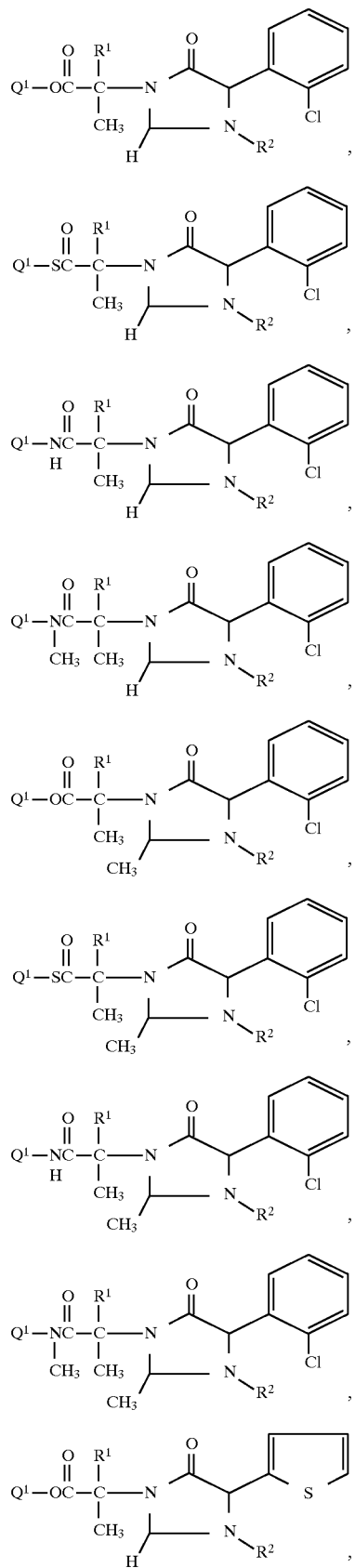
TABLE 3-C-continued
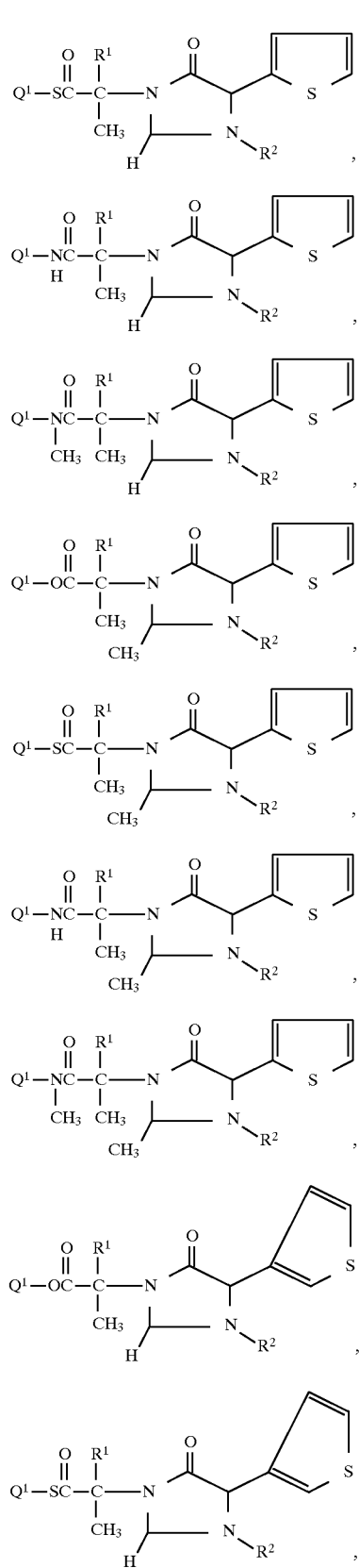

TABLE 3-C-continued
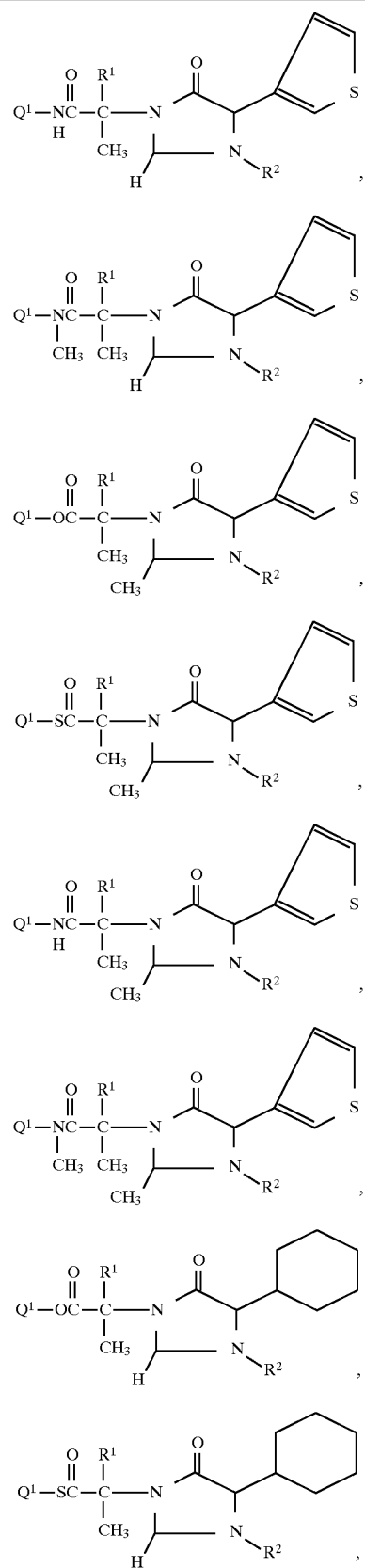
TABLE 3-C-continued
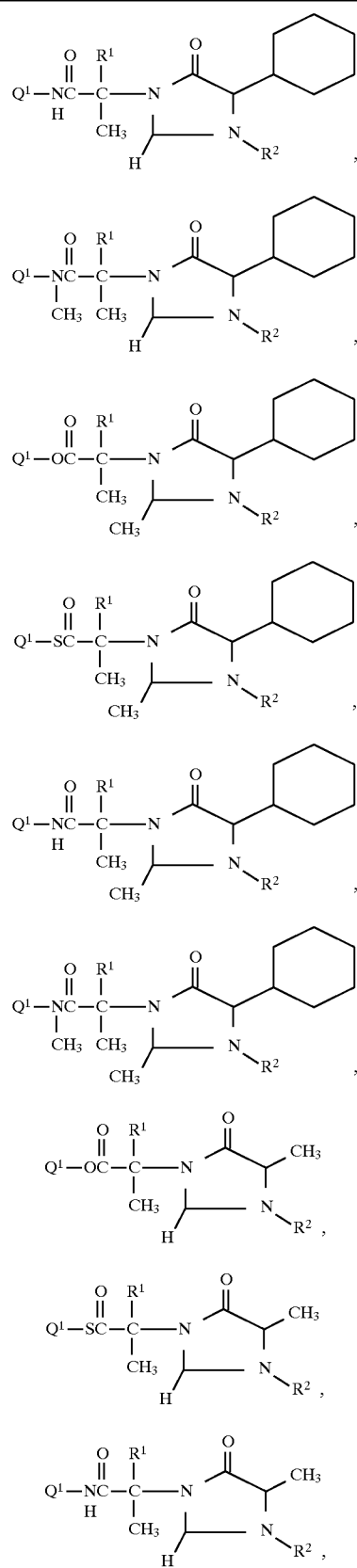

TABLE 3-C-continued

TABLE 3-C-continued

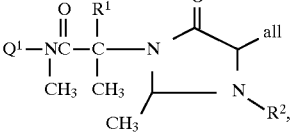

| R¹ | R² | Q¹ |
|---|---|---|
| Me | Me | Q-8 (R⁴:H) |
| Me | Me | Q-8 (R⁴:Me) |
| Me | Me | 4-Cl—Q-8 (R⁴:Me) |
| Me | Me | 4-NO₂—Q-8 (R⁴:H) |
| Me | Me | 4-NO₂—Q-8 (R⁴:Me) |
| Me | Me | Q-9 (R⁴:H) |
| Me | Me | Q-9 (R⁴:Me) |
| Me | Me | 3-Me—Q-9 (R⁴:H) |
| Me | Me | 3-Me—Q-9 (R⁴:Me) |
| Me | Me | 3,5-Cl₂—Q-9 (R⁴:Me) |
| Me | Me | 3,5-Me₂—Q-9 (R⁴:Me) |
| Me | Me | 3-CF₃-5-Cl—Q-9 (R⁴:H) |
| Me | Me | 3-CF₃-5-Cl—Q-9 (R⁴:Me) |
| Me | Me | Q-10 (R⁴:H) |
| Me | Me | Q-10 (R⁴:Me) |
| Me | Me | 3-Me—Q-10 (R⁴:H) |
| Me | Me | 3-Me—Q-10 (R⁴:Me) |
| Me | Me | 4-NO₂—Q-10 (R⁴:H) |
| Me | Me | 4-NO₂—Q-10 (R⁴:Me) |
| Me | Me | 3-Me-4-NO₂—Q-10 (R⁴:H) |
| Me | Me | 3-Me-4-NO₂—Q-10 (R⁴:Me) |
| Me | Me | 3-Me-4-Cl—Q-10 (R⁴:Me) |
| Me | Me | 3-CF₃-4-NO₂—Q-10 (R⁴:H) |
| Me | Me | 3-CF₃-4-NO₂—Q-10 (R⁴:Me) |
| Me | Me | 3-CF₃-4-Cl—Q-10 (R⁴:Me) |
| Me | Me | Q-11 (R⁴:H) |
| Me | Me | Q-11 (R⁴:Me) |
| Me | Me | 2-Me—Q-12 (R⁴:H) |
| Me | Me | 5-Me—Q-12 (R⁴:H) |
| Me | Me | Q-13 (R⁴:Me) |
| Me | Me | Q-14 |
| Me | Me | Q-15 |
| Me | Me | Q-16 |
| Me | Me | 3-Me—Q-16 |
| Me | Et | 3-Me—Q-16 |
| Me | Me | 3,4-Me₂—Q-16 |
| Me | Me | Q-17 |
| Me | Me | Q-18 |
| Me | Me | Q-19 |
| Me | Me | Q-20 |
| Me | Et | Q-20 |
| Et | Me | Q-20 |
| Me | Me | Q-21 |
| Me | Me | 3,5-Me₂—Q-22 |
| Me | Me | 3-Me—Q-23 |
| Me | Et | 3-Me—Q-23 |
| Me | Me | Q-24 |
| Me | Et | Q-24 |
| Me | Me | 4-Me—Q-24 |
| Me | Me | 4-Cl—Q-24 |
| Me | Me | 5-Me—Q-24 |
| Me | Me | 5-Cl—Q-24 |
| Me | Me | 5-Br—Q-24 |
| Me | Me | 4-Me-5-Cl—Q-24 |
| Me | Me | 4,5-Me₂—Q-24 |
| Me | Me | 2-Me—Q-25 |
| Me | Me | 2-Cl—Q-26 |
| Me | Me | Q-27 |
| Me | Et | Q-27 |
| Et | Me | Q-27 |
| Me | Me | 4-Me—Q-27 |
| Me | Me | 5-Me—Q-27 |
| Me | Me | 5-Cl—Q-28 |
| Me | Me | 5-Me—Q-28 |
| Me | Me | 5-Me—Q-29 |
| Me | Me | 5-Me—Q-30 |
| Me | Me | 4-Me—Q-31 |
| Me | Me | Q-32 |
| Me | Me | 5-Cl—Q-32 |
| Me | Me | 5-Me—Q-32 |
| Me | Me | 5-MeS—Q-32 |
| Me | Me | 5-MeSO—Q-32 |
| Me | Me | 5-MeSO₂—Q-32 |
| Me | Me | 5-EtS—Q-32 |
| Me | Me | 5-EtSO—Q-32 |
| Me | Me | 5-EtSO₂—Q-32 |
| Me | Me | 5-CF₃—Q-32 |
| Me | Me | 5-Me—Q-33 |
| Me | Me | Q-34 |
| Me | Me | 4-Me—Q-35 |
| Me | Me | Q-36 (R⁴:H) |
| Me | Me | 3-Me—Q-37 (R⁴:H) |
| Me | Me | Q-38 (R⁴:Me) |
| Me | Me | Q-39 |
| Me | Et | Q-39 |
| Me | Me | 3,5-Cl₂—Q-39 |
| Me | Me | 3-NO₂—Q-39 |
| Me | Me | 3-Me—Q-39 |
| Me | Me | 4-Me—Q-39 |
| Me | Me | 4,6-Me₂—Q-39 |
| Me | Me | 5-Cl—Q-39 |
| Me | Me | 5-NO₂—Q-39 |
| Me | Me | 5-Me—Q-39 |
| Me | Me | 6-Me—Q-39 |
| Me | Me | 3-Cl-5-CF₃-Q-39 |
| Me | Me | 5-CF₃—Q-39 |
| Me | Me | 3-NO₂-6-Cl—Q-39 |
| Me | Me | 3-NO₂-6-Me—Q-39 |
| Me | Me | 4-CF₃—Q-39 |
| Me | Me | 3-CO₂Me—Q-39 |
| Me | Me | 3-CN—Q-39 |
| Me | Me | 4-CF₃-6-Cl—Q-39 |
| Me | Me | 2-OMe—Q-39 |
| Me | Me | 4-OMe—Q-39 |
| Me | Me | 4,6-Cl₂—Q-39 |
| Me | Me | 6-Cl—Q-39 |
| Me | Me | 4-Cl—Q-39 |
| Me | Me | 4-NO₂—Q-39 |
| Me | Me | Q-40 |
| Me | Et | Q-40 |
| Me | Me | 2-Cl—Q-40 |
| Me | Me | 6-Cl—Q-40 |
| Me | Me | 6-OMe—Q-40 |
| Me | Me | 2,6-Cl₂—Q-40 |
| Me | Me | 2-NO₂—Q-40 |
| Me | Me | 2-CO₂Me—Q-40 |
| Me | Me | 4-Me—Q-40 |
| Me | Me | 5-CF₃—Q-40 |
| Me | Me | 5-Cl—Q-40 |
| Me | Me | 5-Me—Q-40 |
| Me | Me | 2,5-Cl—Q-40 |
| Me | Me | 4-Cl—Q-40 |
| Me | Me | 4-OMe—Q-40 |
| Me | Me | Q-41 |
| Et | Me | Q-41 |
| Me | Me | 2-Cl—Q-41 |
| Me | Me | 2,6-Cl₂—Q-41 |
| Me | Me | 2,3-Cl₂—Q-41 |
| Me | Me | 2,6-(CF₃)₂—Q-41 |
| Me | Me | 2,6-Me₂—Q-41 |
| Me | Et | 2-Me—Q-41 |
| Me | Me | 2-OMe—Q-41 |
| Me | Me | 3-NO₂—Q-41 |
| Me | Me | Q-42 |
| Me | Me | 6-Cl—Q-42 |
| Me | Me | 6-OMe—Q-42 |
| Me | Me | Q-43 |
| Me | Me | 6-CO₂Et—Q-43 |
| Me | Me | Q-44 |
| Me | Me | 4,6-Cl₂—Q-44 |
| Me | Me | 4-Cl-6-Me—Q-44 |
| Me | Me | 4,6-(OMe)₂—Q-44 |
| Me | Me | 4-Cl-6-OMe—Q-44 |
| Me | Me | 4-Me-6-OMe—Q-44 |
| Me | Me | 4-Me—Q-44 |
| Me | Me | 4,6-Me₂—Q-44 |
| Me | Me | 5-NO₂—Q-44 |
| Me | Me | 5-Cl—Q-44 |

TABLE 3-C-continued

| | | |
|---|---|---|
| Me | Me | 4-OMe—Q-44 |
| Me | Me | 4,6-Cl$_2$-5-Me—Q-44 |
| Me | Me | 4-Cl—Q-44 |
| Me | Me | 4-OMe-6-CF$_3$—Q-44 |
| Me | Me | 4,6-(SMe)$_2$—Q-44 |
| Me | Me | Q-45 |
| Me | Me | 2-Cl—Q-45 |
| Me | Me | 2-OMe—Q-45 |
| Me | Me | 2-SMe—Q-45 |
| Me | Me | 5-CN—Q-45 |
| Me | Me | 2-Cl-5-CN—Q-45 |
| Me | Me | 6-Cl—Q-45 |
| Me | Me | 6-OMe—Q-45 |
| Me | Me | 5-CO$_2$Me—Q-45 |
| Me | Me | 2,6-Cl$_2$—Q-45 |
| Me | Me | 2,6-Me$_2$—Q-45 |
| Me | Me | 2,6-(OMe)$_2$—Q-45 |
| Me | Me | 2-Cl-5-F—Q-45 |
| Me | Me | 2,5-Cl$_2$—Q-45 |
| Me | Me | 2-Me-6-OMe—Q-45 |
| Me | Me | Q-46 |
| Me | Me | 4,6-Cl$_2$—Q-46 |
| Me | Me | 2,4-Cl$_2$—Q-46 |
| Me | Me | 4-Cl—Q-46 |
| Me | Me | 2-Cl—Q-46 |
| Me | Me | Q-47 |
| Me | Me | 3-CO$_2$Me—Q-47 |
| Me | Me | 3,5-Me$_2$—Q-47 |
| Me | Me | Q-48 |
| Me | Me | 4-Cl—Q-48 |
| Me | Me | 4-Me—Q-48 |
| Me | Me | 4,6-Cl$_2$—Q-48 |
| Me | Me | 4,6-(OMe)$_2$—Q-48 |
| Me | Me | 4,6-Me$_2$—Q-48 |
| Me | Me | 4-Me-6-OMe—Q-48 |
| Me | Me | Q-49 |
| Me | Me | 5,6-Me$_2$—Q-49 |
| Me | Me | Q-50 |
| Me | Et | Q-50 |
| Me | Me | 4-SCH$_3$-6-CH$_3$—Q-51 |
| Me | Me | Q-52 |
| Me | Me | 1-NO$_2$—Q-52 |
| Me | Me | 3-NO$_2$—Q-52 |
| Me | Me | 4-OMe—Q-52 |
| Me | Me | 1-Br—Q-52 |
| Me | Me | 1-Cl—Q-52 |
| Me | Me | Q-53 |
| Me | Me | 2-NO$_2$—Q-53 |
| Me | Me | 2-Me—Q-53 |
| Me | Me | 8-NO$_2$—Q-53 |
| Me | Me | 4-Cl—Q-53 |
| Me | Me | Q-54 (R$^4$:H) |
| Me | Me | Q-55 (R$^4$:H) |
| Me | Me | Q-56 |
| Me | Me | 5-Cl—Q-56 |
| Me | Me | 6-Cl—Q-56 |
| Me | Me | Q-57 |
| Me | Me | 5-Cl—Q-57 |
| Me | Me | 6-Cl—Q-57 |
| Me | Me | Q-58 (R$^4$:H) |
| Me | Me | Q-59 |
| Me | Me | 4-OMe—Q-59 |
| Me | Me | 4-Cl—Q-59 |
| Me | Me | 4-Me—Q-59 |
| Me | Me | Q-60 |
| Me | Me | Q-61 |
| Me | Me | 2-Me—Q-61 |
| Me | Me | 2-Cl—Q-61 |
| Me | Me | Q-62 |
| Me | Me | Q-63 |
| Me | Me | Q-64 |
| Me | Me | Q-65 |
| Me | Me | 3-Me—Q-65 |
| Me | Me | 6-Cl—Q-65 |
| Me | Me | 3-Cl—Q-65 |
| Me | Me | Q-66 |
| Me | Me | 8-Cl—Q-66 |
| Me | Me | Q-67 |
| Me | Me | 5-t-Bu—Q-32 |

TABLE 3-C-continued

| | | |
|---|---|---|
| Me | Me | H |
| Me | Et | H |
| Et | Me | H |
| Me | Me | Me |
| Me | Me | Et |
| Me | Me | Pr |
| Me | Me | i-Pr |
| Me | Me | c-Pr |
| Me | Me | Bu |
| Me | Me | t-Bu |
| Me | Me | Pen |
| Me | Me | Hex |
| Me | Me | c-Hex |
| Me | Me | All |
| Me | Me | —CH═CHMe |
| Me | Me | Prop |
| Me | Me | Q-1 |
| Me | Et | Q-1 |
| Me | Me | 2-Cl—Q-1 |
| Me | Me | 2-OMe—Q-1 |
| Me | Me | 2-NO$_2$—Q-1 |
| Me | Me | 3-NO$_2$—Q-1 |
| Me | Me | 2,5-Cl$_2$—Q-1 |
| Me | Et | 2,5-Cl$_2$—Q-1 |
| Et | Me | 2,5-Cl$_2$—Q-1 |
| Me | Me | 3-Cl—Q-1 |
| Me | Me | 2-CN—Q-1 |
| Me | Me | 2-CF$_3$—Q-1 |
| Me | Me | 2-Br—Q-1 |
| Me | Me | 2-F—Q-1 |
| Me | Me | 2-F-5-Cl—Q-1 |
| Me | Me | 2-F-5-NO$_2$—Q-1 |
| Me | Me | 2,3-Cl$_2$—Q-1 |
| Me | Me | 3,4-Cl$_2$—Q-1 |
| Me | Me | 3,5-F$_2$—Q-1 |
| Me | Me | 3-F-5-Cl—Q-1 |
| Me | Me | 3-F-5-NO$_2$—Q-1 |
| Me | Me | 3-Cl-5-NO$_2$—Q-1 |
| Me | Me | 3,5-Cl$_2$-4-OMe—Q-1 |
| Me | Me | 2,5-F$_2$—Q-1 |
| Me | Me | 3,5-Cl$_2$—Q-1 |
| Me | Et | 3,5-Cl$_2$—Q-1 |
| Et | Me | 3,5-Cl$_2$—Q-1 |
| Me | Me | 3-CO$_2$Et—Q-2 |
| Me | Me | 2-Me—Q-3 |
| Me | Me | 4,5-Me$_2$-3-CN—Q-6 (R$^4$:Me) |
| Me | Me | 2-CO$_2$Et—Q-7 (R$^4$:Me) |
| Me | Et | Et |
| Me | Et | H |
| Me | Et | Q-1 |
| Me | Et | 2-OMe—Q-1 |
| Me | Et | 2-OMe-5-Cl—Q-1 |
| Me | Et | c-Hex |
| Me | Et | 4-OMe—Q-1 |
| Me | Et | 3,5-(OMe)$_2$—Q-1 |
| Me | Et | 2,5-F$_2$—Q-1 |
| Me | Et | 2-Et—Q-1 |
| Me | Et | Prop |
| Me | Et | 3-Cl—Q-1 |
| Me | Et | 2-Cl—Q-1 |
| Me | Et | 4-Cl—Q-1 |
| Me | Et | 3-Br—Q-1 |
| Me | Et | 2,4,5-Cl$_3$—Q-1 |
| Me | Et | 3-NO$_2$—Q-1 |
| Me | Et | 2-NO$_2$—Q-1 |
| Me | Et | 2,3-Cl$_2$—Q-1 |
| Me | Et | 2,4-Cl$_2$—Q-1 |
| Me | Et | 3,4-Cl$_2$—Q-1 |
| Me | Et | 3,5-(CF$_3$)$_2$—Q-1 |
| Me | Et | Q-53 |
| Me | Et | 5-Me—Q-32 |
| Me | Et | 3,5-(CO$_2$Me)$_2$—Q-1 |
| Me | Et | 5-Cl—Q-24 |
| Me | Me | 3,4,5-Cl$_3$—Q-1 |
| Me | Me | 3-Br—Q-1 |

TABLE 3-D
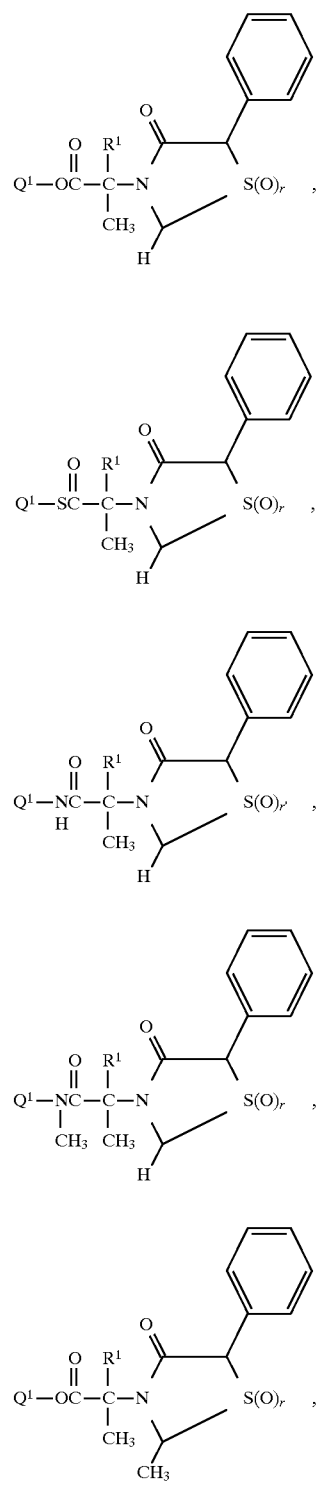
TABLE 3-D-continued
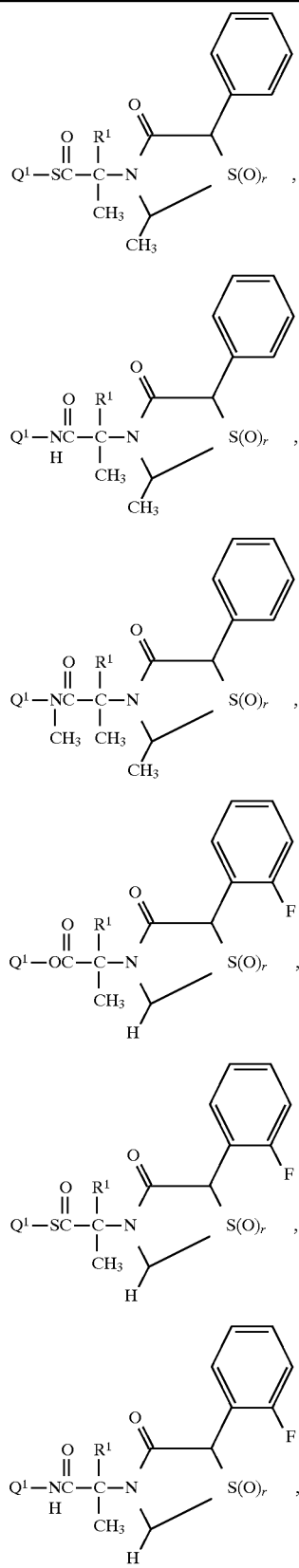

TABLE 3-D-continued
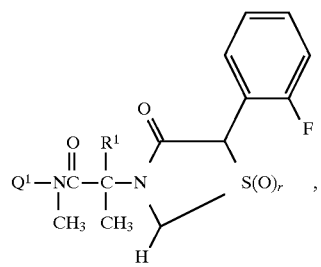
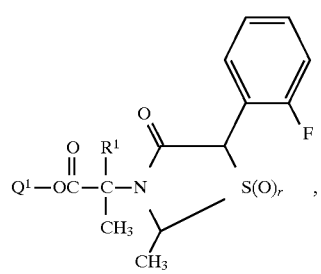
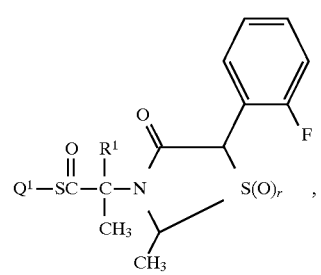
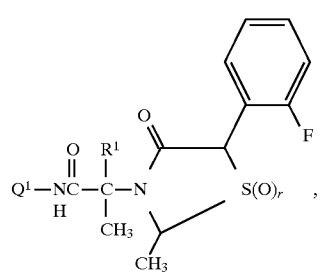
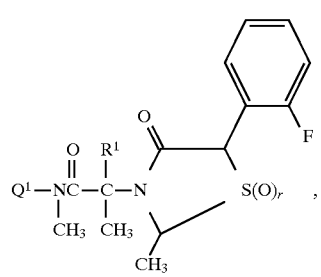
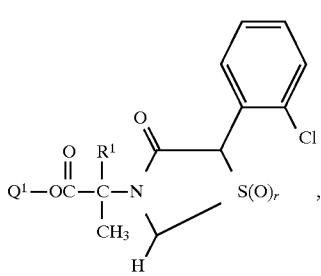
TABLE 3-D-continued
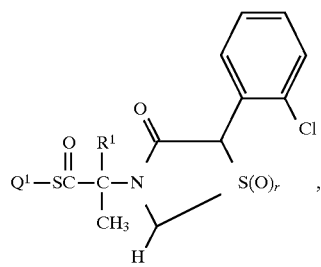

TABLE 3-D-continued
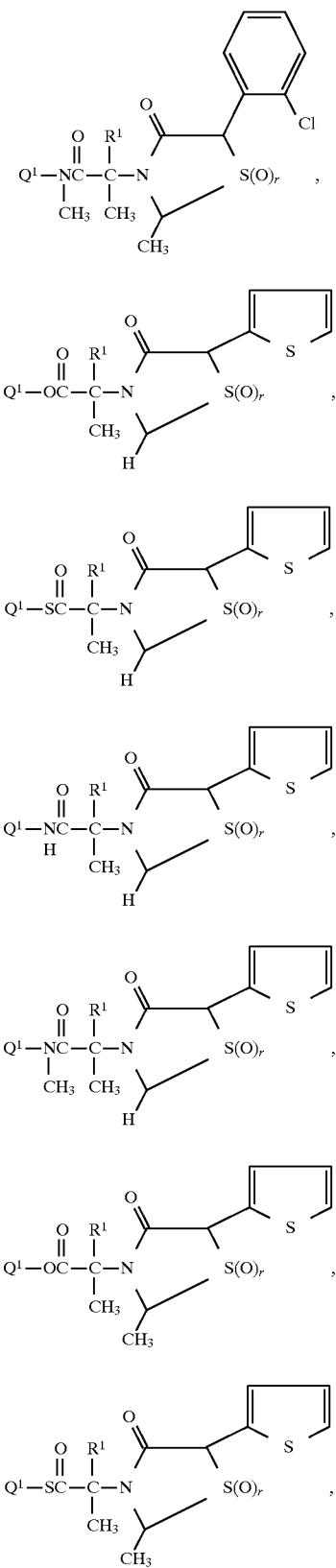
TABLE 3-D-continued
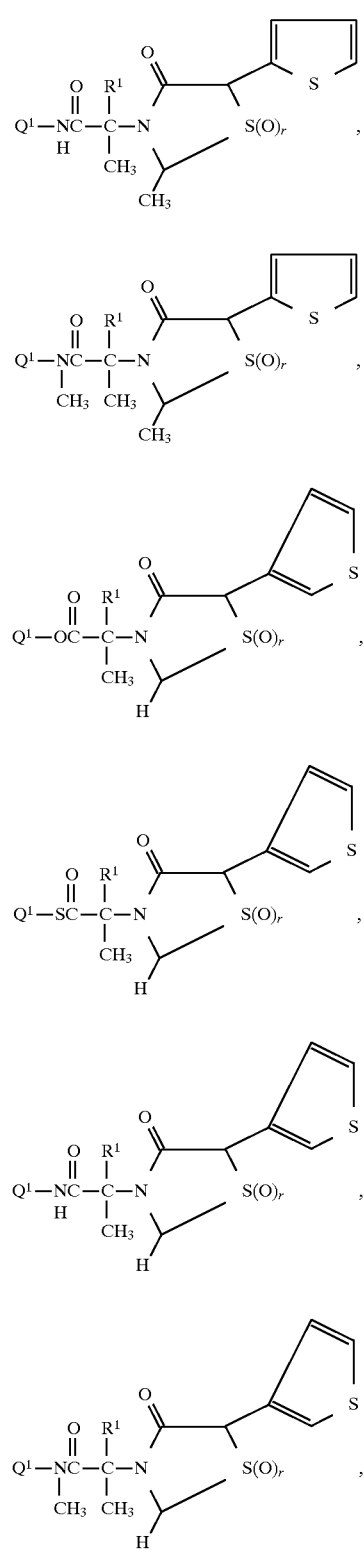

TABLE 3-D-continued $$Q^1-OC-\underset{\underset{CH_3}{|}}{\overset{\overset{R^1}{|}}{C}}-\underset{\underset{CH_3}{|}}{\overset{O}{\overset{||}{C}}}-N\underset{}{\overset{}{\diagdown}}\underset{S(O)_r}{\overset{}{\diagdown}}\underset{}{\overset{S}{\diagup}}$$ , $$Q^1-SC-\underset{\underset{CH_3}{|}}{\overset{\overset{R^1}{|}}{C}}-\underset{\underset{CH_3}{|}}{\overset{O}{\overset{||}{C}}}-N\underset{}{\overset{}{\diagdown}}\underset{S(O)_r}{\overset{}{\diagdown}}\underset{}{\overset{S}{\diagup}}$$ , $$Q^1-\underset{H}{\overset{O}{\overset{||}{NC}}}-\underset{\underset{CH_3}{|}}{\overset{\overset{R^1}{|}}{C}}-\underset{\underset{CH_3}{|}}{\overset{O}{\overset{||}{C}}}-N\underset{}{\overset{}{\diagdown}}\underset{S(O)_r}{\overset{}{\diagdown}}\underset{}{\overset{S}{\diagup}}$$ or $$Q^1-\underset{CH_3}{\overset{O}{\overset{||}{NC}}}-\underset{\underset{CH_3}{|}}{\overset{\overset{R^1}{|}}{C}}-\underset{\underset{CH_3}{|}}{\overset{O}{\overset{||}{C}}}-N\underset{}{\overset{}{\diagdown}}\underset{S(O)_r}{\overset{}{\diagdown}}\underset{}{\overset{S}{\diagup}}$$

| $R^1$ | r | $Q^1$ |
|---|---|---|
| Me | 0 | H |
| Me | 1 | H |
| Et | 0 | H |
| Me | 0 | Me |
| Me | 0 | Et |
| Me | 0 | Pr |
| Me | 0 | i-Pr |
| Me | 0 | c-Pr |
| Me | 0 | Bu |
| Me | 0 | t-Bu |
| Me | 0 | Pen |
| Me | 0 | Hex |
| Me | 0 | c-Hex |
| Me | 0 | All |
| Me | 0 | CH=CHMe |
| Me | 0 | Prop |
| Me | 0 | Q-1 |
| Me | 1 | Q-1 |
| Me | 0 | 2-Cl—Q-1 |
| Me | 0 | 2-OMe—Q-1 |
| Me | 0 | 2-$NO_2$—Q-1 |
| Me | 0 | 3-$NO_2$—Q-1 |
| Me | 0 | 2,5-$Cl_2$—Q-1 |
| Me | 2 | 2,5-$Cl_2$—Q-1 |
| Et | 0 | 2,5-$Cl_2$—Q-1 |
| Me | 0 | 3-Cl—Q-1 |
| Me | 0 | 2-CN—Q-1 |
| Me | 0 | 2-$CF_3$—Q-1 |
| Me | 0 | 2-Br—Q-1 |
| Me | 0 | 2-F—Q-1 |
| Me | 0 | 2-F-5-Cl—Q-1 |
| Me | 0 | 2-F-5-$NO_2$—Q-1 |
| Me | 0 | 2,3-$Cl_2$—Q-1 |
| Me | 0 | 3,4-$Cl_2$—Q-1 |
| Me | 0 | 3,5-$F_2$—Q-1 |
| Me | 0 | 3-F-5-Cl—Q-1 |
| Me | 0 | 3-F-5-$NO_2$—Q-1 |
| Me | 0 | 3-Cl-5-$NO_2$—Q-1 |
| Me | 0 | 3,5-$Cl_2$-4-OMe—Q-1 |
| Me | 0 | 2,5-$F_2$—Q-1 |
| Me | 0 | 3,5-$Cl_2$—Q-1 |
| Me | 0 | 3,5-$Cl_2$—Q-1 |
| Et | 0 | 3,5-$Cl_2$—Q-1 |
| Me | 0 | 3-$CO_2$—Et—Q-2 |
| Me | 0 | 2-Me—Q-3 |
| Me | 0 | 4,5-$Me_2$-3-CN—Q-6 ($R^4$: Me) |
| Me | 0 | 2-$CO_2$Et—Q-7 ($R^4$: Me) |
| Me | 0 | Q-8 ($R^4$: H) |
| Me | 0 | 3,5-$Cl_2$—Q-9 ($R^4$: Me) |
| Me | 0 | 3-Me—Q-10 ($R^4$: Me) |
| Me | 0 | 3-Me—Q-16 |
| Me | 0 | Q-20 |
| Me | 0 | 3-Me—Q-23 |
| Me | 0 | 5-Cl—Q-24 |
| Me | 0 | Q-27 |
| Me | 0 | 5-Cl—Q-28 |
| Me | 0 | Q-32 |
| Me | 2 | Q-32 |
| Me | 0 | 5-Cl—Q-32 |
| Me | 0 | Q-39 |
| Me | 2 | Q-39 |
| Me | 0 | 5-Cl—Q-40 |
| Me | 0 | 2,6-$Cl_2$-Q-41 |
| Me | 0 | Q-42 |
| Me | 0 | Q-43 |
| Me | 0 | Q-44 |
| Me | 0 | Q-45 |
| Me | 0 | Q-47 |
| Me | 0 | Q-48 |
| Me | 0 | Q-49 |
| Me | 0 | Q-52 |
| Me | 0 | Q-53 |
| Me | 0 | Q-57 |
| Me | 1 | Q-57 |
| Me | 0 | Q-59 |
| Me | 0 | 3-$CF_3$—Q-1 |
| Me | 0 | 3-F—Q-1 |
| Me | 0 | 3-Br—Q-1 |
| Me | 0 | 2-Cl-5-F—Q-1 |
| Me | 0 | 3,4,5-$Cl_3$—Q-1 |
| Me | 0 | 2,3,5-$Cl_3$—Q-1 |
| Me | 0 | 2-Cl-3,5-$F_2$—Q-1 |
| Me | 0 | 2,4,5-$F_3$—Q-1 |
| Me | 0 | 2,3,4,5-$F_4$—Q-1 |
| Me | 0 | 2-F-3,5-$Cl_2$—Q-1 |
| Me | 0 | 4-Me-5-Cl—Q-24 |
| Me | 0 | 6-Cl—Q-39 |
| Me | 0 | 5-Cl—Q-40 |
| Me | 0 | 2,5-$Cl_2$—Q-40 |
| Me | 0 | 2,6-$Cl_2$—Q-41 |
| Me | 0 | 2-Cl—Q-41 |
| Me | 0 | 4-Cl—Q-44 |
| Me | 0 | 4,6-$Cl_2$—Q-44 |
| Me | 0 | 2-Cl—Q-45 |
| Me | 0 | 2,6-$Cl_2$—Q-45 |
| Me | 0 | 6-Cl—Q-45 |
| Me | 0 | 3,6-$Cl_2$—Q-47 |
| Me | 0 | 6-Cl—Q-47 |
| Me | 0 | 4,6-$Cl_2$—Q-48 |
| Me | 0 | 2-Cl-5-$CF_3$—Q-1 |
| Me | 0 | 3,5-$(CF_3)_2$—Q-1 |
| Me | 0 | 2-F-5-$CF_3$—Q-1 |
| Me | 2 | 3,5-$F_2$—Q-1 |
| Me | 0 | 3-i-Pr—Q-1 |
| Me | 0 | 3-$OCHF_2$—Q-1 |
| Me | 0 | 3-CN—Q-1 |
| Me | 0 | 3-Me—Q-1 |

TABLE 3-D-continued
| Me | 0 | 3-F-5-CF$_3$—Q-1 |
| Me | 0 | 3-OMe—Q-1 |
| Me | 0 | 3-I—Q-1 |
| Me | 0 | 2-F-5-Me—Q-1 |
| Me | 0 | 2-F-5-Br—Q-1 |
| Me | 1 | 2,5-F$_2$—Q-1 |
| Me | 2 | 2,5-F$_2$—Q-1 |
| Me | 0 | 3-OMe-5-CF$_3$—Q-1 |
TABLE 3-E
In this table, J-1 to J-28 represent the followings.
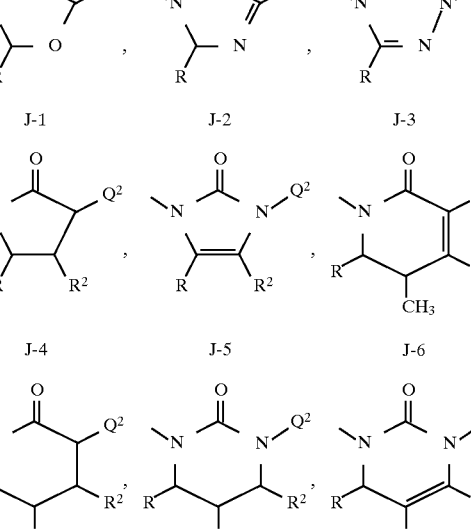
(J represents J-1, J-2, J-3 or J-22.)
| Q$^1$ | R | Q$^2$ |
|---|---|---|
| H | H | Q-1 |
| H | Me | Q-1 |
| H | H | 2-F-Q-1 |

-continued

| | | | |
|---|---|---|---|
| H | H | | 2-Cl-Q-1 |
| Et | H | | Q-1 |
| Et | Me | | Q-1 |
| Et | H | | 2-F-Q-1 |
| Et | H | | 2-Cl-Q-1 |
| 3-Cl-Q-1 | H | | Q-1 |
| 3-Cl-Q-1 | Me | | Q-1 |
| 3-Cl-Q-1 | H | | 2-F-Q-1 |
| 3-Cl-Q-1 | H | | 2-Cl-Q-1 |
| 3,5-Cl$_2$-Q-1 | H | | Q-1 |
| 3,5-Cl$_2$-Q-1 | Me | | Q-1 |
| 3,5-Cl$_2$-Q-1 | H | | 2-F-Q-1 |
| 3,5-Cl$_2$-Q-1 | H | | 2-Cl-Q-1 |
| 2-F-5-Cl-Q-1 | H | | Q-1 |
| 2-F-5-Cl-Q-1 | Me | | Q-1 |
| 2-F-5-Cl-Q-1 | H | | 2-F-Q-1 |
| 2-F-5-Cl-Q-1 | H | | 2-Cl-Q-1 |
| 2,5-F$_2$-Q-1 | H | | Q-1 |
| 2,5-F$_2$-Q-1 | Me | | Q-1 |
| 2,5-F$_2$-Q-1 | H | | 2-F-Q-1 |
| 2,5-F$_2$-Q-1 | H | | 2-Cl-Q-1 |
| 2,5-Cl$_2$-Q-1 | H | | Q-1 |
| 2,5-Cl$_2$-Q-1 | Me | | Q-1 |
| 2,5-Cl$_2$-Q-1 | H | | 2-F-Q-1 |
| 2,5-Cl$_2$-Q-1 | H | | 2-Cl-Q-1 |
| 3,5-F$_2$-Q-1 | H | | Q-1 |
| 3,5-F$_2$-Q-1 | Me | | Q-1 |
| 3,5-F$_2$-Q-1 | H | | 2-F-Q-1 |
| 3,5-F$_2$-Q-1 | H | | 2-Cl-Q-1 |
| 2-Cl-5-CF$_3$-Q-1 | H | | Q-1 |
| 2-Cl-5-CF$_3$-Q-1 | Me | | Q-1 |
| 2-Cl-5-CF$_3$-Q-1 | H | | 2-F-Q-1 |
| 2-Cl-5-CF$_3$-Q-1 | H | | 2-Cl-Q-1 |

(J represents J-4, J-5, J-6, J-8, J-11, J-13, J-19, J-20, J-26, J-27 or J-28.)

| Q$^1$ | R | R$^2$ | Q$^2$ |
|---|---|---|---|
| H | H | H | Q-1 |
| H | H | Me | Q-1 |
| H | Me | Me | Q-1 |
| H | H | H | 2-F-Q-1 |
| H | H | Me | 2-F-Q-1 |
| H | H | H | 2-Cl-Q-1 |
| H | H | Me | 2-Cl-Q-1 |
| Et | H | H | Q-1 |
| Et | H | Me | Q-1 |
| Et | Me | Me | Q-1 |
| Et | H | H | 2-F-Q-1 |
| Et | H | Me | 2-F-Q-1 |
| Et | H | H | 2-Cl-Q-1 |
| Et | H | Me | 2-Cl-Q-1 |
| 3-Cl-Q-1 | H | H | Q-1 |
| 3-Cl-Q-1 | H | Me | Q-1 |
| 3-Cl-Q-1 | Me | Me | Q-1 |
| 3-Cl-Q-1 | H | H | 2-F-Q-1 |
| 3-Cl-Q-1 | H | Me | 2-F-Q-1 |
| 3-Cl-Q-1 | H | H | 2-Cl-Q-1 |
| 3-Cl-Q-1 | H | Me | 2-Cl-Q-1 |
| 3,5-Cl$_2$-Q-1 | H | H | Q-1 |
| 3,5-Cl$_2$-Q-1 | H | Me | Q-1 |
| 3,5-Cl$_2$-Q-1 | Me | Me | Q-1 |
| 3,5-Cl$_2$-Q-1 | H | H | 2-F-Q-1 |
| 3,5-Cl$_2$-Q-1 | H | Me | 2-F-Q-1 |
| 3,5-Cl$_2$-Q-1 | H | H | 2-Cl-Q-1 |
| 3,5-Cl$_2$-Q-1 | H | Me | 2-Cl-Q-1 |
| 2-F-5-Cl-Q-1 | H | H | Q-1 |
| 2-F-5-Cl-Q-1 | H | Me | Q-1 |
| 2-F-5-Cl-Q-1 | Me | Me | Q-1 |
| 2-F-5-Cl-Q-1 | H | H | 2-F-Q-1 |
| 2-F-5-Cl-Q-1 | H | Me | 2-F-Q-1 |
| 2-F-5-Cl-Q-1 | H | H | 2-Cl-Q-1 |
| 2-F-5-Cl-Q-1 | H | Me | 2-Cl-Q-1 |
| 2,5-F$_2$-Q-1 | H | H | Q-1 |
| 2,5-F$_2$-Q-1 | H | Me | Q-1 |
| 2,5-F$_2$-Q-1 | Me | Me | Q-1 |
| 2,5-F$_2$-Q-1 | H | H | 2-F-Q-1 |
| 2,5-F$_2$-Q-1 | H | Me | 2-F-Q-1 |
| 2,5-F$_2$-Q-1 | H | H | 2-Cl-Q-1 |

-continued

| | | | |
|---|---|---|---|
| 2,5-F$_2$-Q-1 | H | Me | 2-Cl-Q-1 |
| 2,5-Cl$_2$-Q-1 | H | H | Q-1 |
| 2,5-Cl$_2$-Q-1 | H | Me | Q-1 |
| 2,5-Cl$_2$-Q-1 | Me | Me | Q-1 |
| 2,5-Cl$_2$-Q-1 | H | H | 2-F-Q-1 |
| 2,5-Cl$_2$-Q-1 | H | Me | 2-F-Q-1 |
| 2,5-Cl$_2$-Q-1 | H | H | 2-Cl-Q-1 |
| 2,5-Cl$_2$-Q-1 | H | Me | 2-Cl-Q-1 |
| 3,5-F$_2$-Q-1 | H | H | Q-1 |
| 3,5-F$_2$-Q-1 | H | Me | Q-1 |
| 3,5-F$_2$-Q-1 | Me | Me | Q-1 |
| 3,5-F$_2$-Q-1 | H | H | 2-F-Q-1 |
| 3,5-F$_2$-Q-1 | H | Me | 2-F-Q-1 |
| 3,5-F$_2$-Q-1 | H | H | 2-Cl-Q-1 |
| 3,5-F$_2$-Q-1 | H | Me | 2-Cl-Q-1 |
| 2-Cl-5-CF$_3$-Q-1 | H | H | Q-1 |
| 2-Cl-5-CF$_3$-Q-1 | H | Me | Q-1 |
| 2-Cl-5-CF$_3$-Q-1 | Me | Me | Q-1 |
| 2-Cl-5-CF$_3$-Q-1 | H | H | 2-F-Q-1 |
| 2-Cl-5-CF$_3$-Q-1 | H | Me | 2-F-Q-1 |
| 2-Cl-5-CF$_3$-Q-1 | H | H | 2-Cl-Q-1 |
| 2-Cl-5-CF$_3$-Q-1 | H | Me | 2-Cl-Q-1 |

(J represents J-7, J-9, J-10, J-12, J-14, J-17, J-18, or J-21.)

| Q$^1$ | R | R$^2$ | R$^5$ | Q$^2$ |
|---|---|---|---|---|
| H | H | H | H | Q-1 |
| H | H | H | Me | Q-1 |
| H | H | Me | H | Q-1 |
| H | Me | Me | H | Q-1 |
| H | H | Me | Me | Q-1 |
| H | H | H | H | 2-F-Q-1 |
| H | H | Me | H | 2-F-Q-1 |
| H | H | H | H | 2-Cl-Q-1 |
| H | H | Me | H | 2-Cl-Q-1 |
| Et | H | H | H | Q-1 |
| Et | H | H | Me | Q-1 |
| Et | H | Me | H | Q-1 |
| Et | Me | Me | H | Q-1 |
| Et | H | Me | Me | Q-1 |
| Et | H | H | H | 2-F-Q-1 |
| Et | H | Me | H | 2-F-Q-1 |
| Et | H | H | H | 2-Cl-Q-1 |
| Et | H | Me | H | 2-Cl-Q-1 |
| 3-Cl-Q-1 | H | H | H | Q-1 |
| 3-Cl-Q-1 | H | H | Me | Q-1 |
| 3-Cl-Q-1 | H | Me | H | Q-1 |
| 3-Cl-Q-1 | Me | Me | H | Q-1 |
| 3-Cl-Q-1 | H | Me | Me | Q-1 |
| 3-Cl-Q-1 | H | H | H | 2-F-Q-1 |
| 3-Cl-Q-1 | H | Me | H | 2-F-Q-1 |
| 3-Cl-Q-1 | H | H | H | 2-Cl-Q-1 |
| 3-Cl-Q-1 | H | Me | H | 2-Cl-Q-1 |
| 3,5-Cl$_2$-Q-1 | H | H | H | Q-1 |
| 3,5-Cl$_2$-Q-1 | H | H | Me | Q-1 |
| 3,5-Cl$_2$-Q-1 | H | Me | H | Q-1 |
| 3,5-Cl$_2$-Q-1 | Me | Me | H | Q-1 |
| 3,5-Cl$_2$-Q-1 | H | Me | Me | Q-1 |
| 3,5-Cl$_2$-Q-1 | H | H | H | 2-F-Q-1 |
| 3,5-Cl$_2$-Q-1 | H | Me | H | 2-F-Q-1 |
| 3,5-Cl$_2$-Q-1 | H | H | H | 2-Cl-Q-1 |
| 3,5-Cl$_2$-Q-1 | H | Me | H | 2-Cl-Q-1 |
| 2-F-5-Cl-Q-1 | H | H | H | Q-1 |
| 2-F-5-Cl-Q-1 | H | H | Me | Q-1 |
| 2-F-5-Cl-Q-1 | H | Me | H | Q-1 |
| 2-F-5-Cl-Q-1 | Me | Me | H | Q-1 |
| 2-F-5-Cl-Q-1 | H | Me | Me | Q-1 |
| 2-F-5-Cl-Q-1 | H | H | H | 2-F-Q-1 |
| 2-F-5-Cl-Q-1 | H | Me | H | 2-F-Q-1 |
| 2-F-5-Cl-Q-1 | H | H | H | 2-Cl-Q-1 |
| 2-F-5-Cl-Q-1 | H | Me | H | 2-Cl-Q-1 |
| 2,5-F$_2$-Q-1 | H | H | H | Q-1 |
| 2,5-F$_2$-Q-1 | H | H | Me | Q-1 |
| 2,5-F$_2$-Q-1 | H | Me | H | Q-1 |
| 2,5-F$_2$-Q-1 | Me | Me | H | Q-1 |
| 2,5-F$_2$-Q-1 | H | Me | Me | Q-1 |
| 2,5-F$_2$-Q-1 | H | H | H | 2-F-Q-1 |
| 2,5-F$_2$-Q-1 | H | Me | H | 2-F-Q-1 |

-continued

| Q¹ | R | R⁵ | Q² |
|---|---|---|---|
| 2,5-F₂-Q-1 | H | H | H | 2-Cl-Q-1 |
| 2,5-F₂-Q-1 | H | Me | H | 2-Cl-Q-1 |
| 2,5-Cl₂-Q-1 | H | H | H | Q-1 |
| 2,5-Cl₂-Q-1 | H | H | Me | Q-1 |
| 2,5-Cl₂-Q-1 | H | Me | H | Q-1 |
| 2,5-Cl₂-Q-1 | Me | Me | H | Q-1 |
| 2,5-Cl₂-Q-1 | H | Me | Me | Q-1 |
| 2,5-Cl₂-Q-1 | H | H | H | 2-F-Q-1 |
| 2,5-Cl₂-Q-1 | H | Me | H | 2-F-Q-1 |
| 2,5-Cl₂-Q-1 | H | H | H | 2-Cl-Q-1 |
| 2,5-Cl₂-Q-1 | H | Me | H | 2-Cl-Q-1 |
| 3,5-F₂-Q-1 | H | H | H | Q-1 |
| 3,5-F₂-Q-1 | H | H | Me | Q-1 |
| 3,5-F₂-Q-1 | H | Me | H | Q-1 |
| 3,5-F₂-Q-1 | Me | Me | H | Q-1 |
| 3,5-F₂-Q-1 | H | Me | Me | Q-1 |
| 3,5-F₂-Q-1 | H | H | H | 2-F-Q-1 |
| 3,5-F₂-Q-1 | H | Me | H | 2-F-Q-1 |
| 3,5-F₂-Q-1 | H | H | H | 2-Cl-Q-1 |
| 3,5-F₂-Q-1 | H | Me | H | 2-Cl-Q-1 |
| 2-Cl-5-CF₃-Q-1 | H | H | H | Q-1 |
| 2-Cl-5-CF₃-Q-1 | H | H | Me | Q-1 |
| 2-Cl-5-CF₃-Q-1 | H | Me | H | Q-1 |
| 2-Cl-5-CF₃-Q-1 | Me | Me | H | Q-1 |
| 2-Cl-5-CF₃-Q-1 | H | Me | Me | Q-1 |
| 2-Cl-5-CF₃-Q-1 | H | H | H | 2-F-Q-1 |
| 2-Cl-5-CF₃-Q-1 | H | Me | H | 2-F-Q-1 |
| 2-Cl-5-CF₃-Q-1 | H | H | H | 2-Cl-Q-1 |
| 2-Cl-5-CF₃-Q-1 | H | Me | H | 2-Cl-Q-1 |

(J represents J-15, J-16, J-23, J-24 or J-25.)

| Q¹ | R | R⁵ | Q² |
|---|---|---|---|
| H | H | H | Q-1 |
| H | H | Me | Q-1 |
| H | Me | H | Q-1 |
| H | H | H | 2-F-Q-1 |
| H | H | H | 2-Cl-Q-1 |
| Et | H | H | Q-1 |
| Et | H | Me | Q-1 |
| Et | Me | H | Q-1 |
| Et | H | H | 2-F-Q-1 |
| Et | H | H | 2-Cl-Q-1 |
| 3-Cl-Q-1 | H | H | Q-1 |
| 3-Cl-Q-1 | H | Me | Q-1 |
| 3-Cl-Q-1 | Me | H | Q-1 |
| 3-Cl-Q-1 | H | H | 2-F-Q-1 |
| 3-Cl-Q-1 | H | H | 2-Cl-Q-1 |
| 3,5-Cl₂-Q-1 | H | H | Q-1 |
| 3,5-Cl₂-Q-1 | H | Me | Q-1 |
| 3,5-Cl₂-Q-1 | Me | H | Q-1 |
| 3,5-Cl₂-Q-1 | H | H | 2-F-Q-1 |
| 3,5-Cl₂-Q-1 | H | H | 2-Cl-Q-1 |
| 2-F-5-Cl-Q-1 | H | H | Q-1 |
| 2-F-5-Cl-Q-1 | H | Me | Q-1 |
| 2-F-5-Cl-Q-1 | Me | H | Q-1 |
| 2-F-5-Cl-Q-1 | H | H | 2-F-Q-1 |
| 2-F-5-Cl-Q-1 | H | H | 2-Cl-Q-1 |
| 2,5-F₂-Q-1 | H | H | Q-1 |
| 2,5-F₂-Q-1 | H | Me | Q-1 |
| 2,5-F₂-Q-1 | Me | H | Q-1 |
| 2,5-F₂-Q-1 | H | H | 2-F-Q-1 |
| 2,5-F₂-Q-1 | H | H | 2-Cl-Q-1 |
| 2,5-Cl₂-Q-1 | H | H | Q-1 |
| 2,5-Cl₂-Q-1 | H | Me | Q-1 |
| 2,5-Cl₂-Q-1 | Me | H | Q-1 |
| 2,5-Cl₂-Q-1 | H | H | 2-F-Q-1 |
| 2,5-Cl₂-Q-1 | H | H | 2-Cl-Q-1 |
| 3,5-F₂-Q-1 | H | H | Q-1 |
| 3,5-F₂-Q-1 | H | Me | Q-1 |
| 3,5-F₂-Q-1 | Me | H | Q-1 |
| 3,5-F₂-Q-1 | H | H | 2-F-Q-1 |
| 3,5-F₂-Q-1 | H | H | 2-Cl-Q-1 |
| 2-Cl-5-CF₃-Q-1 | H | H | Q-1 |
| 2-Cl-5-CF₃-Q-1 | H | Me | Q-1 |
| 2-Cl-5-CF₃-Q-1 | Me | H | Q-1 |
| 2-Cl-5-CF₃-Q-1 | H | H | 2-F-Q-1 |
| 2-Cl-5-CF₃-Q-1 | H | H | 2-Cl-Q-1 |

Q-1 to Q-67 used in Tables 3-A-1, 3-A-2, 3-B, 3-C, 3-D and 3-E represent the groups illustrated below:

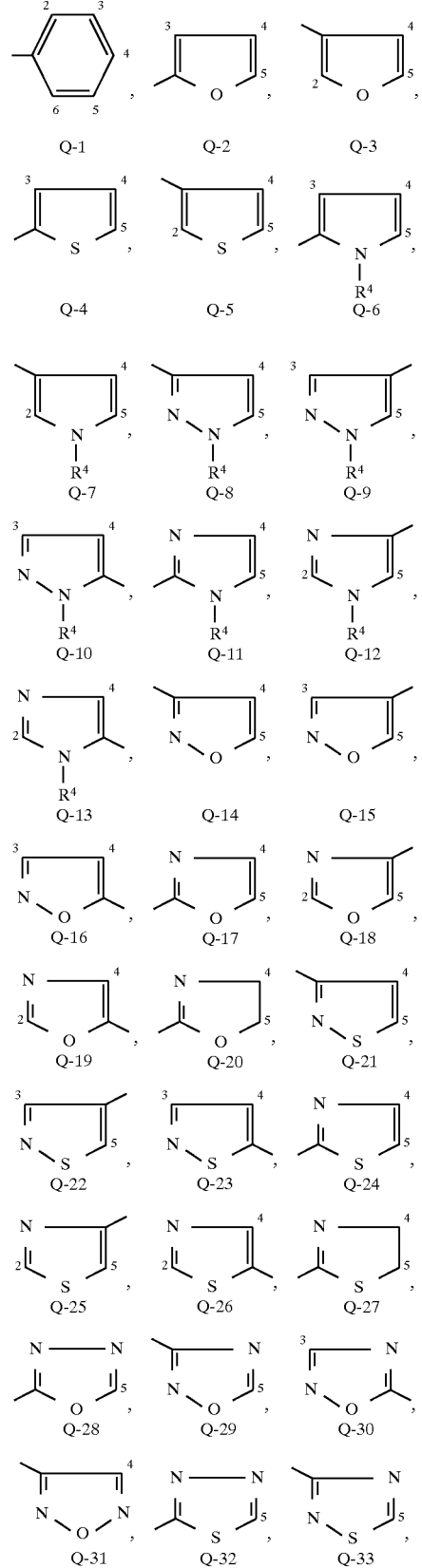

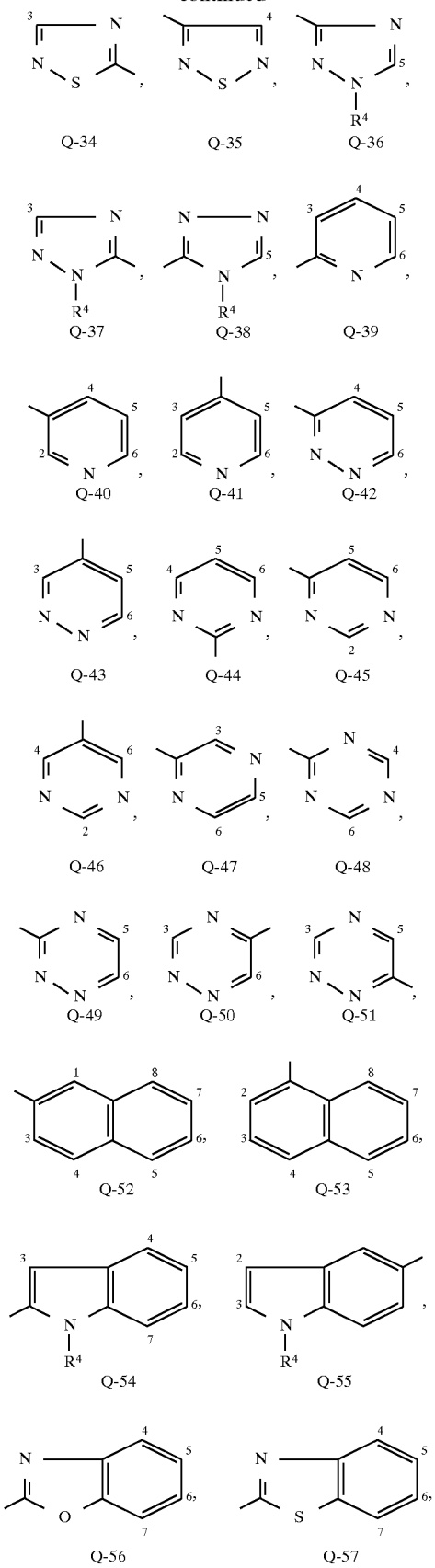
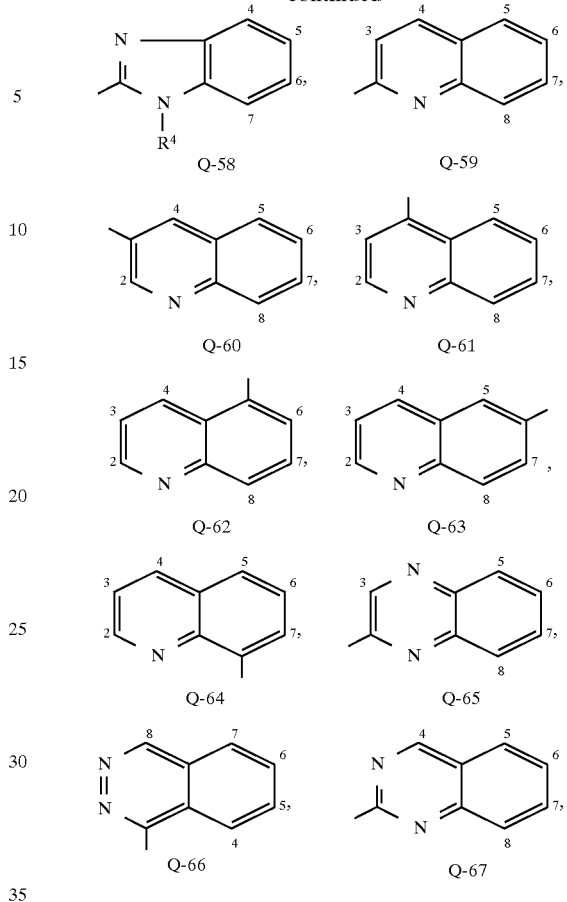

In use of the compounds of the present invention as a herbicide, they may be usually mixed with an appropriate carrier, for example, a solid carrier such as clay, talc, bentonite, diatomaceous earth and white carbon; or a liquid carrier such as water, alcohols (isopropanol, butanol, benzyl alcohol, furfuryl alcohol, etc.), aromatic hydrocarbons (toluene, xylene, etc.), ethers (anisole, etc.), ketones (cyclohexanone, isophorone, etc.), esters (butyl acetate, etc.), acid amides (N-methylpyrrolidone, etc.), and halogenated hydrocarbons (chlorobenzene, etc.). Also, if necessary, they may be added with a suitable adjuvant such as surfactant, emulsifier, dispersant, penetrating agent, spreader, thickener, anti-freezing agent, coagulation preventing agent, stabilizer and the like, and can be practically used in various forms of formulation such as liquid formulation, emulsifiable concentrate, wettable powder, dry flowable, flowable, dust or granule.

The compounds of the present invention may be mixed, if necessary, with other kinds of herbicide, various kinds of insecticide, fungicide, plant growth regulator, synergist and the like in the course of formulating process or at the time of application.

In particular, combined application of the compound of the present invention with other herbicide(s) can result in reducing the cost through decrease of the application rate, expanding the weeding spectrum and improving herbicidal performance through synergistic effect between combined herbicides. In this connection, the compound of the present invention may be combined with two or more known herbicides. As the kinds of herbicides which can be combined with the compound of the present invention in use thereof, there can be mentioned, for instance, the compounds described in Farm Chemicals Handbook (1994).

The application rate of the compound of the present invention as a herbicide is variable depending on the place, time and method of its application, and the crop to be treated and the like. It is, however, generally appropriate to apply the compound of the present invention as the active ingredient in an amount of about 0.0001–10 kg/ha, preferably about 0.001–5 kg/ha.

Shown below are the examples of formulations using the compounds of the present invention. It should be understood, however, that the formulations coming within the concept of the present invention are not limited to shown below. In the following description of the examples of formulations, all "parts" are by weight unless otherwise noted.

| Wettable Powder | |
| --- | --- |
| | Parts |
| Compound of the present invention | 5–80 |
| Solid carrier | 10–85 |
| Surfactant | 1–10 |
| Others | 1–5 |

(Others include coagulation preventing agent and the like.)

| Emulsifiable Concentrate | |
| --- | --- |
| | Parts |
| Compound of the present invention | 1–30 |
| Liquid carrier | 30–95 |
| Surfactant | 5–15 |

| Flowable | |
| --- | --- |
| | Parts |
| Compound of the present invention | 5–70 |
| Liquid carrier | 15–65 |
| Surfactant | 5–12 |
| Others | 5–30 |

(Others include anti-freezing agent, thickener and the like.)

| Granular Wettable Powder (Dry Flowable) | |
| --- | --- |
| | Parts |
| Compound of the present invention | 20–90 |
| Solid carrier | 9–60 |
| Surfactant | 1–20 |

| Granule | |
| --- | --- |
| | Parts |
| Compound of the present invention | 0.01–10 |
| Solid carrier | 90–99.99 |
| Others | 0–5 |

| Formulation Example 1: Wettable Powder | |
| --- | --- |
| | Parts |
| Compound A-2 of the present invention | 50 |
| Zeeklite PFP (kaolin type clay) (mfd. by Zeeklite Industries Co., Ltd.) | 43 |
| Sorpol 5050 (anionic surfactant) (mfd. by Toho Chemical Co., Ltd.) | 2 |
| Runox 1000 C (anionic surfactant) (mfd. by Toho Chemical Co., Ltd.) | 3 |
| Carplex #80 (coagulation preventing agent; white carbon) (mfd. by Shionogi Pharmaceutical Co., Ltd.) | 2 |

The above ingredients are homogeneously blended and ground to formulate a wettable powder.

| Formulation Example 2: Emulsifiable Concentrate | |
| --- | --- |
| | Parts |
| Compound A-4 of the present invention | 3 |
| Xylene | 76 |
| Isophorone | 15 |
| Sorpol 3005 X | 6 |

(mixture of nonionic and anionic surfactants; mfd. by Toho Chemical Co., Ltd.)

The above ingredients are homogeneously blended to formulate an emulsifiable concentrate.

| Formulation Example 3: Flowable | |
| --- | --- |
| | Parts |
| Compound A-5 of the present invention | 35 |
| Agrizole S-711 (nonionic surfactant) (mfd. by Kao Corporation) | 8 |
| Runox 1000 C (anionic surfactant) (mfd. by Toho Chemical Co., Ltd.) | 0.5 |
| 1% Rodopol water (thickener) (mfd. by Rhone-Poulenc) | 20 |
| Ethylene glycol (anti-freezing agent) | 8 |
| Water | 28.5 |

The above ingredients are homogeneously blended to formulate a flowable.

| Formulation Example 4: Granular Wettable Powder (Dry Flowable) | |
| --- | --- |
| | Parts |
| Compound A-6 of the present invention | 75 |
| Isobam No. 1 (anionic surfactant) (mfd. by Kuraray Isoprene Chemical Co., Ltd.) | 10 |
| Vanilex N (anionic surfactant) (mfd. by Sanyo Kokusaku Pulp K.K.) | 5 |
| Carplex #80 (white carbon) (mfd. by Shionogi Pharmaceutical Co., Ltd.) | 10 |

The above ingredients are homogeneously blended and pulverized to formulate a dry flowable.

Formulation Example 5: Granules

|  | Parts |
|---|---|
| Compound A-8 of the present invention | 0.1 |
| Bentonite | 55.0 |
| Talc | 44.9 |

The above ingredients are homogeneously blended and ground, to which then a small amount of water is added, and the resulting mixture is kneaded with stirring, granulated by an extrusion granulator and dried to formulate granules.

Formulation Example 6: Wettable Powder

|  | Parts |
|---|---|
| Compound B-2 of the present invention | 50 |
| Zeeklite PFP (kaolin type clay) (mfd. by Zeeklite Industries Co., Ltd.) | 43 |
| Sorpol 5050 (anionic surfactant) (mfd. by Toho Chemical Co., Ltd.) | 2 |
| Runox 1000 C (anionic surfactant) (mfd. by Toho Chemical Co., Ltd.) | 3 |
| Carplex #80 (coaguration preventing agent; white carbon) (mfd. by Shionogi Pharmaceutical Co., Ltd.) | 2 |

The above ingredients are homogeneously blended and ground to formulate a wettable powder.

Formulation Example 7: Emulsifiable Concentrate

|  | Parts |
|---|---|
| Compound B-4 of the present invention | 3 |
| Xylene | 76 |
| Isophorone | 15 |
| Sorpol 3005 X | 6 |

(mixture of nonionic and anionic surfactants; mfd. by Toho Chemical Co., Ltd.)

The above ingredients are homogeneously blended to formulate an emulsifiable concentrate.

Formulation Example 8: Flowable

|  | Parts |
|---|---|
| Compound B-6 of the present invention | 35 |
| Agrizole S-711 (nonionic surfactant) (mfd. by Kao Corporation) | 8 |
| Runox 1000 C (anionic surfactant) (mfd. by Toho Chemical Co., Ltd.) | 0.5 |
| 1% Rodopol water (thickener) (mfd. by Rhone-Poulenc) | 20 |
| Ethylene glycol (anti-freezing agent) | 8 |
| Water | 28.5 |

The above ingredients are homogeneously blended to formulate a flowable.

Formulation Example 9, Granular Wettable Powder (Dry Flowable)

|  | Parts |
|---|---|
| Compound B-3 of the present invention | 75 |
| Isobam No. 1 (anionic surfactant) (mfd. by Kuraray Isoprene Chemical Co., Ltd.) | 10 |
| Vanilex N (anionic surfactant) (mfd. by Sanyo Kokusaku Pulp K.K.) | 5 |
| Carplex #80 (white carbon) (mfd. by Shionogi Pharmaceutical Co., Ltd.) | 10 |

The above ingredients are homogeneously blended and pulverized to formulate a dry flowable.

Formulation Example 10: Granules

|  | Parts |
|---|---|
| Compound B-2 of the present invention | 0.1 |
| Bentonite | 55.0 |
| Talc | 44.9 |

The above ingredients are homogeneously blended and ground, to which then a small amount of water is added, and the resulting mixture is kneaded with stirring, granulated by an extrusion granulator and dried to formulate granules.

Formulation Example 11; Wettable Powder

|  | Parts |
|---|---|
| Compound C-28 of the present invention | 50 |
| Zeeklite PFP (kaolin type clay) (mfd. by Zeeklite Industries Co., Ltd.) | 43 |
| Sorpol 5050 (anionic surfactant) (mfd. by Toho Chemical Co., Ltd.) | 2 |
| Runox 1000 C (anionic surfactant) (mfd. by Toho Chemical Co., Ltd.) | 3 |
| Carplex #80 (coaguration preventing agent; white carbon) (mfd. by Shionogi Pharmaceutical Co., Ltd.) | 2 |

The above ingredients are homogeneously blended and ground to formulate a wettable powder.

Formulation Example 12: Emulsifiable Concentrate

|  | Parts |
|---|---|
| Compound C-15 of the present invention | 3 |
| Xylene | 76 |
| Isophorone | 15 |
| Sorpol 3005 X | 6 |

The above ingredients are homogeneously blended to formulate an emulsifiable concentrate.

Formulation Example 13; Flowable

|  | Parts |
|---|---|
| Compound C-30 of the present invention | 35 |
| Agrizole S-711 (nonionic surfactant) (mfd. by Kao Corporation) | 8 |
| Runox 1000 C (anionic surfactant) (mfd. by Toho Chemical Co., Ltd.) | 0.5 |
| 1% Rodopol water (thickener) (mfd. by Rhone-Poulenc) | 20 |
| Ethylene glycol (anti-freezing agent) | 8 |
| Water | 28.5 |

The above ingredients are homogeneously blended to formulate a flowable.

Formulation Example 14; Granular Wettable Powder (Dry Flowable)

| | Parts |
|---|---|
| Compound C-9 of the present invention | 75 |
| Isobam No. 1 (anionic surfactant) (mfd. by Kuraray Isoprene Chemical Co., Ltd.) | 10 |
| Vanilex N (anionic surfactant) (mfd. by Sanyo Kokusaku Pulp K.K.) | 5 |
| Carplex #80 (white carbon) (mfd. by Shionogi Pharmaceutical Co., Ltd.) | 10 |

The above ingredients are homogeneously blended and pulverized to formulate a dry flowable.

Formulation Example 15: Granules

| | Parts |
|---|---|
| Compound C-1 of the present invention | 0.1 |
| Bentonite | 55.0 |
| Talc | 44.9 |

The above ingredients are homogeneously blended and ground, to which then a small amount of water is added, and the resulting mixture is kneaded with stirring, granulated by an extrusion granulator and dried to formulate granules.

Formulation Example 16: Wettable Powder

| | Parts |
|---|---|
| Compound D-4 of the present invention | 50 |
| Zeeklite PFP (kaolin type clay) (mfd. by Zeeklite Industries Co., Ltd.) | 43 |
| Sorpol 5050 (anionic surfactant) (mfd. by Toho Chemical Co., Ltd.) | 2 |
| Runox 1000 C (anionic surfactant) (mfd. by Toho Chemical Co., Ltd.) | 3 |
| Carplex #80 (coagulation preventing agent; white carbon) (mfd. by Shionogi Pharmaceutical Co., Ltd.) | 2 |

The above ingredients are homogeneously blended and ground to formulate a wettable powder.

Formulation Example 17: Emulsifiable Concentrate

| | Parts |
|---|---|
| Compound A-55 of the present invention | 3 |
| Xylene | 76 |
| Isophorone | 15 |
| Sorpol 3005 X (mixture of nonionic and anionic surfactants; mfd. by Toho Chemical Co., Ltd.) | 6 |

The above ingredients are homogeneously blended to formulate an emulsifiable concentrate.

Formulation Example 18: Flowable

| | Parts |
|---|---|
| Compound A-82 of the present invention | 35 |
| Agrizole S-711 (nonionic surfactant) (mfd. by Kao Corporation) | 8 |
| Runox 1000 C (anionic surfactant) (mfd. by Toho Chemical Co., Ltd.) | 0.5 |
| 1% Rodopol water (thickener) (mfd. by Rhone-Poulenc) | 20 |
| Ethylene glycol (anti-freezing agent) | 8 |
| Water | 28.5 |

The above ingredients are homogeneously blended to formulate a flowable.

Formulation Example 19; Granular Wettable Powder (Dry Flowable)

| | Parts |
|---|---|
| Compound B-22 of the present invention | 75 |
| Isobam No. 1 (anionic surfactant) (mfd. by Kuraray Isoprene Chemical Co., Ltd.) | 10 |
| Vanilex N (anionic surfactant) (mfd. by Sanyo Kokusaku Pulp K.K.) | 5 |
| Carplex #80 (white carbon) (mfd. by Shionogi Pharmaceutical Co., Ltd.) | 10 |

The above ingredients are homogeneously blended and pulverized to formulate a dry flowable.

Formulation Example 20; Granules

| | Parts |
|---|---|
| Compound B-62 of the present invention | 0.1 |
| Bentonite | 55.0 |
| Talc | 44.9 |

The above ingredients are homogeneously blended and ground, to which then a small amount of water is added, and the resulting mixture is kneaded with stirring, granulated by an extrusion granulator and dried to formulate granules.

In practical use of the above formulations, the wettable powder, emulsifiable concentrate, flowable and granular wettable powder are diluted 50–1000 times with water and then applied so that the active ingredient will be supplied at a level of 1 to 10,000 ppm, or at a rate of 0.0001 to 10 kg per hectare.

The following test examples specifically illustrate the utility of the compound of the present invention as an active ingredient of herbicides.

Test Example 1; Test on herbicidal effect by soil treatment

A sterilized diluvial soil was placed in a 21 cm×13 cm×7 cm plastic cases. Each of seeds of barnyardgrass (*Echinochloa crus-galli*), green foxtail (*Setaria viridis*), soybean (*Glycine max*), cotton (*Gossypium herbaceum*) and corn (*Zea mays*) was sown spotwise, and covered with soil to the depth of about 1.5 cm, and then a spray liquid of test compound was uniformly applied over the soil surface by a small-sized sprayer so that the active ingredient would be supplied at the predetermined rate. Each of the spray liquid was prepared by diluting with water a wettable powder suitably prepared according to the relevant Formulation Examples described above, and was applied all over the soil surface. Three weeks after the application of each compound, its herbicidal effects on the said plants were examined and evaluated according to the following standard ratings. The growth control rate was determined based on the visual observation. The results are shown in Table 4.

Standard Rating

5: Growth control rate is more than 90%. (or plants are almost completely withered)
4: Growth control rate is 70 to 90%.
3: Growth control rate is 40 to 70%.
2: Growth control rate is 20 to 40%.
1: Growth control rate is 5 to 20%.
0: Growth control rate is less than 5%.

In Table 4, the symbols represent the following; A: barnyardgrass (*Echinochloa crus-galli*), B: green foxtail (*Setaria viridis*), a: soybean (*Glycine max*), b: cotton (*Gossypium herbaceum*), and c: corn (*Zea mays*).

TABLE 4

| Compound No. | Dose (kg/ha) | A | B | a | b | c |
| --- | --- | --- | --- | --- | --- | --- |
| A-2 | 0.63 | 5 | 5 | 0 | 0 | 4 |
| A-4 | 0.63 | 5 | 2 | 0 | 0 | 0 |
| A-5 | 0.63 | 5 | 5 | 0 | 0 | 0 |
| A-6 | 0.63 | 5 | 5 | 0 | 0 | 0 |
| A-8 | 0.63 | 4 | 5 | 0 | 0 | 0 |
| A-10 | 0.63 | 5 | 5 | 0 | 0 | 0 |
| A-11 | 0.63 | 5 | 5 | 0 | 0 | 3 |
| A-12 | 0.63 | 5 | 5 | 0 | 0 | 0 |
| A-13 | 0.63 | 5 | 5 | 0 | 0 | 0 |
| A-14 | 0.63 | 5 | 5 | 0 | 0 | 0 |
| A-16 | 0.63 | 5 | 5 | 0 | 0 | 3 |
| A-18 | 2.5 | 5 | 5 | 0 | 0 | 2 |
| A-19 | 2.5 | 5 | 5 | 0 | 0 | 2 |
| A-22 | 0.63 | 5 | 5 | 0 | 0 | 1 |
| A-23 | 0.63 | 5 | 5 | 0 | 0 | 0 |
| A-24 | 0.63 | 5 | 5 | 0 | 0 | 0 |
| A-25 | 0.63 | 5 | 5 | 0 | 0 | 0 |
| A-26 | 0.63 | 5 | 5 | 0 | 0 | 0 |
| A-27 | 0.63 | 5 | 5 | 0 | 0 | 0 |
| A-28 | 0.63 | 5 | 5 | 0 | 0 | 1 |
| A-29 | 0.63 | 5 | 5 | 0 | 0 | 0 |
| A-30 | 0.63 | 5 | 5 | 0 | 0 | 4 |
| A-31 | 0.63 | 5 | 5 | 0 | 0 | 2 |
| A-32 | 0.63 | 5 | 5 | 0 | 0 | 0 |
| A-33 | 0.63 | 5 | 5 | 0 | 0 | 2 |
| A-34 | 0.63 | 5 | 5 | 0 | 0 | 0 |
| A-35 | 0.63 | 5 | 5 | 0 | 0 | 4 |
| A-37 | 0.63 | 5 | 5 | 0 | 0 | 0 |
| A-38 | 0.63 | 5 | 5 | 0 | 0 | 0 |
| A-40 | 0.63 | 5 | 5 | 0 | 0 | 4 |
| A-42 | 0.63 | 5 | 5 | 0 | 0 | 2 |
| A-43 | 0.63 | 5 | 5 | 0 | 0 | 0 |
| A-44 | 0.63 | 5 | 5 | 0 | 0 | 3 |
| A-46 | 0.63 | 5 | 5 | 0 | 0 | 2 |
| A-47 | 0.63 | 5 | 5 | 0 | 0 | 3 |
| A-48 | 0.63 | 5 | 5 | 0 | 0 | 3 |
| A-50 | 0.63 | 5 | 5 | 0 | 0 | 2 |
| A-55 | 0.63 | 5 | 5 | 0 | 0 | 5 |
| A-56 | 0.63 | 5 | 5 | 0 | 0 | 5 |
| A-57 | 0.63 | 5 | 5 | 0 | 0 | 2 |
| A-58 | 0.63 | 5 | 5 | 0 | 0 | 0 |
| A-59 | 0.63 | 5 | 5 | 0 | 0 | 0 |
| A-61 | 0.63 | 5 | 5 | 3 | 0 | 5 |
| A-62 | 0.63 | 5 | 5 | 0 | 0 | 5 |
| A-63 | 0.63 | 5 | 5 | 0 | 0 | 1 |
| A-64 | 0.63 | 5 | 5 | 0 | 0 | 0 |
| A-65 | 0.63 | 5 | 5 | 0 | 0 | 5 |
| A-66 | 0.63 | 5 | 5 | 5 | 0 | 0 |
| A-67 | 0.63 | 5 | 5 | 3 | 0 | 0 |
| A-70 | 0.63 | 5 | 5 | 0 | 0 | 0 |
| A-71 | 0.63 | 5 | 5 | 0 | 0 | 0 |
| A-72 | 0.63 | 5 | 5 | 0 | 0 | 5 |
| A-73 | 0.63 | 5 | 5 | 0 | 0 | 5 |
| A-76 | 0.63 | 5 | 5 | 0 | 0 | 0 |
| A-78 | 0.63 | 5 | 5 | 0 | 0 | 5 |
| A-79 | 0.63 | 5 | 5 | 0 | 0 | 5 |
| A-80 | 0.63 | 5 | 5 | 0 | 0 | 5 |
| A-81 | 0.63 | 5 | 5 | 0 | 0 | 5 |
| A-82 | 0.63 | 5 | 5 | 2 | 0 | 4 |
| A-83 | 0.63 | 5 | 5 | 0 | 0 | 0 |
| A-84 | 0.63 | 5 | 5 | 0 | 0 | 0 |
| A-85 | 0.63 | 5 | 5 | 0 | 0 | 0 |
| A-86 | 0.63 | 5 | 5 | 0 | 0 | 5 |

TABLE 4-continued

| Compound No. | Dose (kg/ha) | A | B | a | b | c |
| --- | --- | --- | --- | --- | --- | --- |
| A-87 | 0.63 | 5 | 5 | 0 | 0 | 3 |
| A-88 | 0.63 | 5 | 5 | 0 | 0 | 0 |
| A-89 | 0.63 | 5 | 5 | 0 | 0 | 1 |
| A-90 | 0.63 | 5 | 5 | 0 | 0 | 0 |
| A-91 | 0.63 | 5 | 5 | 1 | 0 | 5 |
| A-92 | 0.63 | 5 | 5 | 0 | 0 | 5 |
| A-93 | 0.63 | 5 | 5 | 0 | 0 | 2 |
| A-94 | 0.63 | 5 | 5 | 0 | 0 | 2 |
| A-95 | 0.63 | 5 | 5 | 0 | 0 | 3 |
| A-96 | 0.63 | 5 | 5 | 0 | 0 | 0 |
| A-98 | 0.63 | 5 | 5 | 0 | 0 | 5 |
| A-99 | 0.63 | 5 | 5 | 0 | 0 | 0 |
| A-100 | 0.63 | 5 | 5 | 0 | 0 | 0 |
| A-101 | 0.63 | 5 | 5 | 3 | 0 | 5 |
| A-102 | 0.63 | 5 | 5 | 0 | 0 | 5 |
| A-103 | 0.63 | 5 | 5 | 0 | 0 | 5 |
| A-104 | 0.63 | 5 | 5 | 2 | 0 | 1 |
| A-105 | 0.63 | 5 | 5 | 2 | 0 | 2 |
| A-106 | 0.63 | 5 | 5 | 0 | 0 | 5 |
| A-107 | 0.63 | 5 | 5 | 0 | 0 | 0 |
| A-108 | 0.63 | 5 | 5 | 0 | 0 | 1 |
| A-109 | 0.63 | 5 | 5 | 0 | 0 | 5 |
| A-110 | 0.63 | 5 | 5 | 0 | 0 | 3 |
| A-111 | 0.63 | 5 | 5 | 1 | 0 | 4 |
| A-112 | 0.63 | 5 | 5 | 0 | 0 | 4 |
| A-113 | 0.63 | 5 | 5 | 4 | 0 | 4 |
| A-114 | 0.63 | 5 | 5 | 3 | 0 | 5 |
| A-115 | 0.63 | 5 | 5 | 0 | 0 | 0 |
| A-116 | 0.63 | 5 | 5 | 0 | 0 | 3 |
| A-117 | 0.63 | 5 | 5 | 0 | 0 | 0 |
| A-118 | 0.63 | 5 | 5 | 0 | 0 | 5 |
| A-119 | 0.63 | 5 | 5 | 0 | 0 | 0 |
| B-2 | 0.63 | 5 | 5 | 0 | 0 | 3 |
| B-3 | 0.63 | 5 | 5 | 0 | 0 | 4 |
| B-4 | 0.63 | 5 | 5 | 0 | 0 | 4 |
| B-6 | 0.63 | 5 | 5 | 2 | 1 | 4 |
| B-7 | 0.63 | 5 | 5 | 2 | 0 | 0 |
| B-8 | 0.63 | 5 | 5 | 1 | 0 | 3 |
| B-9 | 0.63 | 5 | 5 | 3 | 3 | 5 |
| B-13 | 0.63 | 5 | 5 | 0 | 0 | 5 |
| B-14 | 0.63 | 5 | 5 | 0 | 0 | 5 |
| B-15 | 0.63 | 5 | 5 | 2 | 0 | 5 |
| B-19 | 0.63 | 5 | 5 | 0 | 0 | 0 |
| B-21 | 0.63 | 5 | 5 | 2 | 0 | 5 |
| B-22 | 0.63 | 5 | 5 | 2 | 0 | 5 |
| B-23 | 0.63 | 5 | 5 | 0 | 0 | 2 |
| B-24 | 0.63 | 5 | 5 | 0 | 0 | 0 |
| B-25 | 0.63 | 5 | 5 | 0 | 0 | 0 |
| B-26 | 0.63 | 5 | 5 | 0 | 0 | 0 |
| B-27 | 0.63 | 5 | 5 | 0 | 0 | 5 |
| B-28 | 0.63 | 5 | 5 | 0 | 0 | 2 |
| B-29 | 0.63 | 5 | 5 | 0 | 0 | 0 |
| B-31 | 0.63 | 5 | 5 | 0 | 0 | 5 |
| B-32 | 0.63 | 5 | 5 | 3 | 0 | 5 |
| B-33 | 0.63 | 5 | 5 | 0 | 0 | 5 |
| B-34 | 0.63 | 5 | 5 | 4 | 0 | 0 |
| B-35 | 0.63 | 5 | 5 | 0 | 0 | 0 |
| B-36 | 0.63 | 5 | 5 | 3 | 4 | 5 |
| B-37 | 0.63 | 5 | 5 | 2 | 0 | 5 |
| B-38 | 0.63 | 5 | 5 | 0 | 0 | 3 |
| B-39 | 0.63 | 5 | 5 | 0 | 0 | 0 |
| B-40 | 0.63 | 5 | 5 | 3 | 4 | 5 |
| B-44 | 0.63 | 5 | 5 | 0 | 0 | 0 |
| B-50 | 0.63 | 5 | 5 | 0 | 0 | 0 |
| B-51 | 0.63 | 5 | 5 | 0 | 1 | 5 |
| B-52 | 0.63 | 5 | 5 | 0 | 4 | 5 |
| B-53 | 0.63 | 5 | 5 | 0 | 0 | 0 |
| B-54 | 0.63 | 5 | 5 | 0 | 0 | 0 |
| B-56 | 0.63 | 5 | 5 | 0 | 0 | 3 |
| B-57 | 0.63 | 5 | 5 | 0 | 0 | 3 |
| B-60 | 0.63 | 5 | 5 | 0 | 0 | 5 |
| B-61 | 0.63 | 5 | 5 | 1 | 0 | 5 |
| B-62 | 0.63 | 5 | 5 | 3 | 0 | 5 |
| B-63 | 0.63 | 5 | 5 | 1 | 0 | 5 |
| B-64 | 0.63 | 5 | 5 | 2 | 0 | 0 |
| B-65 | 0.63 | 5 | 5 | 2 | 0 | 1 |
| B-66 | 0.63 | 5 | 5 | 1 | 0 | 0 |

TABLE 4-continued

| Compound No. | Dose (kg/ha) | A | B | a | b | c |
|---|---|---|---|---|---|---|
| B-67 | 0.63 | 5 | 5 | 3 | 2 | 5 |
| B-68 | 0.63 | 5 | 5 | 0 | 0 | 2 |
| B-69 | 0.63 | 5 | 5 | 2 | 0 | 5 |
| B-70 | 0.63 | 5 | 5 | 0 | 0 | 5 |
| B-74 | 0.63 | 5 | 5 | 0 | 0 | 3 |
| B-76 | 0.63 | 5 | 5 | 0 | 0 | 0 |
| B-77 | 0.63 | 5 | 5 | 2 | 0 | 5 |
| B-78 | 0.63 | 5 | 5 | 2 | 0 | 5 |
| B-79 | 0.63 | 5 | 5 | 0 | 0 | 0 |
| B-83 | 0.63 | 5 | 5 | 2 | 0 | 5 |
| B-84 | 0.63 | 5 | 5 | 0 | 0 | 5 |
| B-85 | 0.63 | 5 | 5 | 0 | 0 | 5 |
| B-86 | 0.63 | 5 | 5 | 2 | 0 | 5 |
| B-87 | 0.63 | 5 | 5 | 4 | 0 | 0 |
| B-91 | 0.63 | 5 | 5 | 2 | 0 | 4 |
| B-92 | 0.63 | 5 | 5 | 2 | 0 | 5 |
| B-93 | 0.63 | 5 | 5 | 0 | 0 | 0 |
| B-94 | 0.63 | 5 | 5 | 0 | 0 | 0 |
| B-97 | 0.63 | 5 | 5 | 0 | 0 | 0 |
| B-98 | 0.63 | 5 | 5 | 4 | 0 | 5 |
| B-99 | 0.63 | 5 | 5 | 0 | 0 | 3 |
| B-100 | 0.63 | 5 | 5 | 0 | 0 | 0 |
| B-102 | 0.63 | 5 | 5 | 2 | 0 | 5 |
| B-104 | 0.63 | 5 | 5 | 0 | 2 | 5 |
| B-105 | 0.63 | 5 | 5 | 3 | 0 | 5 |
| B-106 | 0.63 | 5 | 5 | 0 | 0 | 5 |
| B-107 | 0.63 | 5 | 5 | 2 | 0 | 5 |
| B-108 | 0.63 | 5 | 5 | 0 | 0 | 4 |
| B-109 | 0.63 | 5 | 5 | 0 | 0 | 5 |
| C-1 | 2.5 | 5 | 5 | 0 | 0 | 2 |
| C-6 | 2.5 | 5 | 5 | 0 | 0 | 0 |
| C-8 | 2.5 | 5 | 5 | 0 | 0 | 0 |
| C-9 | 2.5 | 5 | 5 | 0 | 0 | 1 |
| C-12 | 2.5 | 5 | 5 | 0 | 0 | 2 |
| C-15 | 2.5 | 5 | 5 | 0 | 0 | 0 |
| C-16 | 2.5 | 5 | 5 | 0 | 0 | 0 |
| C-22 | 2.5 | 4 | 5 | 0 | 0 | 1 |
| C-26 | 2.5 | 4 | 4 | 0 | 0 | 0 |
| C-28 | 2.5 | 5 | 5 | 0 | 0 | 1 |
| C-29 | 2.5 | 5 | 5 | 0 | 0 | 0 |
| C-32 | 2.5 | 5 | 5 | 0 | 0 | 3 |
| C-33 | 2.5 | 5 | 5 | 0 | 0 | 4 |
| C-34 | 2.5 | 5 | 5 | 0 | 0 | 4 |
| C-35 | 2.5 | 5 | 5 | 0 | 0 | 3 |
| C-36 | 2.5 | 5 | 5 | 0 | 0 | 5 |
| C-37 | 2.5 | 5 | 5 | 0 | 0 | 5 |
| C-39 | 2.5 | 5 | 5 | 2 | 0 | 0 |
| C-42 | 2.5 | 5 | 5 | 0 | 0 | 2 |
| C-43 | 2.5 | 5 | 5 | 0 | 0 | 5 |
| C-44 | 2.5 | 5 | 5 | 0 | 0 | 5 |
| D-4 | 2.5 | 5 | 5 | 0 | 0 | 4 |
| D-5 | 2.5 | 5 | 5 | 0 | 0 | 5 |
| D-8 | 2.5 | 5 | 5 | 0 | 0 | 0 |

Test Example 2: Test on herbicidal effect by foliage treatment

A sterilized diluvial soil was placed in a 21 cm×13 cm×7 cm plastic cases. Each of seeds of barnyardgrass (Echinochloa crus-galli), green foxtail (Setaria viridis), velvetleaf (Abutilon theophrasti), cocklebur (Xanthium pensylvanicum), redroot (Amaranthus retroflexus) and morning-glory (Ipomoea purpurea) was sown spotwise and covered with soil to the depth of about 1.5 cm. When each of the plants grew to the 2- to 3-leaf stage, a spray liquid of test compound was uniformly applied to the foliage of the plants by a small-sized sprayer so that the active ingredient would be supplied at the predetermined rate. Each of the spray liquid was prepared by diluting with water a wettable powder suitably prepared according to the relevant Formula Examples described above, and was applied to cover the whole area of the case. Three weeks after the application of each compound, its herbicidal effects on the said plants were examined and evaluated according to the same standard ratings as used in Test Example 1. The results are shown in Table 5.

In Table 5, the symbols represent the following; A: barnyardgrass (Echinochloa crus-galli), B: green foxtail (Setaria viridis), C: velvetleaf (Abutilon theophrasti), D: cocklebur (Xanthium pensylvanicum), E: redroot (Amaranthus retroflexus) and F: morning-glory (Ipomoea purpurea).

TABLE 5

| Compound No. | Dose (kg/ha) | A | B | C | D | E | F |
|---|---|---|---|---|---|---|---|
| A-5 | 2.5 | 5 | 5 | 3 | 5 | 4 | 5 |
| A-6 | 2.5 | 5 | 5 | 5 | 5 | 4 | 5 |
| A-10 | 2.5 | 4 | 4 | 4 | 4 | | |
| A-11 | 2.5 | 5 | 5 | 3 | 5 | 4 | 3 |
| A-12 | 2.5 | 5 | 5 | 3 | 3 | 4 | 0 |
| A-13 | 2.5 | 5 | 5 | 4 | 5 | 4 | 0 |
| A-16 | 2.5 | 4 | 4 | 3 | 5 | 3 | 0 |
| A-18 | 2.5 | 4 | 4 | 3 | 5 | 3 | 0 |
| A-19 | 2.5 | 4 | 4 | 3 | 5 | 3 | 0 |
| A-22 | 2.5 | 5 | 5 | 5 | 5 | 4 | 0 |
| A-23 | 2.5 | 5 | 5 | 5 | 5 | 4 | 4 |
| A-24 | 2.5 | 5 | 5 | 4 | 5 | 3 | 3 |
| A-25 | 2.5 | 5 | 5 | 4 | 4 | 4 | 2 |
| A-28 | 2.5 | 5 | 5 | 4 | 5 | 4 | 4 |
| A-29 | 2.5 | 5 | 5 | 4 | 5 | 2 | 2 |
| A-30 | 2.5 | 5 | 5 | 3 | 0 | 0 | 0 |
| A-31 | 2.5 | 5 | 5 | 5 | 0 | 0 | 0 |
| A-33 | 2.5 | 5 | 5 | 5 | 5 | 3 | 0 |
| A-35 | 2.5 | 5 | 5 | 3 | 4 | 4 | 0 |
| A-40 | 2.5 | 5 | 5 | 4 | 4 | 4 | 0 |
| A-42 | 2.5 | 5 | 5 | 4 | 5 | 2 | 0 |
| A-44 | 2.5 | 5 | 5 | 5 | 5 | 4 | 0 |
| A-46 | 2.5 | 5 | 5 | 4 | 5 | 4 | 0 |
| A-47 | 2.5 | 5 | 5 | 0 | 4 | 0 | 0 |
| A-48 | 2.5 | 5 | 5 | 4 | 5 | 4 | 0 |
| A-49 | 2.5 | 5 | 5 | 0 | 5 | 2 | 0 |
| A-50 | 2.5 | 5 | 5 | 4 | 5 | 4 | 2 |
| A-52 | 2.5 | 5 | 5 | 0 | 4 | 0 | 0 |
| A-55 | 2.5 | 5 | 5 | 4 | 2 | 2 | 0 |
| A-56 | 2.5 | 5 | 5 | 0 | 4 | 0 | 0 |
| A-57 | 2.5 | 5 | 5 | 4 | 4 | 2 | 0 |
| A-58 | 2.5 | 5 | 5 | 0 | 5 | 0 | 0 |
| A-61 | 2.5 | 5 | 5 | 0 | 4 | 2 | 0 |
| A-62 | 2.5 | 5 | 5 | 4 | 4 | 0 | 0 |
| A-63 | 2.5 | 5 | 5 | 0 | 0 | 0 | 0 |
| A-66 | 2.5 | 5 | 5 | 4 | 5 | 0 | 0 |
| A-72 | 2.5 | 5 | 5 | 4 | 4 | 2 | 0 |
| A-73 | 2.5 | 5 | 5 | 4 | 5 | 4 | 0 |
| A-77 | 2.5 | 5 | 5 | 4 | 5 | 0 | 0 |
| A-78 | 2.5 | 5 | 5 | 4 | 3 | 3 | 0 |
| A-79 | 2.5 | 5 | 5 | 4 | 1 | 0 | 0 |
| A-80 | 2.5 | 5 | 5 | 4 | 3 | 0 | 0 |
| A-81 | 2.5 | 5 | 5 | 5 | 5 | 0 | 0 |
| A-82 | 2.5 | 5 | 5 | 5 | 5 | 4 | 0 |
| A-83 | 2.5 | 5 | 5 | 5 | 5 | 4 | 0 |
| A-84 | 2.5 | 5 | 5 | 4 | 2 | 3 | 0 |
| A-86 | 2.5 | 5 | 5 | 4 | 0 | 0 | 0 |
| A-87 | 2.5 | 5 | 5 | 4 | 4 | 4 | 0 |
| A-91 | 2.5 | 5 | 5 | 4 | 4 | 2 | 0 |
| A-92 | 2.5 | 5 | 5 | 4 | 4 | 2 | 0 |
| A-93 | 2.5 | 5 | 5 | 4 | 5 | 2 | 0 |
| A-94 | 2.5 | 5 | 5 | 4 | 4 | 4 | 0 |
| A-95 | 2.5 | 5 | 5 | 4 | 4 | 4 | 0 |
| A-98 | 2.5 | 5 | 5 | 5 | 5 | 4 | 0 |
| A-99 | 2.5 | 5 | 5 | 4 | 4 | 0 | 0 |
| A-100 | 2.5 | 5 | 5 | 4 | 4 | 3 | 0 |
| A-101 | 2.5 | 5 | 5 | 4 | 5 | 4 | 0 |
| A-102 | 2.5 | 5 | 5 | 0 | 5 | 2 | 0 |
| A-103 | 2.5 | 5 | 5 | 4 | 5 | 2 | 2 |
| A-104 | 2.5 | 5 | 4 | 4 | 4 | 2 | 0 |
| A-105 | 2.5 | 5 | 5 | 4 | 4 | 2 | 0 |
| A-106 | 2.5 | 5 | 5 | 2 | 0 | 0 | 0 |
| A-109 | 2.5 | 5 | 5 | 2 | 4 | 4 | 0 |
| A-110 | 2.5 | 5 | 5 | 0 | 4 | 0 | 0 |
| A-111 | 2.5 | 5 | 5 | 3 | 2 | 2 | 0 |

TABLE 5-continued

| Compound No. | Dose (kg/ha) | A | B | C | D | E | F |
|---|---|---|---|---|---|---|---|
| A-112 | 2.5 | 5 | 5 | 4 | 5 | 2 | 1 |
| A-114 | 2.5 | 5 | 5 | 4 | 4 | 2 | 0 |
| A-115 | 2.5 | 5 | 5 | 4 | 5 | 2 | 0 |
| A-119 | 2.5 | 5 | 5 | 0 | 0 | 0 | 0 |
| B-2 | 2.5 | 5 | 5 | 3 | 4 | 2 | 0 |
| B-3 | 2.5 | 5 | 5 | 3 | 5 | 2 | 0 |
| B-4 | 2.5 | 5 | 5 | 5 | 5 | 3 | 0 |
| B-6 | 2.5 | 5 | 5 | 5 | 4 | 4 | 0 |
| B-7 | 2.5 | 5 | 4 | 4 | 4 | 2 | 0 |
| B-8 | 2.5 | 5 | 5 | 4 | 5 | 3 | 0 |
| B-9 | 2.5 | 5 | 5 | 4 | 5 | 2 | 0 |
| B-14 | 2.5 | 5 | 5 | 0 | 5 | 0 | 0 |
| B-15 | 2.5 | 5 | 5 | 4 | 5 | 2 | 0 |
| B-21 | 2.5 | 5 | 5 | 4 | 3 | 2 | 0 |
| B-22 | 2.5 | 5 | 5 | 4 | 5 | 2 | 0 |
| B-27 | 2.5 | 5 | 5 | 4 | 2 | 2 | 0 |
| B-28 | 2.5 | 5 | 5 | 2 | 0 | 0 | 0 |
| B-29 | 2.5 | 5 | 5 | 0 | 2 | 0 | 0 |
| B-31 | 2.5 | 5 | 5 | 0 | 2 | 0 | 0 |
| B-32 | 2.5 | 5 | 5 | 4 | 4 | 0 | 0 |
| B-33 | 2.5 | 5 | 5 | 4 | 4 | 2 | 0 |
| B-36 | 2.5 | 5 | 5 | 4 | 5 | 4 | 0 |
| B-37 | 2.5 | 5 | 5 | 4 | 5 | 2 | 0 |
| B-39 | 2.5 | 5 | 5 | 4 | 0 | 0 | 0 |
| B-40 | 2.5 | 5 | 5 | 5 | 5 | 4 | 0 |
| B-51 | 2.5 | 5 | 5 | 5 | 5 | 4 | 0 |
| B-52 | 2.5 | 5 | 5 | 4 | 5 | 2 | 0 |
| B-53 | 2.5 | 5 | 5 | 4 | 2 | 2 | 0 |
| B-57 | 2.5 | 5 | 5 | 4 | 4 | 4 | 0 |
| B-60 | 2.5 | 5 | 5 | 4 | 5 | 3 | 0 |
| B-62 | 2.5 | 5 | 5 | 4 | 5 | 4 | 0 |
| B-63 | 2.5 | 5 | 5 | 4 | 5 | 4 | 0 |
| B-65 | 2.5 | 5 | 5 | 4 | 4 | 4 | 0 |
| B-67 | 2.5 | 5 | 5 | 5 | 5 | 5 | 0 |
| B-68 | 2.5 | 5 | 5 | 5 | 5 | 4 | 0 |
| B-69 | 2.5 | 5 | 5 | 4 | 4 | 4 | 0 |
| B-70 | 2.5 | 5 | 5 | 4 | 5 | 4 | 0 |
| B-74 | 2.5 | 5 | 5 | 4 | 4 | 4 | 0 |
| B-77 | 2.5 | 5 | 5 | 4 | 5 | 4 | 0 |
| B-78 | 2.5 | 5 | 5 | 4 | 5 | 4 | 0 |
| B-84 | 2.5 | 5 | 5 | 2 | 3 | 2 | 0 |
| B-85 | 2.5 | 5 | 5 | 0 | 4 | 3 | 0 |
| B-B6 | 2.5 | 5 | 5 | 2 | 4 | 2 | 0 |
| B-87 | 2.5 | 5 | 5 | 3 | 1 | 0 | 0 |
| B-91 | 2.5 | 5 | 5 | 3 | 4 | 3 | 0 |
| B-98 | 2.5 | 5 | 5 | 4 | 4 | 2 | 0 |
| B-100 | 2.5 | 5 | 5 | 4 | 2 | 0 | 0 |
| B-102 | 2.5 | 5 | 5 | 4 | 5 | 2 | 0 |
| B-104 | 2.5 | 5 | 5 | 2 | 4 | 2 | 0 |
| B-105 | 2.5 | 5 | 5 | 4 | 4 | 2 | 0 |
| B-106 | 2.5 | 5 | 5 | 4 | 4 | 2 | 0 |
| B-107 | 2.5 | 5 | 5 | 4 | 5 | 0 | 2 |
| B-108 | 2.5 | 5 | 5 | 3 | 4 | 2 | 0 |

Test Example 3: Test on herbicidal effect under flooding condition

An alluvial soil was placed in 1/10000 are Wagner pots and then water was poured thereinto to puddle the soil to form the miniature simulations of paddy field with 4 cm of the depth of flooding water. After the seeds of barnyardgrass (*Echinochloa crus-galli*) and bulrush (*Scirpus juncoides*) were sown in the above pots, the 2.5-leaf stage rice seedlings were transplanted. One day after the sowing, a diluted liquid with water of test compound was dropped onto the water surface with a measuring pipette so that the predetermined amount of compound would be supplied. The pots were placed in a 25 to 30° C. greenhouse to grow the plants. Three weeks after the application of each compound, its herbicidal effects on the said plants were examined and evaluated according to the same standard rating as used in Test Example 1. The results are shown in Table 6.

In Table 6, the symbols represent the following; A: barnyardgrass (*Echinochloa crus-galli*), G: bulrush (*Scirpus juncoides*) and d: transplanted rice (*Oryza sativa*).

TABLE 6

| Compound No. | Dose (kg/ha) | A | G | d |
|---|---|---|---|---|
| A-2 | 0.25 | 5 | 5 | 0 |
| A-4 | 0.25 | 5 | 5 | 0 |
| A-5 | 0.25 | 5 | 5 | 0 |
| A-6 | 0.25 | 5 | 5 | 0 |
| A-7 | 0.25 | 5 | 5 | 0 |
| A-8 | 0.25 | 5 | 5 | 0 |
| A-9 | 0.25 | 5 | 5 | 0 |
| A-10 | 0.25 | 5 | 5 | 0 |
| A-11 | 0.25 | 5 | 5 | 0 |
| A-12 | 0.25 | 5 | 5 | 0 |
| A-13 | 0.25 | 5 | 5 | 0 |
| A-14 | 0.25 | 5 | 5 | 0 |
| A-15 | 0.25 | 5 | 5 | 0 |
| A-16 | 0.25 | 5 | 5 | 0 |
| A-18 | 0.25 | 5 | 5 | 0 |
| A-19 | 0.25 | 5 | 5 | 0 |
| A-20 | 0.25 | 5 | 5 | 0 |
| A-21 | 0.25 | 5 | 5 | 0 |
| A-22 | 0.25 | 5 | 5 | 2 |
| A-23 | 0.25 | 5 | 5 | 0 |
| A-24 | 0.25 | 5 | 5 | 2 |
| A-25 | 0.25 | 5 | 5 | 0 |
| A-26 | 0.25 | 5 | 5 | 0 |
| A-27 | 0.25 | 5 | 5 | 0 |
| A-28 | 0.25 | 5 | 5 | 0 |
| A-29 | 0.25 | 5 | 5 | 0 |
| A-30 | 0.25 | 5 | 5 | 0 |
| A-31 | 0.25 | 5 | 5 | 0 |
| A-32 | 0.25 | 5 | 5 | 0 |
| A-33 | 0.25 | 5 | 5 | 0 |
| A-34 | 0.25 | 5 | 5 | 0 |
| A-35 | 0.25 | 5 | 5 | 0 |
| A-36 | 0.25 | 5 | 5 | 0 |
| A-37 | 0.25 | 5 | 5 | 0 |
| A-39 | 0.25 | 5 | 5 | 0 |
| A-40 | 0.25 | 5 | 5 | 0 |
| A-42 | 0.25 | 5 | 5 | 0 |
| A-43 | 0.25 | 5 | 5 | 0 |
| A-44 | 0.25 | 5 | 5 | 0 |
| A-46 | 0.25 | 5 | 5 | 0 |
| A-47 | 0.25 | 5 | 5 | 0 |
| A-48 | 0.25 | 5 | 5 | 0 |
| A-49 | 0.25 | 5 | 5 | 0 |
| A-50 | 0.25 | 5 | 5 | 0 |
| A-53 | 0.25 | 5 | 5 | 0 |
| A-54 | 0.25 | 5 | 5 | 0 |
| A-55 | 0.25 | 5 | 5 | 0 |
| A-56 | 0.25 | 5 | 5 | 0 |
| A-57 | 0.25 | 5 | 5 | 0 |
| A-58 | 0.25 | 5 | 5 | 0 |
| A-59 | 0.25 | 5 | 5 | 0 |
| A-60 | 0.25 | 5 | 5 | 0 |
| A-61 | 0.25 | 5 | 5 | 1 |
| A-62 | 0.25 | 5 | 5 | 0 |
| A-63 | 0.25 | 5 | 5 | 0 |
| A-64 | 0.25 | 5 | 5 | 0 |
| A-65 | 0.25 | 5 | 5 | 0 |
| A-66 | 0.25 | 5 | 5 | 0 |
| A-67 | 0.25 | 5 | 5 | 0 |
| A-69 | 0.25 | 5 | 5 | 0 |
| A-72 | 0.25 | 5 | 5 | 0 |
| A-73 | 0.25 | 5 | 5 | 5 |
| A-74 | 0.25 | 5 | 5 | 0 |
| A-75 | 0.25 | 5 | 5 | 0 |
| A-76 | 0.25 | 5 | 5 | 0 |
| A-77 | 0.25 | 5 | 5 | 0 |
| A-78 | 0.25 | 5 | 5 | 1 |
| A-79 | 0.25 | 5 | 5 | 0 |
| A-80 | 0.25 | 5 | 5 | 0 |
| A-81 | 0.25 | 5 | 5 | 0 |
| A-82 | 0.25 | 5 | 5 | 0 |
| A-83 | 0.25 | 5 | 5 | 0 |
| A-84 | 0.25 | 5 | 5 | 0 |

TABLE 6-continued

| Compound No. | Dose (kg/ha) | A | G | d |
|---|---|---|---|---|
| A-85 | 0.25 | 5 | 5 | 0 |
| A-86 | 0.25 | 5 | 5 | 0 |
| A-87 | 0.25 | 5 | 5 | 0 |
| A-88 | 0.25 | 5 | 5 | 0 |
| A-89 | 0.25 | 5 | 5 | 0 |
| A-90 | 0.25 | 5 | 5 | 0 |
| A-91 | 0.25 | 5 | 5 | 0 |
| A-92 | 0.25 | 5 | 5 | 3 |
| A-93 | 0.25 | 5 | 5 | 0 |
| A-94 | 0.25 | 5 | 5 | 0 |
| A-95 | 0.25 | 5 | 5 | 2 |
| A-96 | 0.25 | 5 | 5 | 1 |
| A-97 | 0.25 | 5 | 5 | 0 |
| A-98 | 0.25 | 5 | 5 | 2 |
| A-99 | 0.25 | 5 | 5 | 0 |
| A-100 | 0.25 | 5 | 5 | 0 |
| A-102 | 0.25 | 5 | 5 | 2 |
| A-103 | 0.25 | 5 | 5 | 0 |
| A-104 | 0.25 | 5 | 5 | 0 |
| A-105 | 0.25 | 5 | 5 | 0 |
| A-106 | 0.25 | 5 | 5 | 0 |
| A-107 | 0.25 | 5 | 5 | 0 |
| A-108 | 0.25 | 5 | 5 | 0 |
| A-109 | 0.25 | 5 | 5 | 0 |
| A-110 | 0.25 | 5 | 5 | 0 |
| A-111 | 0.25 | 5 | 5 | 0 |
| A-112 | 0.25 | 5 | 5 | 0 |
| A-113 | O.25 | 5 | 5 | 0 |
| A-114 | 0.25 | 5 | 5 | 0 |
| A-115 | 0.25 | 5 | 5 | 0 |
| A-116 | 0.25 | 5 | 5 | 0 |
| A-117 | 0.25 | 5 | 5 | 0 |
| A-118 | 0.25 | 5 | 5 | 0 |
| A-119 | 0.25 | 5 | 5 | 0 |
| B-2 | 0.25 | 5 | 5 | 2 |
| B-3 | 0.25 | 5 | 5 | 0 |
| B-4 | 0.25 | 5 | 5 | 2 |
| B-6 | 0.25 | 5 | 5 | 0 |
| B-7 | 0.25 | 5 | 5 | 0 |
| B-8 | 0.25 | 5 | 5 | 2 |
| B-9 | 0.25 | 5 | 5 | 2 |
| B-13 | 0.25 | 5 | 5 | 2 |
| B-14 | 0.25 | 5 | 5 | 0 |
| B-15 | 0.25 | 5 | 5 | 0 |
| B-19 | 0.25 | 5 | 5 | 0 |
| B-21 | 0.25 | 5 | 5 | 0 |
| B-22 | 0.25 | 5 | 5 | 0 |
| B-23 | 0.25 | 5 | 5 | 0 |
| B-24 | 0.25 | 5 | 5 | 0 |
| B-25 | 0.25 | 5 | 5 | 0 |
| B-26 | 0.25 | 5 | 5 | 0 |
| B-27 | 0.25 | 5 | 5 | 0 |
| B-28 | 0.25 | 5 | 5 | 0 |
| B-29 | 0.25 | 5 | 5 | 0 |
| B-30 | 0.25 | 5 | 5 | 0 |
| B-31 | 0.25 | 5 | 5 | 0 |
| B-32 | 0.25 | 5 | 5 | 0 |
| B-33 | 0.25 | 5 | 5 | 0 |
| B-34 | 0.25 | 5 | 5 | 0 |
| B-35 | 0.25 | 5 | 5 | 0 |
| B-36 | 0.25 | 5 | 5 | 0 |
| B-37 | 0.25 | 5 | 5 | 0 |
| B-38 | 0.25 | 5 | 5 | 0 |
| B-39 | 0.25 | 5 | 5 | 0 |
| B-40 | 0.25 | 5 | 5 | 1 |
| B-44 | 0.25 | 5 | 5 | 0 |
| B-49 | 0.25 | 5 | 5 | 0 |
| B-50 | 0.25 | 5 | 5 | 0 |
| B-51 | 0.25 | 5 | 5 | 0 |
| B-52 | 0.25 | 5 | 5 | 0 |
| B-53 | 0.25 | 5 | 5 | 0 |
| B-54 | 0.25 | 5 | 5 | 0 |
| B-56 | 0.25 | 5 | 5 | 0 |
| B-57 | 0.25 | 5 | 5 | 0 |
| B-60 | 0.25 | 5 | 5 | 1 |
| B-61 | 0.25 | 5 | 5 | 0 |
| B-62 | 0.25 | 5 | 5 | 0 |
| B-63 | 0.25 | 5 | 5 | 0 |
| B-64 | 0.25 | 5 | 5 | 1 |
| B-65 | 0.25 | 5 | 5 | 2 |
| B-66 | 0.25 | 5 | 5 | 0 |
| B-67 | 0.25 | 5 | 5 | 0 |
| B-68 | 0.25 | 5 | 5 | 0 |
| B-69 | 0.25 | 5 | 5 | 0 |
| B-70 | 0.25 | 5 | 5 | 0 |
| B-74 | 0.25 | 5 | 5 | 0 |
| B-76 | 0.25 | 5 | 5 | 0 |
| B-77 | 0.25 | 5 | 5 | 0 |
| B-78 | 0.25 | 5 | 5 | 0 |
| B-83 | 0.25 | 5 | 5 | 0 |
| B-84 | 0.25 | 5 | 5 | 0 |
| B-85 | 0.25 | 5 | 5 | 0 |
| B-86 | 0.25 | 5 | 5 | 0 |
| B-87 | 0.25 | 5 | 5 | 0 |
| B-91 | 0.25 | 5 | 5 | 0 |
| B-92 | 0.25 | 5 | 5 | 2 |
| B-93 | 0.25 | 5 | 5 | 0 |
| B-94 | 0.25 | 5 | 5 | 2 |
| B-95 | 0.25 | 5 | 5 | 0 |
| B-97 | 0.25 | 5 | 5 | 0 |
| B-98 | 0.25 | 5 | 5 | 4 |
| B-99 | 0.25 | 5 | 5 | 0 |
| B-100 | 0.25 | 5 | 5 | 0 |
| B-101 | 0.25 | 5 | 5 | 0 |
| B-102 | 0.25 | 5 | 5 | 0 |
| B-104 | 0.25 | 5 | 5 | 0 |
| B-105 | 0.25 | 5 | 5 | 0 |
| B-106 | 0.25 | 5 | 5 | 0 |
| B-107 | 0.25 | 5 | 5 | 0 |
| B-108 | 0.25 | 5 | 5 | 0 |
| B-109 | 0.25 | 5 | 5 | 0 |
| C-1 | 1 | 5 | 5 | 0 |
| C-6 | 1 | 5 | 5 | 0 |
| C-8 | 1 | 5 | 5 | 0 |
| C-10 | 1 | 5 | 5 | 0 |
| C-11 | 1 | 5 | 5 | 0 |
| C-13 | 1 | 4 | 5 | 0 |
| C-15 | 1 | 5 | 5 | 0 |
| C-16 | 1 | 5 | 5 | 0 |
| C-17 | 1 | 5 | 5 | 0 |
| C-18 | 1 | 5 | 5 | 0 |
| C-19 | 1 | 5 | 5 | 0 |
| C-20 | 1 | 5 | 5 | 0 |
| C-21 | 1 | 5 | 5 | 0 |
| C-22 | 1 | 5 | 5 | 0 |
| C-23 | 1 | 5 | 5 | 0 |
| C-24 | 1 | 5 | 5 | 0 |
| C-26 | 1 | 5 | 5 | 0 |
| C-28 | 1 | 5 | 5 | 0 |
| C-29 | 1 | 5 | 5 | 0 |
| C-30 | 1 | 5 | 5 | 0 |
| C-32 | 1 | 5 | 5 | 0 |
| C-33 | 1 | 5 | 5 | 0 |
| C-34 | 1 | 5 | 5 | 0 |
| C-35 | 1 | 5 | 5 | 0 |
| C-36 | 1 | 5 | 5 | 0 |
| C-37 | 1 | 5 | 5 | 0 |
| C-38 | 1 | 5 | 5 | 0 |
| C-39 | 1 | 5 | 5 | 0 |
| C-40 | 1 | 5 | 5 | 0 |
| C-41 | 1 | 5 | 5 | 0 |
| C-42 | 1 | 5 | 5 | 0 |
| C-43 | 1 | 5 | 5 | 0 |
| C-44 | 1 | 5 | 5 | 0 |
| D-4 | 1 | 5 | 5 | 0 |
| D-5 | 1 | 5 | 5 | 0 |
| D-7 | 1 | 5 | 5 | 0 |
| D-8 | 1 | 5 | 5 | 0 |
| D-9 | 1 | 5 | 5 | 0 |

We claim:

1. A nitrogen-containing cyclic compound represented by the formula (1):

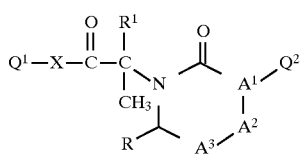

(wherein:
- $R^1$ represents a $C_1-C_4$ alkyl group;
- R represents a hydrogen atom or a $C_1-C_4$ alkyl group;
- X represents $NR^3$ (wherein $R^3$ represents a hydrogen atom or a methyl group);
- $Q^1$ represents an optionally substituted phenyl;
- $Q^2$ represents a $C_1-C_6$ alkyl, $C_3-C_7$ cycloalkyl or $C_3-C_6$ alkenyl group, or an optionally substituted phenyl or thienyl group;
- $A^1$ represents a carbon;
- $A^2$ represents $CR^2$ (wherein $R^2$ represents a hydrogen atom, or a $C_1-C_4$ alky, $C_3-C_6$ alkenyl or $C_3-C_6$ alkynyl group);
- $A^3$ represents $CR^5$ (wherein $R^5$ represents a hydrogen atom or a $C_1-C_4$ alkyl group);
- the ring comprising $A^3$ may have one or two double bonds within the ring.

2. A nitrogen-containing cyclic compound according to claim 1, wherein said nitrogen-containing cyclic compound is represented by the formula (1-b):

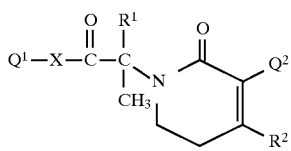

(wherein $R^2$ represents a $C_1-C_4$ alkyl group; and $Q^2$ represents an optionally substituted phenyl or thienyl group).

3. A nitrogen-containing cyclic compound according to claim 2, wherein $Q^1$ represents

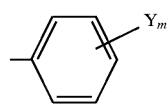

(wherein Y represents a halogen atom, or a $C_1-C_4$ alky, $C_1-C_4$ alkoxy, $C_1-C_4$ haloalkyl, $C_1-C_4$ haloalkoxy, $C_1-C_4$ alkylthio, $C_1-C_4$ alkylsulfinyl, $C_1-C_4$ alkylsulfonyl, ($C_1-C_4$ alkoxy)carbonyl or carboxyl group, or a nitro or cyano group; m represents an integer of 0 to 5; Y may be the same or different when m represents an integer of 2 to 5); and $Q^2$ represents ![structure](phenyl-Ze or thienyl-Ze)

(wherein Z represents a halogen atom, or a $C_1-C_4$ alkyl, $C_1-C_4$ alkoxy, $C_1-C_4$ haloalkyl or $C_1-C_4$ haloalkoxy group; e represents an integer of 0 to 3; Z may be the same or different when e represents 2 or 3).

4. A nitrogen-containing cyclic compound according to claim 3, wherein $R^1$ represents a methyl group; and $R^2$ represents a methyl or ethyl group.

5. A nitrogen-containing cyclic compound according to claim 4, wherein $Q^2$ represents ![structure](thienyl-Ze or thienyl-Ze)

6. A nitrogen-containing cyclic compound according to claim 4, wherein $Q^2$ represents 7. A herbicide comprising a nitrogen-containing cyclic compound according to claim 1.

8. A method for controlling weeds, which method comprises the use of a nitrogen-containing cyclic compound according to claim 1.

* * * * *

UNITED STATES PATENT AND TRADEMARK OFFICE
CERTIFICATE OF CORRECTION

PATENT NO. : 5,834,401
DATED : November 10, 1998
INVENTOR(S) : Kawamura, et al.

It is certified that error appears in the above-identified patent and that said Letters Patent is hereby corrected as shown below:

On the Cover page, in section [30] relating to Foreign Application Priority Data, for the date corresponding to Japanese Patent Application No. 6-157035, delete "July 5, 1994" and replace with --July 8, 1994--.

Signed and Sealed this

Twenty-fifth Day of May, 1999

Attest:

Attesting Officer

Q. TODD DICKINSON

Acting Commissioner of Patents and Trademarks